US012558401B2

(12) United States Patent (10) Patent No.: US 12,558,401 B2
Mose et al. (45) Date of Patent: Feb. 24, 2026

(54) INSULINOTROPIC AND GLUCAGONOTROPIC EFFECTS OF BETA-LACTOGLOBULIN

(71) Applicant: Arla Foods Amba, Viby J (DK)

(72) Inventors: Maike Mose, Aarhus N (DK); Nikolaj Fibiger Rittig, Risskov (DK); Niels Møller, Aarhus N (DK); Ulla Ramer Mikkelsen, Viby J (DK); Pernille Dorthea Frederiksen, Viby J (DK); Kasper Bøgelund Lauridsen, Viby J (DK); Britt Christensen, Viby J (DK); Mie Markholm, Viby J (DK); Søren Bang Nielsen, Viby (DK); Tanja Christine Jæger, Viby J (DK); Stine Bech Smedegaard, Viby J (DK); Adam Hulman, Rønde (DK)

(73) Assignee: Arla Foods Amba, Viby J (DK)

( * ) Notice: Subject to any disclaimer, the term of this patent is extended or adjusted under 35 U.S.C. 154(b) by 916 days.

(21) Appl. No.: 17/778,656

(22) PCT Filed: Nov. 20, 2020

(86) PCT No.: PCT/EP2020/082972

§ 371 (c)(1),
(2) Date: May 20, 2022

(87) PCT Pub. No.: WO2021/099611

PCT Pub. Date: May 27, 2021

(65) Prior Publication Data

US 2023/0000947 A1 Jan. 5, 2023

(30) Foreign Application Priority Data

Nov. 20, 2019 (EP) ..................................... 19210344

(51) Int. Cl.
*A61K 38/17* (2006.01)
*A61P 21/00* (2006.01)

(52) U.S. Cl.
CPC .......... *A61K 38/1722* (2013.01); *A61P 21/00* (2018.01)

(58) Field of Classification Search
CPC ........ A61K 38/1722; A61P 21/00; A61P 3/10; A23L 33/19
See application file for complete search history.

(56) References Cited

U.S. PATENT DOCUMENTS

2018/0153964 A1 6/2018 Jun et al.

FOREIGN PATENT DOCUMENTS

FR 2889067 2/2007
WO WO 2007/043870 4/2007

WO WO 2009/157767 12/2009
WO WO 2010/037736 4/2010
WO WO 2010/119088 10/2010
WO WO 2018/115520 6/2018
WO WO-2018115520 A1 * 6/2018 ............. A23C 21/00
WO WO 2020/001765 A1 1/2020
WO WO 2020/002426 A1 1/2020

OTHER PUBLICATIONS

Cao RY et al. Muscle Atrophy: Present and Future. Advances in Experimental Medicine and Biology, 2018, Chapter 29, p. 605-624 (Year: 2018).*
Mose M, et al., A model mimicking catabolic inflammatory disease; a controlled randomized study in humans. PLoS One. Nov. 5, 2020;15(11):e0241274. doi: 10.1371/journal.pone.0241274.
Abdulla, H., et al. Role of insulin in the regulation of human skeletal muscle protein synthesis and breakdown: a systematic review and meta-analysis. Diabetologia 59, 44-55 (2016). https://doi.org/10.1007/s00125-015-3751-0, Published Sep. 24, 2015.
Mose M, et al. Anabolic effects of oral leucine-rich protein with and without B-hydroxybutyrate on muscle protein metabolism in a novel clinical model of systemic inflammation—a randomized crossover trial. Am J Clin Nutr. Sep. 1, 2021;114(3):1159-1172. doi: 10.1093/ajcn/nqab148.
Argilés JM, et al., Skeletal Muscle Regulates Metabolism via Interorgan Crosstalk: Roles in Health and Disease. J Am Med Dir Assoc. Sep. 1, 2016;17(9):789-96. doi: 10.1016/j.jamda.2016.04.019. Epub Jun. 17, 2016.
Valio Oy, Valio Appelsiinitäysmehu perinteinen 1 l—Valio orange juice downloaded from https://www.metrotukku.fi/en/EUR/products/beverages/valio-orange-juice-traditional-1-1/6408430006007.
Tulipano G, et al., Whey proteins as source of dipeptidyl dipeptidase IV (dipeptidyl peptidase-4) inhibitors. Peptides. Apr. 2011;32(4):835-8. doi: 10.1016/j.peptides.2011.01.002. Epub Jan. 20, 2011.
Guardian IP Consulting, Reply to the Communication pursuant to Rule 79(1) EPC for EP Patent No. EP4061399B1 filed with the European Patent Office Mar. 26, 2025.

(Continued)

*Primary Examiner* — Paul J Holland
(74) *Attorney, Agent, or Firm* — Lisa Mueller; Tristan A. Fuierer; Casimir Jones SC

(57) ABSTRACT

The present invention pertains to a) beta-lactoglobulin or b) a nutritional composition comprising beta-lactoglobulin for use in preventing and/or treating a metabolic disorder and/or muscle atrophy. It also pertains to a method of preventing and/or treating a metabolic disorder and/or muscle atrophy in a subject. It furthermore pertains to use of a) beta-lactoglobulin or b) a nutritional composition comprising beta-lactoglobulin for increasing the level of insulin and/or glucagon in the blood of a subject and the present invention also pertains to a non-therapeutic use or method of a) beta-lactoglobulin or b) a nutritional composition comprising BLG. It also pertains to beta-lactoglobulin (BLG) for use in preventing and/or treating diabetes or prediabetes in a subject. It furthermore pertains to a nutritional composition for use in preventing and/or treating diabetes or prediabetes in a subject.

19 Claims, 51 Drawing Sheets

(56)         References Cited

OTHER PUBLICATIONS

Björkman, M.P., et al. "Whey protein supplementation in nursing home residents. A randdomized controlled trial" European Geriatric Medicine, 3, (2012), 161-166.
Calbet, Jose A.L., et al. "Plasma Glucagon and Insulin Responses Depend on the Rate of Appearance of Amino Acis after Ingestion of Different Protein Solutions in Humans 1,2", Human Nutrition and Metabolism, J. Nutr. 132: 2174-2182 (published in 2002).
Gilmartin, Sarah, et al. "Whey for Sarcopenia; Can Whey Peptides Hydrolysates or Proteins Play a Beneficial Role?", Foods 2020, 9, 750 (publishd May 6, 2020).
Handbook of food proteins, edited by G.O. Phillips and P.A. Williams, published by Woodhead Publishing Limited, Chapter 3, "Whey proteins", M. Boland, Riddet Institute, Massey University, New Zealand (published in 2011).
Hollingworth TW et al. "Getting to grips with sarcopenia: recent advances and practical management for the gastroenterologist" Frontline Gastroenterology 2021; 12:53-61 (published on Jan. 20, 2020).
Wickipedia—entry for Cachexia—https://en.wikipedia.org/wiki/Cachexia (from 2024).
MedlinePlus, entry for Muscle Atrophy—https://medlineplus.gov/ency/article/003188.htm (from 2024).
Ulla Ramer Mikkelsen—Inventor Declaration for EP Application No. 20808127.3.
Jakubowicz, Daniela; Froy, Oren. "Biochemical and metabolic mechanisms by which dietary whey protein may combat obesity and Type 2 diabetes" Journal of Nutritional Biochemistry 24 (2013) 1-5 (published in 2013).
Leenders, Marika, et al. "Leucine as a pharmaconutrient to prevent and treat sarcopenia and type 2 dibetes" Nutrition Reviews, vol. 69 (11) : 675-689.
Manders, Ralph J., et al. "Insulinotropic and Muscle Protein Synthetic Effects of Branched-Chain Amino. Acids: Potential Therapy for Type 2 Diabetes and Sarcopenia".
Mortensen, et al. "Effects of different fractions of whey protein on postprandial lipid and hormone. Responses in type 2 diabetes" European Journal of Clincal Nutrition, 2012, 66—pp. 799-805, XP55217581.
Rieu, Isabelle, et al. "Increased availability of leucine with leucine-rich whey proteins improves. Postprandial muschle protein synthesis in aging rats", Nutrition, 23, 2007, 323-331.
Arla Foods AMBA, response to Rule 161-162EPC for EP Application No. 20808127.3, Apr. 25, 2023.
Arla Foods Ingredient Group P/S, Summary of the dossier: Beta-Lactoglobulin, https:///food.ec.europa.eu/safety/novel-food/authorisations/summaryapplications-and-notifications_en published on May 8, 2020).
Tsutsumi, Rie, et al. "Peptides and Proteins in Whey and Their Benefits for Human Health" Austin Journal of Nutrition and Food Sciences, vol. 1, Issue 1, 2014.
Tulipano, Giovanni, et al. "Characterisation of the potential of Beta-lactoglobulin and alpa-lactalbumin as sources of bioactive peptides affecting incretin function: In silico and in vitro comparative studies" International Dairy Journal 48, (2015), 66-72.
Usman Mir Khan, Zeliha Selamoglu, "Nutritional and Medical Perspectives of Whey Protein: A historical Overview", J Pharm Care 2019; 7(4): 112-117 (published on Dec. 31, 2019).
Meijer, Whey Flavor Whey Protein Dietary Supplement, True Goodness by Meijer, Apr. 2019.
Yang, Jichun, et al. "Leucine metabolism in regulationof insulin secretion from pancreatic beta cells" Nutrition Reviews, vol. 68(5), 270-279, published 2010.
European Patent Office, Notice of Opposition from N.V. Nutricia against EP Patent No. EP 4061399 B1, dated Nov. 13, 2024.
European Patent Office, Notice of Opposition from Zimmermann and Partner Patentanwälte mbB dated Nov. 14, 2024.
Adams, Rachel L., et al: "Insulinotropic Effects of Whey: Mechanisms of Action, Recent Clinical Trials, and Clinical Applications"

Annals of Nutrition and Metabolism: European Journal of Nutrition, Metabolic Diseases and Dietetics, vol. 69, No. 1, Jan. 1, 2016, pp. 56-63.
Akhavan et al. "Effect of premeal on consumption of whey proteins and its hydrolysate on food intake and postmeal glycemia and insulin response"—Am J Clin Nutr. Apr. 2010, 91(4)-966-75.
Akhavan et al. "Mechanism of action of pre-meal consumption of whey protein on glycemic control in young adults" J Nutr Biochem. Jan. 2014, 25(1): 36-43.
Bae, Kim, et al "Postprandial glucose-lowering effect of premeal consumption of protein-enriched, dietary fibre fortified bar in individuals with type 2 diabetes mellitus or normal glucose tolerance" J. Diabetes Investig vol. 9, No. 5 Sep. 2018.
Bjørshave, Ann, et al. "Effects of Dairy Protein and Fat on the Metabolic Syndrome and Type 2 Diabetes", The review of diabetic studies, vol. 11, No. 2, Jan. 1, 2014, pp. 153, 166, XP055678422.
Carnovale et al. "Effect of the consumption of beta-lactoglobulin and epigallotechin-3-gallate with or without calcium on glucose tolerance in C57BL/6mice" International Journal of food sciences and nutrion, vol. 67, 2016, issue 3.
Diabetes Care. Jan. 2010; 33 (Suppl 1): S62-869. Diagnosis and Classification of Diabetes Mellitus. American Diabetes Association. doi: 10.2337/dc10-S062.
Etzel M R: "Manufacture and use of dairy protein fractions", The Journal of Nutrition, American Society for Nutrition, US, vol. 134, Jan. 1, 2004, pp. 996S-1002S, XP002529524.
Gilbert, J-A, et al: "Effect of proteins from different sources on body composition", NMCD. Nutrition Metabolism and Cardiovascular Diseases, Milan, IT, vol. 21, Dec. 27, 2010, pp. B16-B31, XP028284539.
Gillespie, Anna L., et al: "Whey proteins have beneficial effects on intestinal enteroendocrine cells stimulating cell growth and increasing the production and secretion of incretin hormones" Food Chemistry, vol. 189, Dec. 1, 2015, pp. 120-128, XP055771685.
Giovanni, Tulipano, et al: "Characterisation of the potential of (beta)-lactoglobulin and aopha)-lactalbumn as sources of bioactive peptides affecting incretin function: In silico and in vitro comparative", International Dairy Journal, Elsevier Applied Science, Barking, GB, vol. 48, Jan. 24, 2015.
Hong, Yeonhee, et al: "Amelioration of muscle wasting by glucagon-lik peptide-1 receptor agonist in muscle atrophy", Journal of Cachexia, Sarcopenia and muscle, Dec. 2013, vol. 10, No. 4, Apr. 24, 2019, pp. 903-918, XP055771916.
Lindgren, Ole, et al "Incretin Hormone and Insulin Responses to Oral Versus Intravenous Lipd Administration in Humans" J Clin Endocrinol Metab, Aug. 2011, 96(8): 2519-2524.
Love, Kaitlin M., "GLP-1 and insulin regulation of skeletal and cardiac muscle microvascular perfusion in type 2 diabetes" Journal of Diabetes 2020; 12: 488-498.
Madureira, et al. "Bovine whey proteins—Overview on their main biological properties", Food Research International, Elsevier, Amsterdam, NL. vol. 40, No. 10, Oct. 22, 2007, pp. 1197-1211, XP022308619.
Mignone, Linda E., et al. "Whey protein: The "whey" forward for treatment of type 2 diabetes?", World Journal of Diabetes, vol. 6, No. 14, Jan. 1, 2015, pp. 1274, 1284, XP055678409.
Mortensen, L.S. et al. "Effects of different fractions of whey protein on postprandial lipid and hormone responses in type 2 diabetes" European Journal of Clinical Nutrition, vol. 66, No. 7, May 16, 2012, pp. 799-805, XP055217581.
Ogiwara et al "Enzymatic digest of whey protein and wheylin-1, a dipeptide released in the digest, increase insulin sensitivity in an Akt phosphorylation-dependent manner", Jouna: Food and Function,. 2018, 9, 4635-4641.
Parikh, Rakesh M., et al. Changing definitions of metabolic syndrome Indian J Endocrinol Metab. Jan.-Feb. 16, 2012; 16(1): 7-12. Doi:10.41033/2230-821.91175.
Smedegaard, Stine B., et al: "(beta)-lactoglobulin Elevates Insulin and Glucagon Concentrations Compared with Whey Protein—A Randomized Double-Blinded Crossover Trial in Patients with Type Two Diabetes Mellitus", Nutrients, vol. 13, No. 2, Jan. 22, 2021, p. 308, XP055771676.
Subaran, et al. "GLP-1 at physioloical concentrations recruits skeletal and cardiac muscle microvasculature in healthy humans" Clin Sci (Lond) Aug. 2014; 127(3): 163-170.

(56)     References Cited

OTHER PUBLICATIONS

Tsuda et al. "Trypsin-Treated Beta-lactoglobulin Improves Glucose Tolerance in C57BL/6 Mice by Enhancing AMPK Activation and Glucose UPtake in Hepatocytes" Biol. Pharm. Bull. 40, 1917-1922 (2017).

Tsutsumi, Rie, et al. "Peptides and proteins in whey and their benefits for human health" Austin Journal of Nutrition and Food Science, vol. 1, No. 1, Jan. 1, 2014, pp. 1-9, XP055678415.

Uchida "Novel Dipeptidyl Peptidase-4-Inhibiting Peptide Derived from Betal-Lactoglobulin" Journal: J Pharmacol Sci 117, 63-66—2011.

Ørskov, Cathrine, et al. "Tissue and Plasma Concentrations of Amidated and Glycine-Extended Glucagon-Like Peptide I in Humans", Diabetes, vol. 43, Apr. 1994.

Jespersen, J., et al., "Activated Protein Synthesis and Suppressed Protein Breakdown Signaling in Skeletal Muscle of Critically III Patients," PLoS One. Mar. 31, 2011;6(3):e18090. doi: 10.1371/journal.pone.0018090. PMID: 21483870; PMCID: PMC3069050.

Mann, G., et al., "Branched-Chain Amino Acids: Catabolismin Skeletal Muscle and Implications for Muscle and Whole-Body Metabolism," Front Physiol. Jul. 20, 2021;12:702826. doi: 10.3389/fphys.2021.702826. PMID: 34354601; PMCID: PMC8329528.

Mose, M., et al. "A model mimicking catabolic inflammatory disease; a controlled randomized study in humans," PLoS One. Nov. 5, 2020;15(11):e0241274. doi: 10.1371/journal.pone.0241274. PMID: 33151986; PMCID: PMC7644057.

Mose, M., et al. "Anabolic effects of oral leucine-rich protein with and without ß -hydroxybutyrate on muscle protein metabolism in a novel clinical model of systemic inflammation—a randomized crossover trial," Am J Clin Nutr 2021;00:1-14,=. Published by Oxford University Press on behalf of the American Society for Nutrition.

Zhao, Y., et al. "Advances in the Role of Leucine-Sensing in the Regulation of Protein Synthesis in Aging Skeletal Muscle," Front Cell Dev Biol. Apr. 1, 2021;9:646482. doi: 10.3389/fcell.2021.646482. PMID: 33869199; PMCID: PMC8047301.

* cited by examiner

Figure 7

INSULINOTROPIC AND GLUCAGONOTROPIC EFFECTS OF BETA-LACTOGLOBULIN

FIELDS OF THE INVENTION

The present invention pertains to a) Beta-lactoglobulin or b) a nutritional composition comprising beta-lactoglobulin for use in preventing and/or treating a metabolic disorder and/or muscle atrophy. It also pertains to a method of preventing and/or treating a metabolic disorder and/or muscle atrophy in a subject. It furthermore pertains to use of a) beta-lactoglobulin or b) a nutritional composition comprising beta-lactoglobulin for increasing the level of insulin and/or glucagon in the blood of a subject and the present invention also pertains to a non-therapeutic use or method of a) beta-lactoglobulin or b) a nutritional composition comprising BLG. The present invention furthermore pertains to beta-lactoglobulin (BLG) for use in preventing and/or treating diabetes or prediabetes in a subject. It furthermore pertains to a nutritional composition for use in preventing and/or treating diabetes or prediabetes in a subject.

BACKGROUND OF THE INVENTION

Insulin and glucagon are important hormones in the human metabolism as they play an important role in regulating the levels of blood glucose and lipids in the body. Insulin and glucagon thus work together to balance the blood glucose and lipid levels, keeping them in the narrow range that the body requires. Insulin lowers the blood glucose level while glucagon raises the level. Regulating these hormones is therefore very important for the treatment and/or prevention of a number of diseases such as metabolic disorders and muscle atrophy.

Insulin is an essential hormone produced in the beta-cells of the pancreatic gland, and the main role of insulin is to transport glucose from the bloodstream into the body's cells, where glucose is converted into energy. The lack of insulin or the inability of the cells to respond to insulin (decreased insulin sensitivity) leads to high levels of blood glucose, hyperglycaemia, which in time causes a variety of complications (e.g. cardiovascular disease, neurodegenerative disease, kidney disease and eye disease). Insulin also plays an important role in dampering lipid concentrations in the blood stream as insulin increases the uptake of lipids in the muscles.

Glucagon is also an essential peptide hormone, produced by the alpha cells of the pancreas. It works to raise the concentration of glucose in the bloodstream, and it is considered to be the main catabolic hormone of the body. Glucagon also has an ability to increase energy expenditure and inhibit appetite. Administration of proteins that increases the level of glucagon in the blood will therefore have a potential in the fight against for example obesity and fatty liver disease.

Insulin and glucagon are thus also closely related to diabetes mellitus (diabetes), the prevalence of which continues to increase in the western world. At present nearly half a billion people live with diabetes. Diabetes is a chronic condition that occurs when levels of glucose in the blood are elevated, due to an imbalance between insulin sensitivity and insulin production. Diabetes thus has a severe health impact, if not treated. However, if appropriate management of diabetes is achieved, the serious complications of diabetes can be delayed or prevented.

A number of attempts have therefore been taken to treat and/or prevent diabetes, see for example "Postprandial glucose-lowering effect of premeal consumption of protein-enriched, dietary fibre fortified bar in individuals with type 2 diabetes mellitus or normal glucose tolerance, J Diabetes Investig Vol. 9 No. 5 September 2018 Jae Hyun Bae, Lee Kyung Kim, Se Hee Min, Chang Ho Ahn, Young Min Cho.

SUMMARY OF INVENTION

The present inventors have made the surprising discovery that administration of BLG or a nutritional composition comprising BLG in a purity of at least 75% relative to total protein has both an insulinotropic effect and a glucagonotropic effect in human subjects. The insulin and glucagon stimulatory effects are superior to those obtained by using similar doses of whey protein isolate (WPI) as a protein source.

This opens up for using BLG-enriched products to prevent and/or treat disorders relating to imbalances of these hormones related to metabolic disorders and/or muscle atrophy or for therapeutic or non-therapeutic treatment to stimulate e.g. muscle synthesis and increasing energy expenditure.

Thus an aspect of the present invention pertains to a) Beta-lactoglobulin or b) a nutritional composition comprising beta-lactoglobulin in an amount of at least 75% w/w relative to total protein in a therapeutically effective amount, for use in preventing and/or treating a metabolic disorder and/or muscle atrophy.

Yet an aspect of the invention pertains to a method of preventing and/or treating a metabolic disorder and/or muscle atrophy in a subject, the method comprising administering a therapeutically effective amount of a) beta-lactoglobulin or b) a nutritional composition comprising beta-lactoglobulin in an amount of at least 75% w/w relative to total protein to a subject in need thereof.

Another aspect of the invention pertains to use of a) beta-lactoglobulin or b) a nutritional composition comprising beta-lactoglobulin in an amount of at least 75% w/w relative to total protein for increasing the level of insulin and/or glucagon in the blood of a subject.

Yet another aspect of the invention pertains to a non-therapeutic use of a) beta-lactoglobulin or b) a nutritional composition comprising BLG in an amount of at least 75% w/w relative to total protein for one or more of:

stimulating or prolonging satiety or increasing satiation
reducing food intake
increasing energy expenditure
reducing adiposity
anabolic effect
muscle anabolic effect
in a subject Another aspect of the invention pertains to a non-therapeutic method for one or more of:

stimulating or prolonging satiety or increasing satiation
reducing food intake
increasing energy expenditure
reducing adiposity
anabolic effect
muscle anabolic effect, in a subject comprising administering a) beta-lactoglobulin or b) a nutritional composition comprising beta-lactoglobulin in an amount of at least 75% w/w relative to total protein.

Yet an aspect of the invention pertains to a method of increasing the level of insulin/and or glucagon in the blood of a subject, the method comprising administering to a subject a therapeutically effective amount of a) beta-lacto-globulin or b) a nutritional composition comprising BLG in an amount of at least 75% w/w relative to total protein.

The present inventors have for example made the surprising discovery that administration of BLG has an insulino-tropic effect in human subjects and therefore can be used to prevent and/or treat diabetes or prediabetes. This effect was unforeseen.

The present inventors have made the surprising discovery that administration of BLG according to the present invention has a superior effect of stimulating insulin release in humans relative to other milk proteins. It has thus surprisingly been found that BLG raises insulin and the glucose-dependent insulinotropic polypeptide (GIP) levels in a subject, which potentially could have beneficial glucose lowering effects in diabetic and pre-diabetic subjects. The insulin and GIP stimulatory effects are superior to those obtained by using similar doses of whey protein isolate (WPI) or casein as a protein source.

Thus, another aspect of the invention pertains to beta-lactoglobulin for use in preventing and/or treating diabetes or prediabetes in a subject.

Yet another aspect of the invention pertains to a nutritional composition for use in preventing and/or treating diabetes or prediabetes in a subject, wherein the nutritional composition comprises a total amount of protein of at least 1.0 wt % relative to the weight of the nutritional composition, wherein at least 75 wt % of the protein is beta-lactoglobulin.

BRIEF DESCRIPTION OF THE FIGURES

FIG. 7 illustrates total plasma amino acid concentrations after interventions with BLG (black dot), CAS (white dot) and WHE (black triangle) with SEM (error bars). NS=No significant difference between interventions (p>0.05). Repeated measures mixed modeling on iAUC was used to compare interventions.

FIG. 23a+b illustrates the mean interstitial fluid glucose (ISF-glucose) curves by intervention (black: BLG, dark grey: WPI, light grey: CTR) and their difference as percentage, both with 95% CIs based on a mixed effect model.

DETAILED DESCRIPTION

Figure 1:
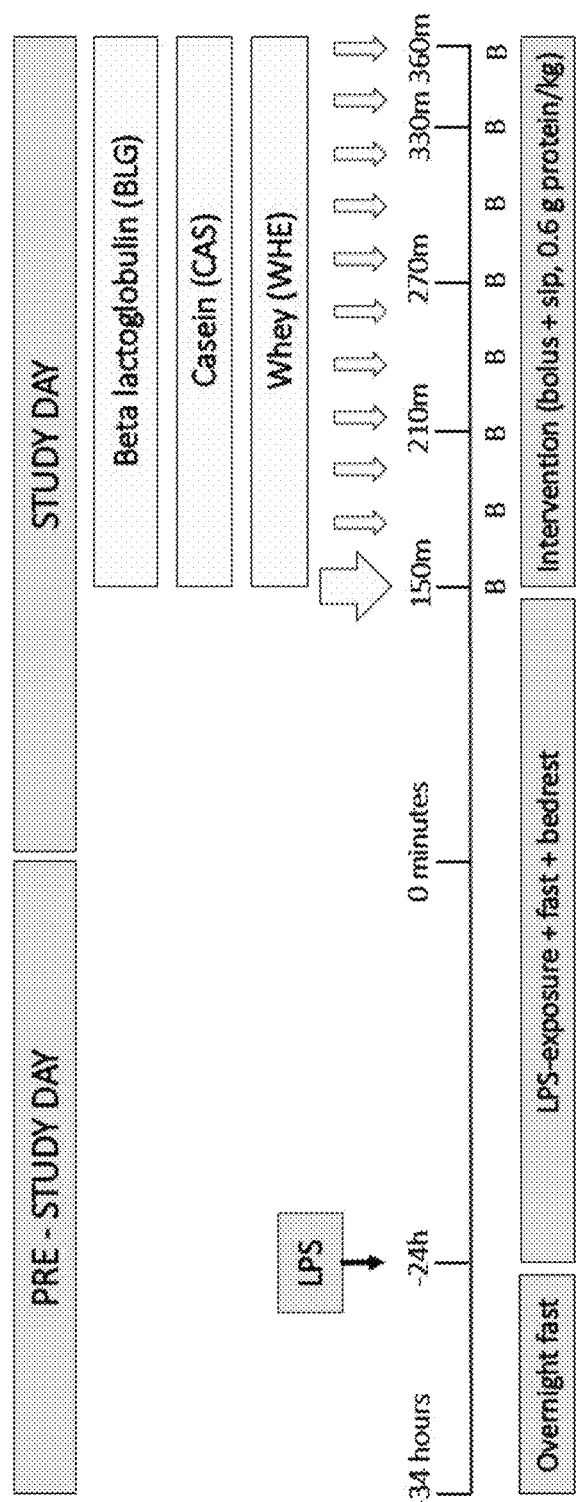
FIG. 1 illustrates the catabolic model (pre-study day; LPS-exposure+fast+bed rest) and the three interventions beta-lactoglobulin, casein and whey (study day), orally administered as a bolus+sip regime (arrows) together with time points for blood sampling (B).

The present inventors have made the surprising discovery that administration of BLG or a nutritional composition comprising BLG in a purity of at least 75% relative to total protein has both an insulinotropic effect and a glucagonotropic effect in human subjects. The insulin and glucagon stimulatory effects are superior to those obtained by using similar doses of whey protein isolate (WPI) as a protein source.

This opens up for using BLG-enriched products to prevent or treat disorders relating to imbalances of these hormones related to metabolic disorders and/or muscle atrophy or for therapeutic or non-therapeutic treatment to stimulate e.g. muscle synthesis and increasing energy expenditure and reducing adiposity.

An aspect of the invention pertains to a) Beta-lactoglobulin or b) a nutritional composition comprising beta-lactoglobulin in an amount of at least 75% w/w relative to total protein in a therapeutically effective amount, for use in preventing and/or treating a metabolic disorder and/or muscle atrophy.

The inventors have found that BLG has superior insulinotropic and glucagonotropic effects relative to other milk proteins and BLG can therefore advantageously be used to prevent and/or treat metabolic disorder and/or muscle atrophy. See FIGS. 11 and 12 as well as example 4 and 5.

Insulin is known to effectively damper lipid concentrations in the blood stream as insulin increase the uptake of lipids in the muscles, while glucagon have a positive impact on energy expenditure and inhibit appetite. Administration of BLG to a subject having metabolic disorder will therefore be beneficial, as this will result in an increase in the circulating glucagon and insulin concentrations.

The inventors have shown that BLG intake increases the concentration of the circulating insulin, glucagon and specific amino acids such as leucine, phenylalanine, methionine, proline, tyrosine, aspartate, glutamate and lysine. The combination of insulin and especially leucine has shown particularly effective anabolic effects in muscles and may therefore be useful for preserving or building up muscle during condition such as cancer, cachexia, sarcopenia, inflammatory disease, following gastric bypass/sleeve and malnutrition, and also in the general population (including athletes) where maintenance or accretion of muscle tissue/mass is desired.

In the context of the present invention, the term "metabolic disorder" pertains to a condition, wherein abnormal chemical reactions in the body alter the normal metabolic process. Examples of metabolic disorders are metabolic syndrome, obesity, dyslipidemia, hepatic steatosis, diabetes, prediabetes, and glucose intolerance.

In the context of the present invention, the term "muscle atrophy" pertains to a condition of loss of skeletal muscle mass that can be caused by for example sarcopenia, cachexia, endocrinopathies, malnutrition, immobility and/or reduced physical activity, side effect of medication, anabolic resistance, insulin resistance, eating disorders and hypoalbuminaemia.

In the context of the present invention, the term "beta-lactoglobulin" or "BLG" pertains to beta-lactoglobulin from mammal species, e.g. in native, unfolded and/or glycosylated forms and includes the naturally occurring genetic variants. The term furthermore includes aggregated BLG, precipitated BLG and crystalline BLG. When referring to the amount of BLG, reference is made to the total amount of BLG including aggregated BLG. The total amount of BLG is determined according to Example 1.18. The term "aggregated BLG" pertains to BLG which is at least partially unfolded and which, furthermore, has aggregated with other denatured BLG molecules and/or other denatured whey proteins, typically by means of hydrophobic interactions and/or covalent bonds.

The term BLG pertains to non-hydrolysed BLG i.e. full length mature BLG as present in milk, which can be determined using gel filtration and/or gel electrophoresis. The term BLG thus does not include peptide fragments of BLG.

BLG is the most predominant protein in bovine whey and milk serum and exists in several genetic variants, the main ones in cow milk being labelled A and B. The amino acid sequences of the genetic variants of BLG are well-known to the skilled person. The amino acid sequence of the mature bovine BLG variant B is for example found under accession number: P02754 (updated 16 Oct. 2019) in uniprot.org (amino acids 17-178).

BLG is a lipocalin protein, and can bind many hydrophobic molecules, suggesting a role in their transport. BLG has also been shown to be able to bind iron via siderophores and might have a role in combating pathogens. A homologue of BLG is lacking in human breast milk.

BLG is a relatively small protein of approx. 162 amino acid residues with a molecular weight of approx. 18.3-18.4 kDa. Under physiological conditions, it is predominantly dimeric, but dissociates to a monomer below about pH 3, preserving its native state as determined using Nuclear Magnetic Resonance spectroscopy. Conversely, BLG also occurs in tetrameric, octameric and other multimeric aggregation forms under a variety of natural conditions.

In the context of the present invention, the term "non-aggregated beta-lactoglobulin" or "non-aggregated BLG" also pertains to beta-lactoglobulin from mammal species, e.g. in native, unfolded and/or glycosylated forms and includes the naturally occurring genetic variants. However, the term does not include aggregated BLG, precipitated BLG or crystallised BLG. The amount or concentration of non-aggregated BLG is determined according to Example 1.4.

The percentage of non-aggregated BLG relative to total BLG is determined by calculate ($m_{total\ BLG}$-$m_{non-aggregate\ BLG}$)/$m_{total\ BLG}$*100%. $m_{total\ BLG}$ is the concentration or amount of BLG determined according to Example 1.18 and $m_{non-aggregated}$ BLG is the concentration or amount of non-aggregated BLG determined according to Example 1.4.

In the context of the present invention, the term "crystal" pertains to a solid material whose constituents (such as atoms, molecules or ions) are arranged in a highly ordered microscopic structure, forming a crystal lattice that extends in all directions.

Figure 18:
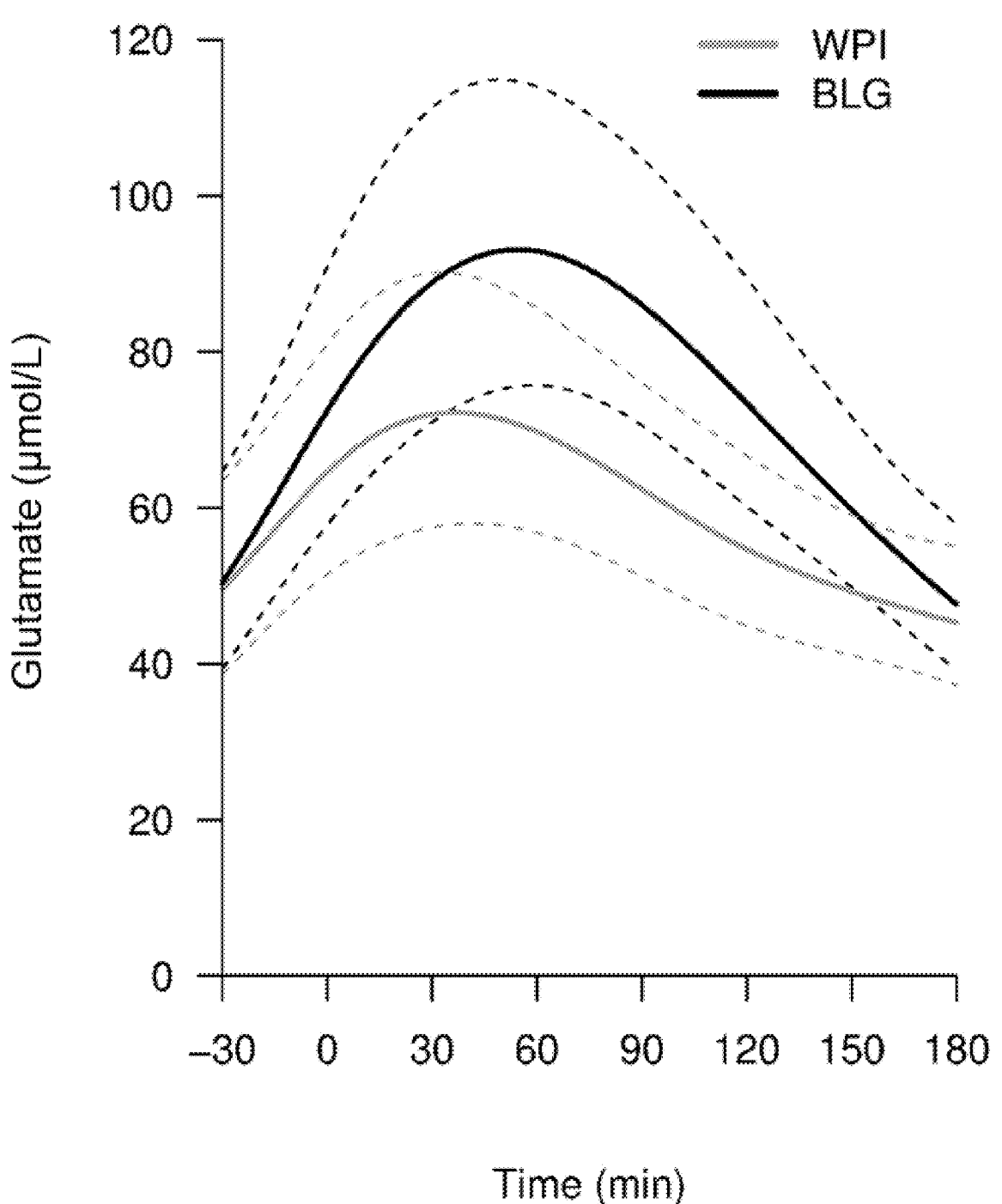
FIG. 18a+b illustrates the mean plasma glutamate curves by intervention (black: BLG, grey: WPI) and their difference as percentage, both with 95% CIs based on a mixed effect model.
FIG. 18c illustrates the individual incremental area under the curve (iAUC) with a bar plot that shows the mean±standard deviation.
Figure 18:
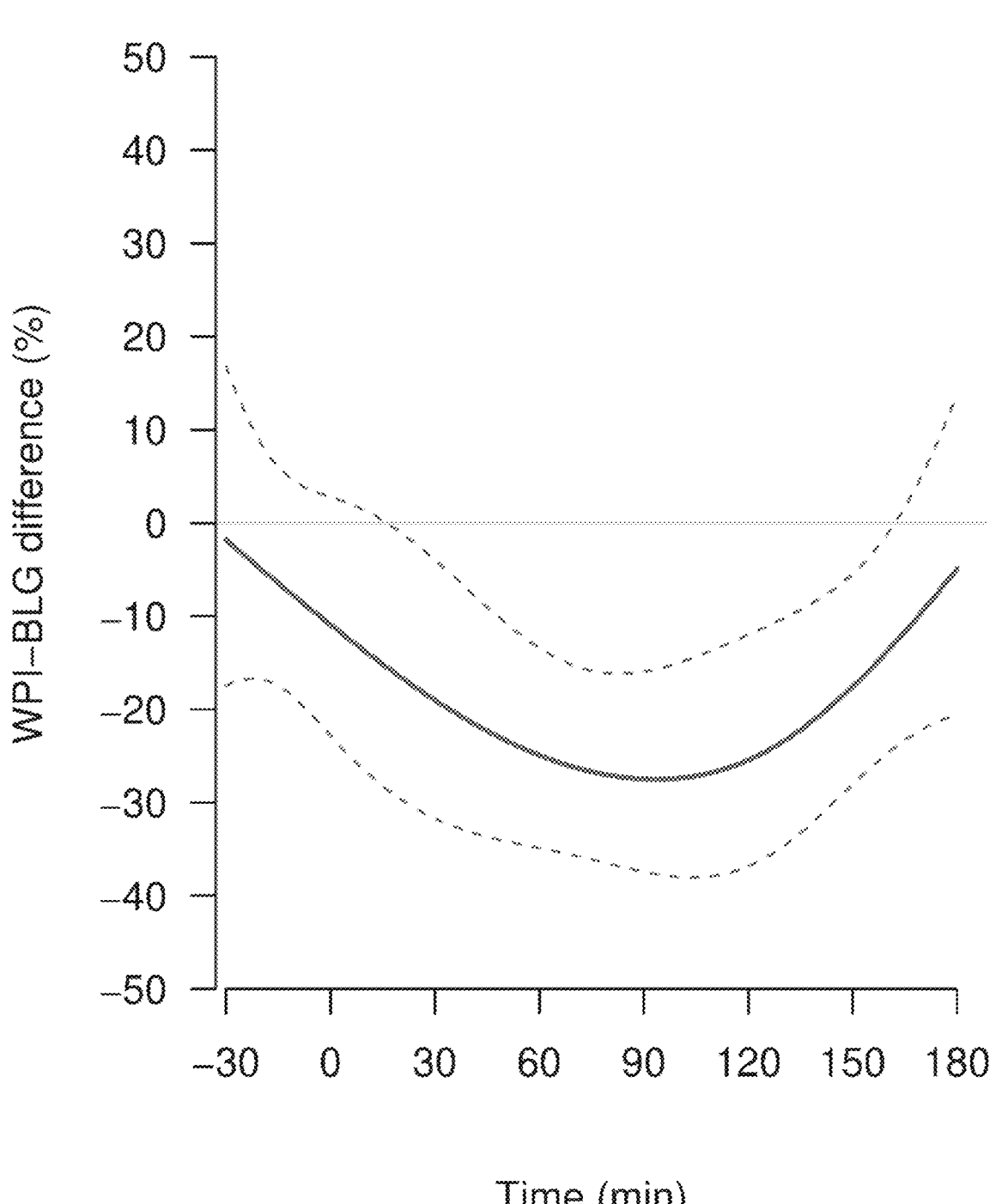
Figure 18:
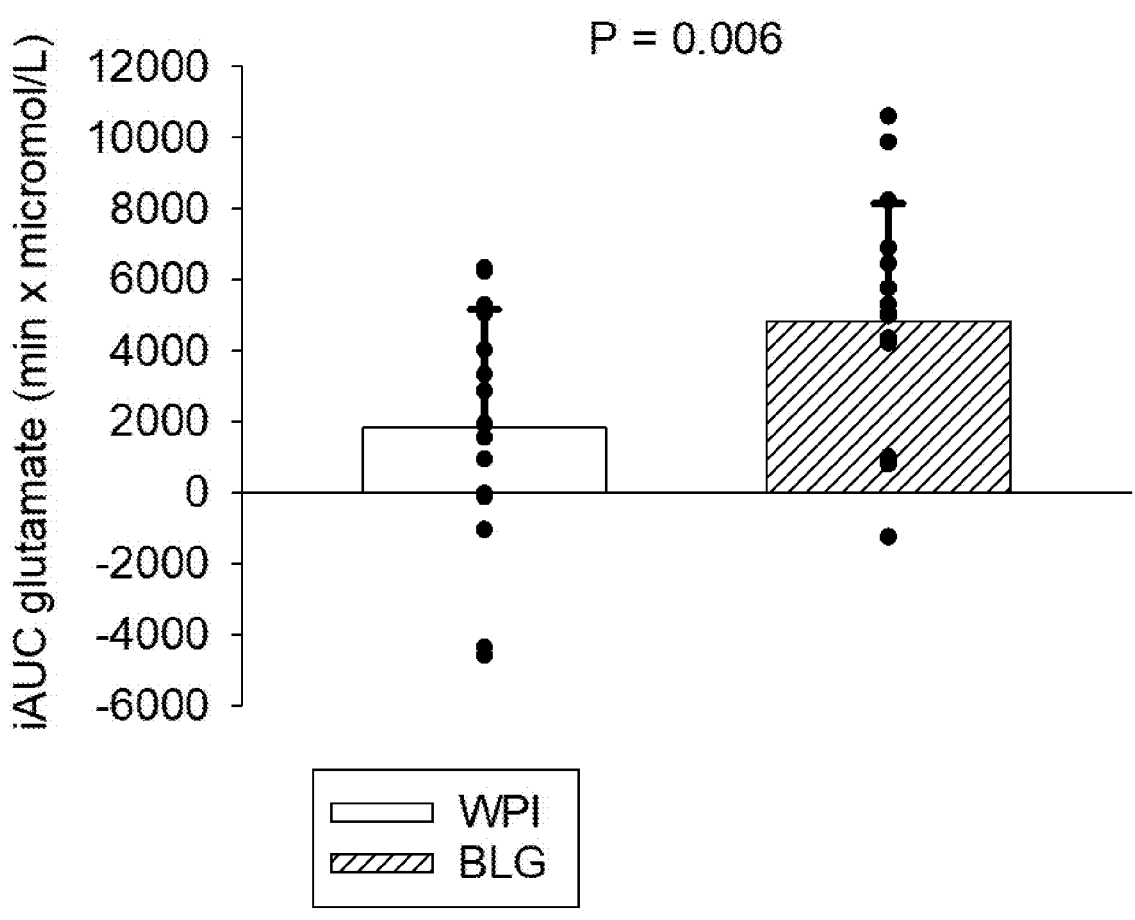
Figure 19:
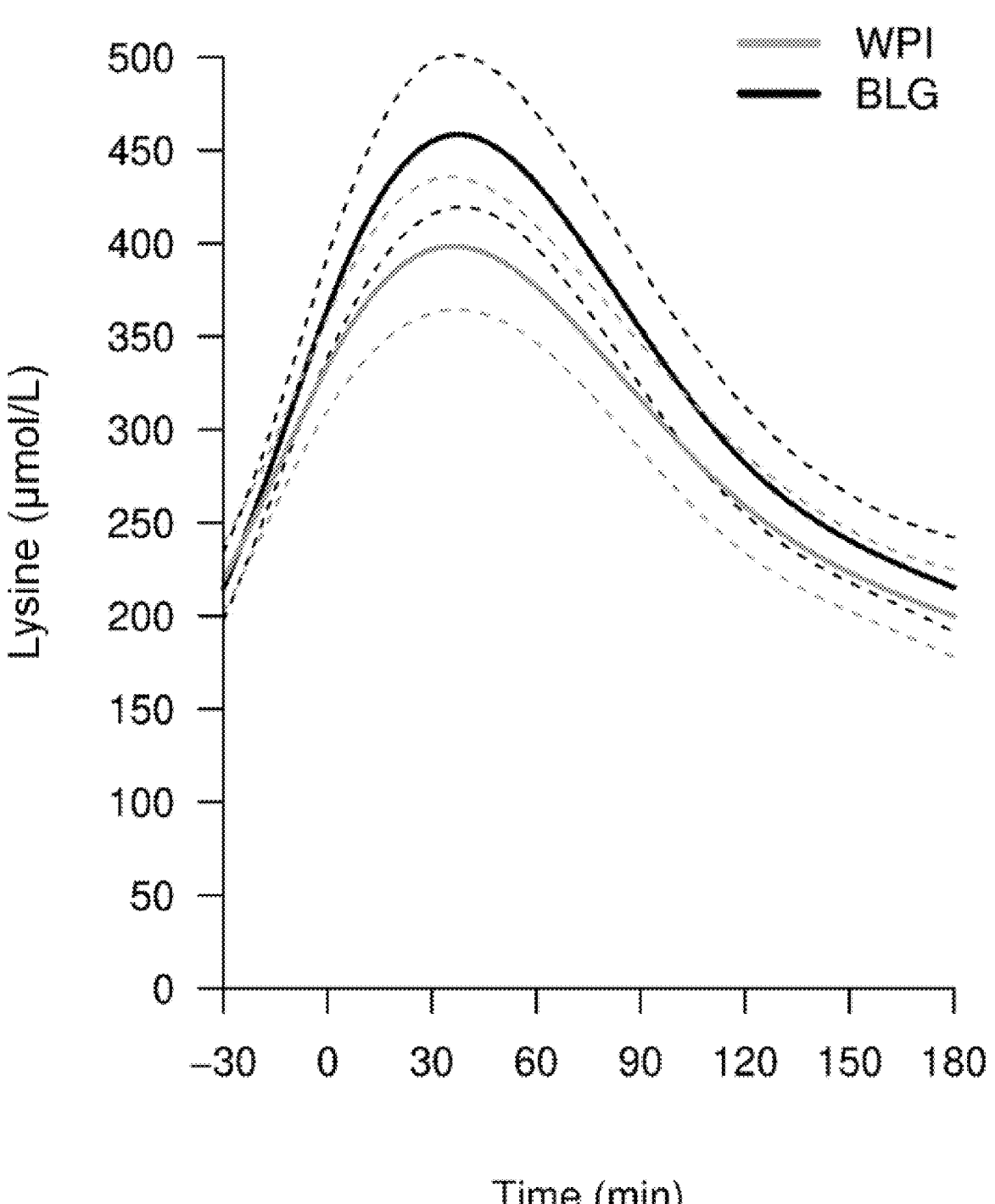
FIG. 19a+b illustrates the mean plasma lysine curves by intervention (black: BLG, grey: WPI) and their difference as percentage, both with 95% CIs based on a mixed effect model.
FIG. 19c illustrates the individual incremental area under the curve (iAUC) with a bar plot that shows the mean±standard deviation.
Figure 19:
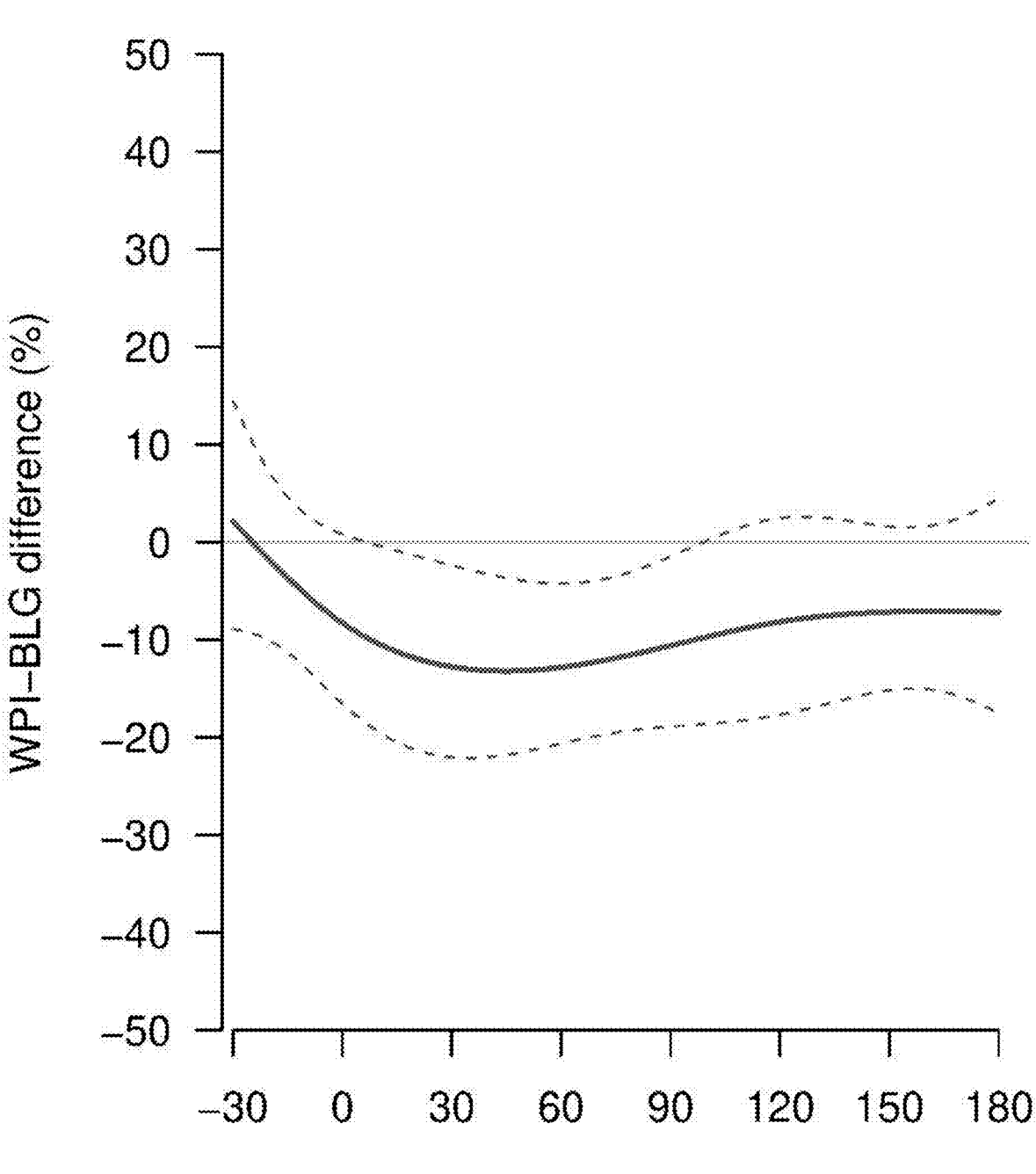
Figure 19:
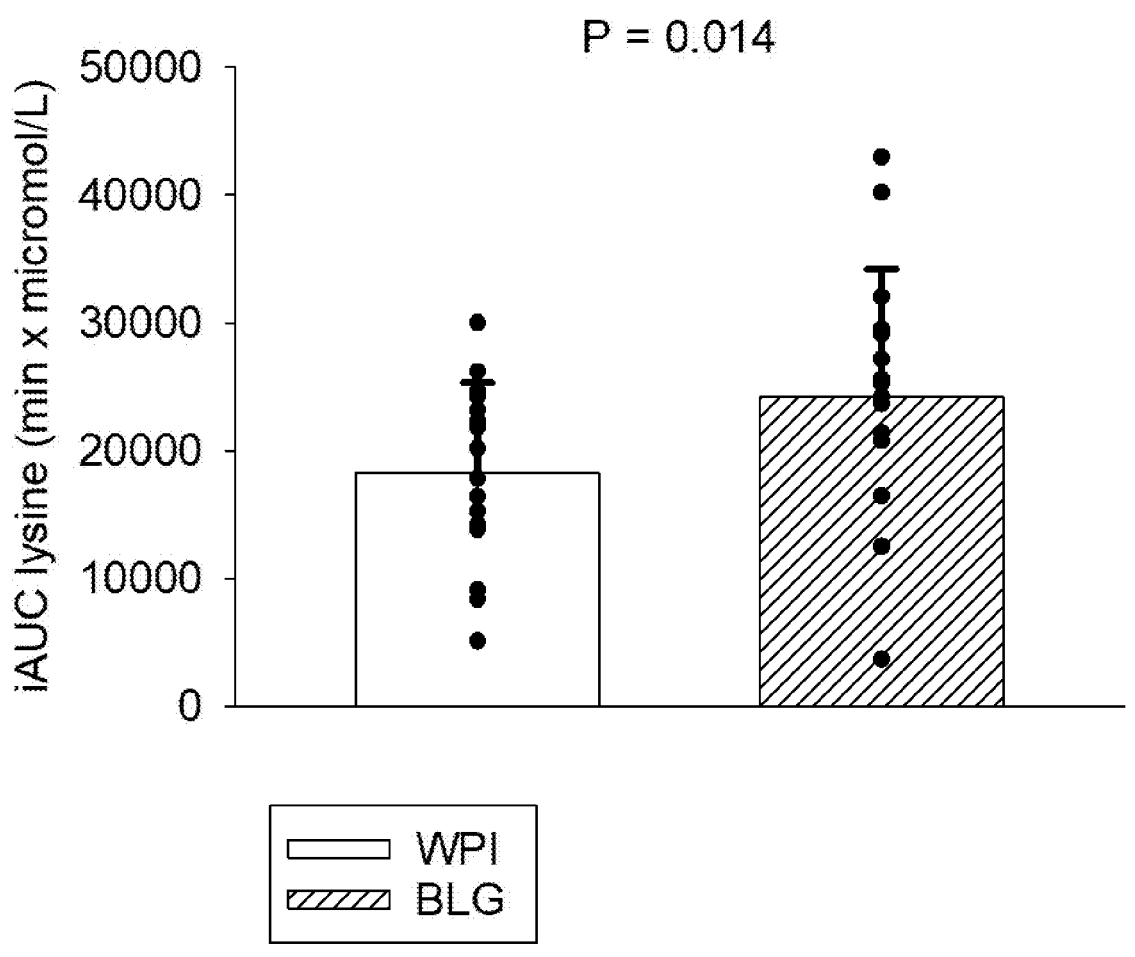
Figure 20:
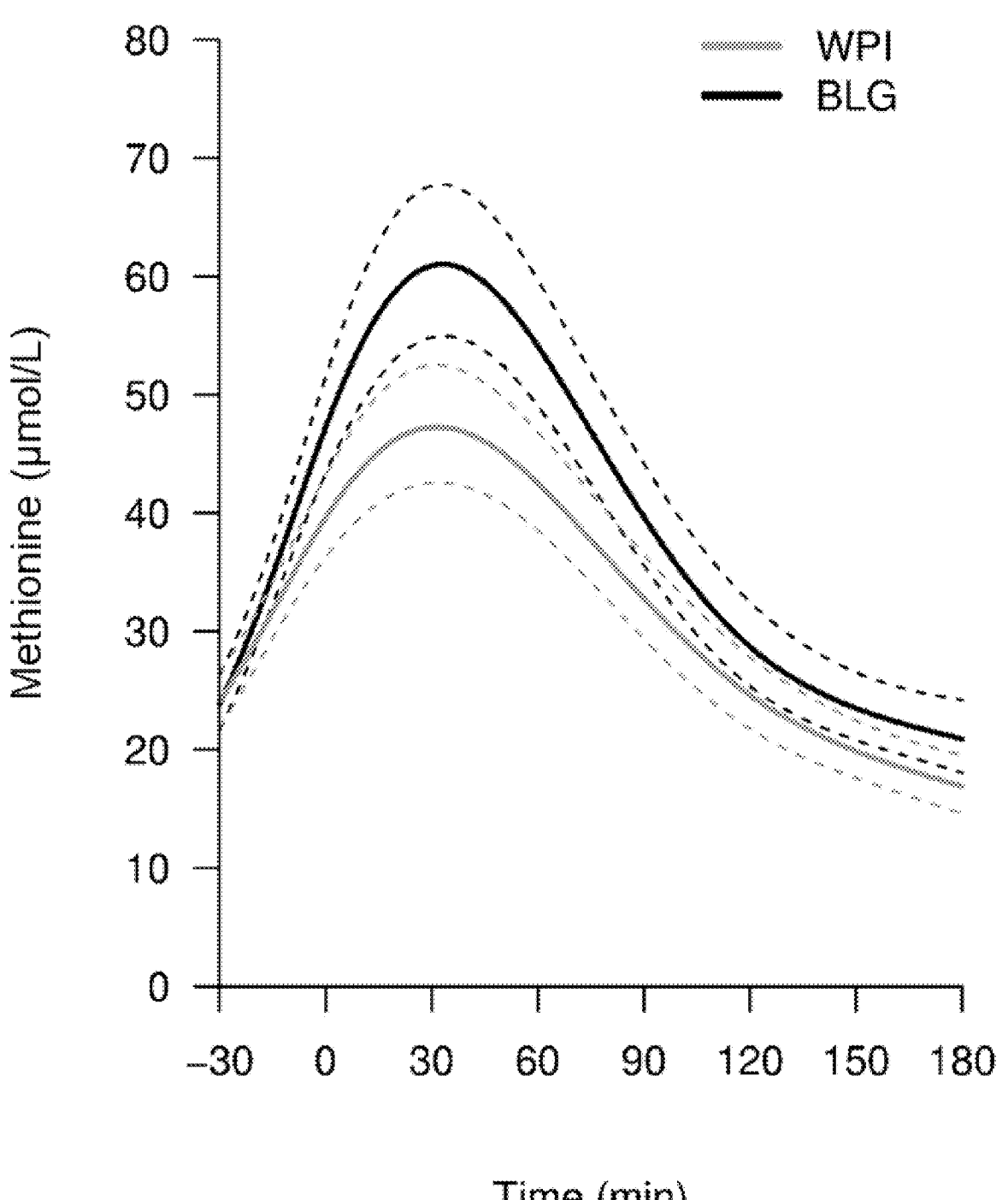
FIG. 20a+b illustrates the mean plasma methionine curves by intervention (black: BLG, grey: WPI) and their difference as percentage, both with 95% CIs based on a mixed effect model.
FIG. 20c illustrates the individual incremental area under the curve (iAUC) with a bar plot that shows the mean±standard deviation.
Figure 20:
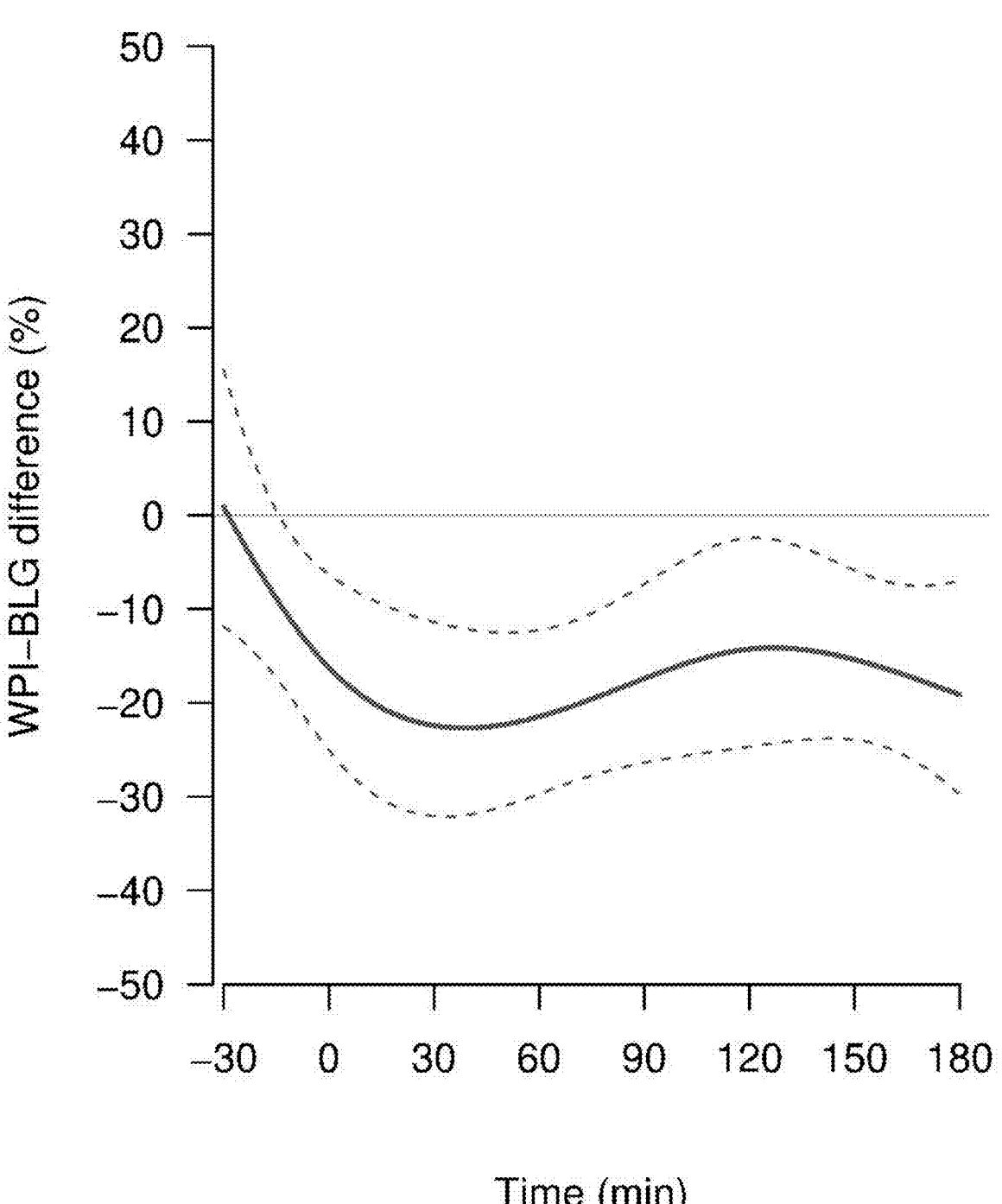
Figure 20:
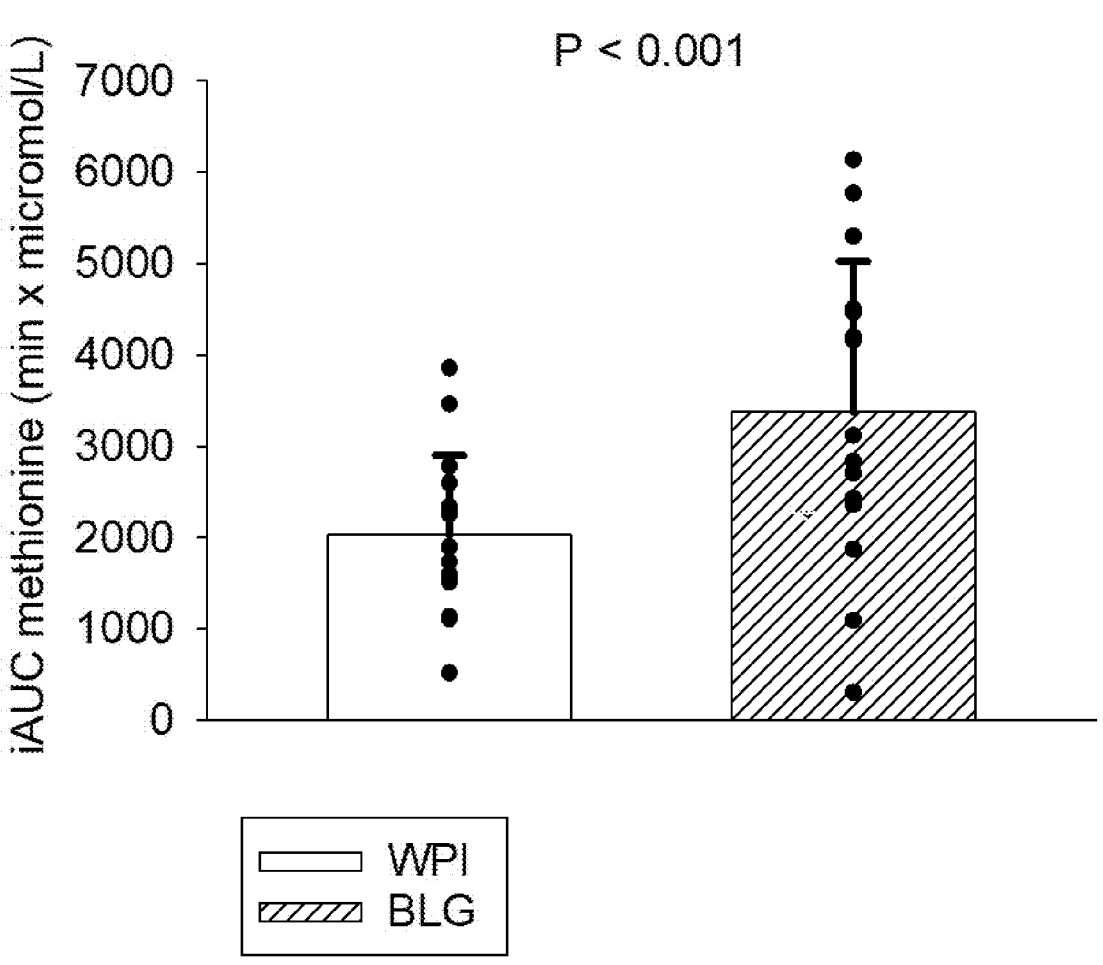
Figure 21:
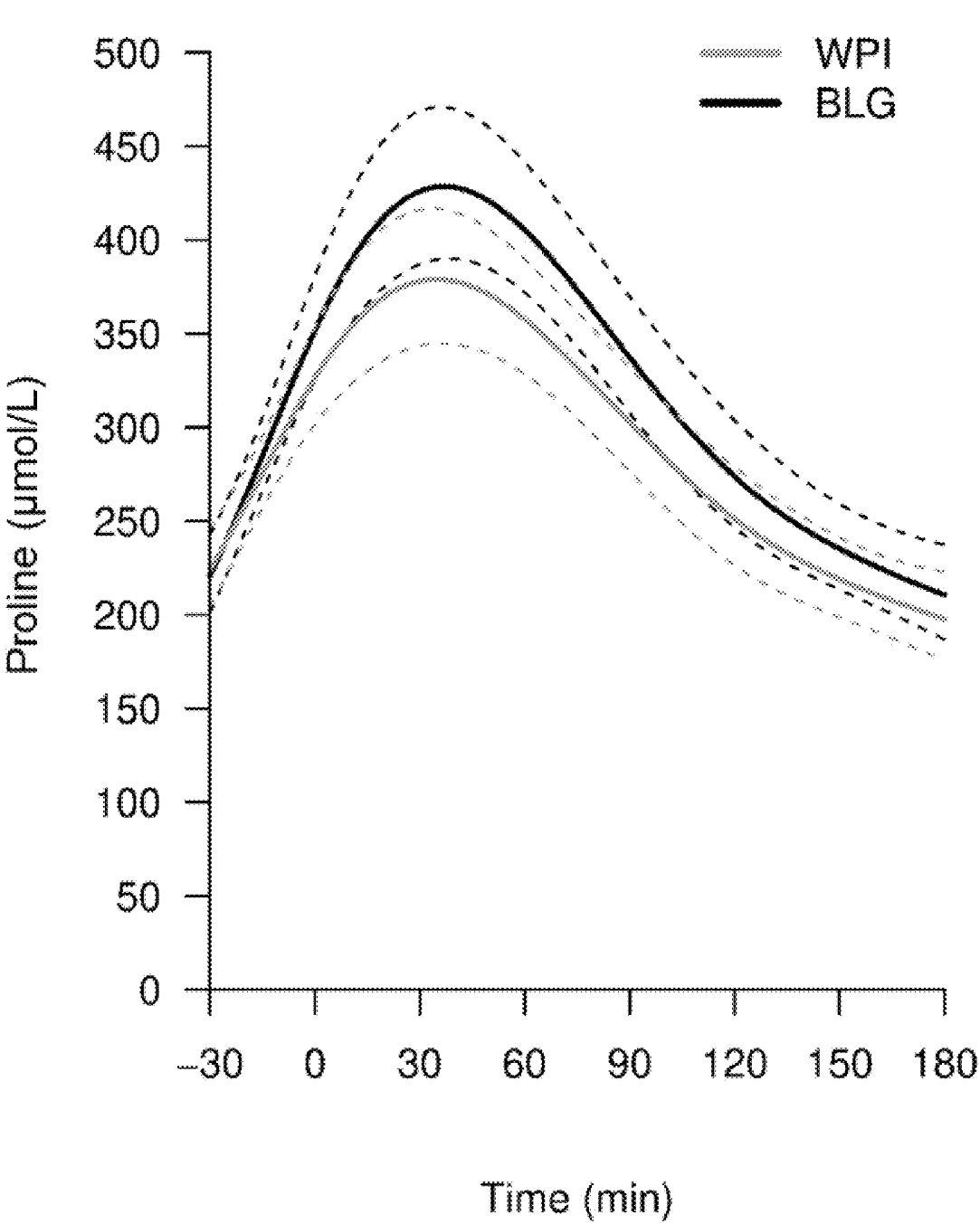
FIG. 21a+b illustrates the mean plasma proline curves by intervention (black: BLG, grey: WPI) and their difference as percentage, both with 95% CIs based on a mixed effect model.
FIG. 21c illustrates the individual incremental area under the curve (iAUC) with a bar plot that shows the mean±standard deviation.
Figure 21:
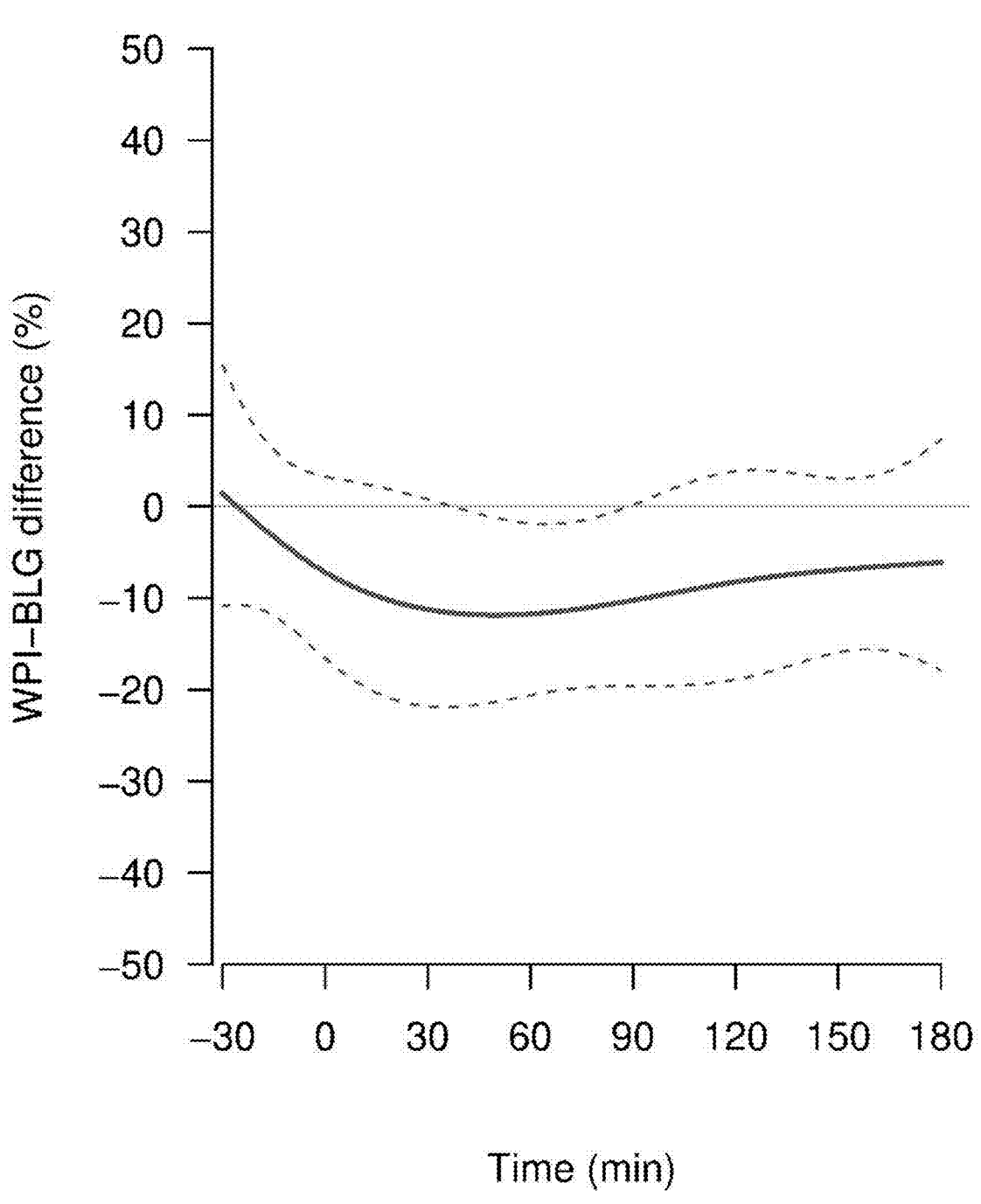
Figure 21:
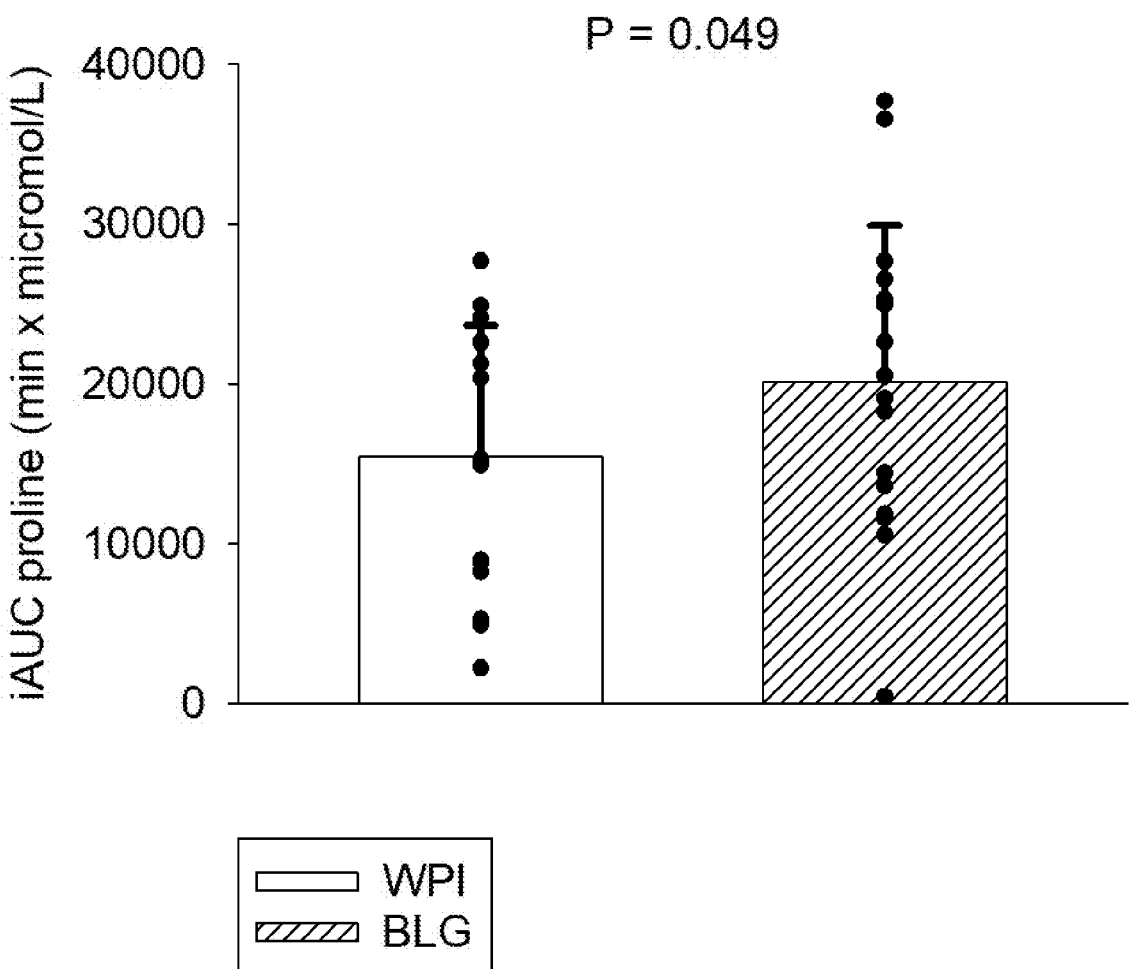
Figure 22:
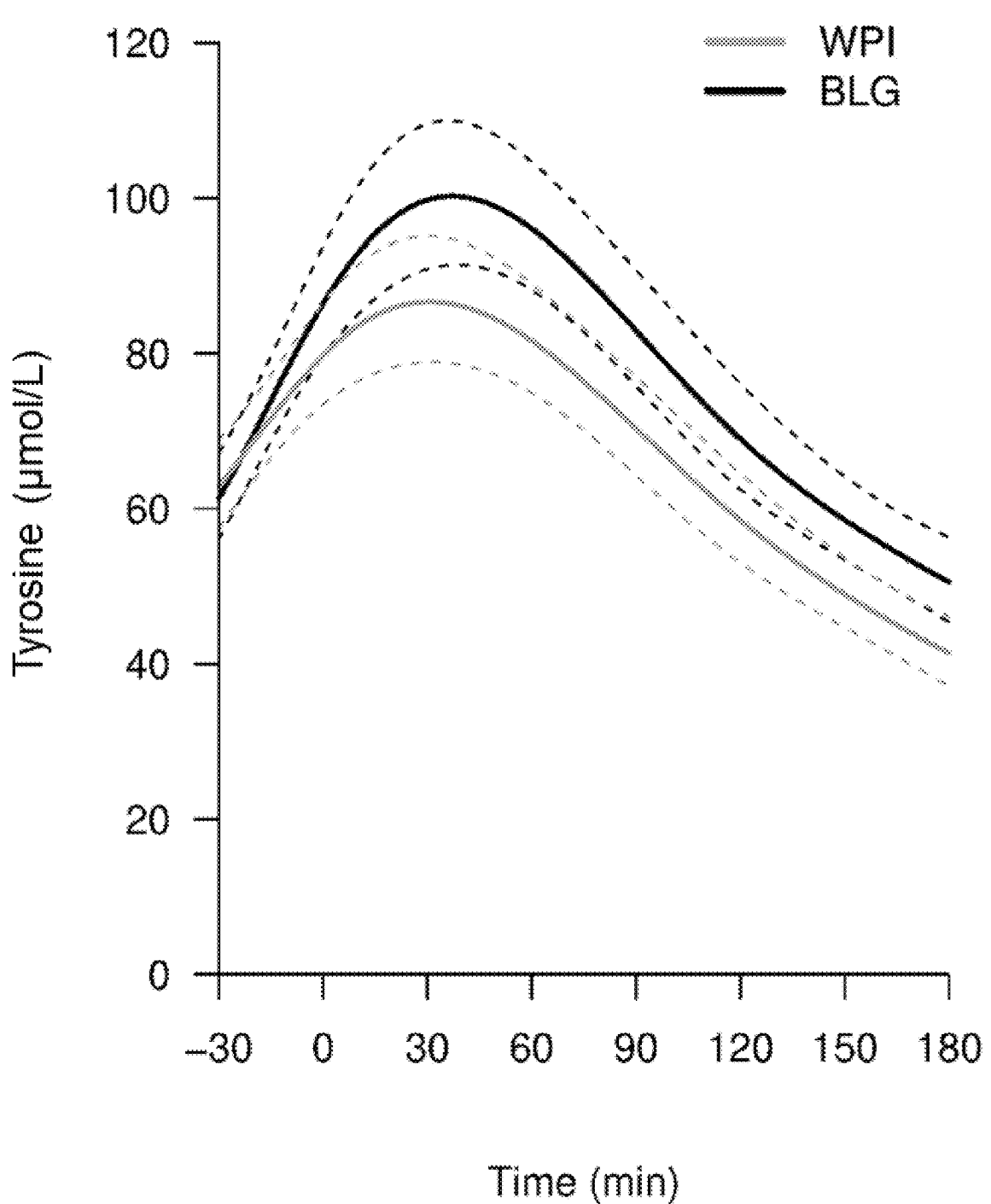
FIG. 22a+b illustrates the mean plasma tyrosine curves by intervention (black: BLG, grey: WPI) and their difference as percentage, both with 95% CIs based on a mixed effect model.
FIG. 22c illustrates the individual incremental area under the curve (iAUC) with a bar plot that shows the mean±standard deviation.
Figure 22:
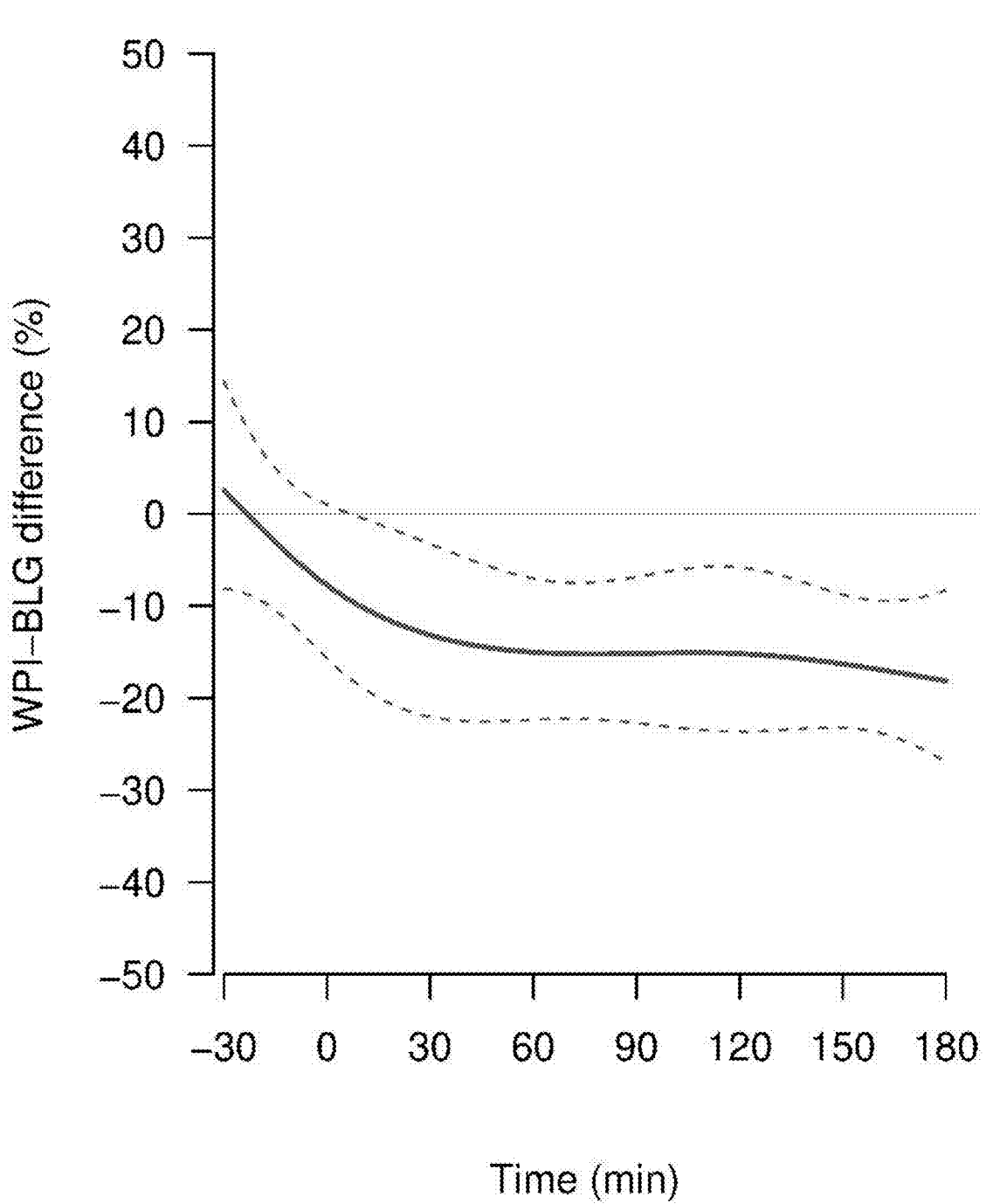
Figure 22:
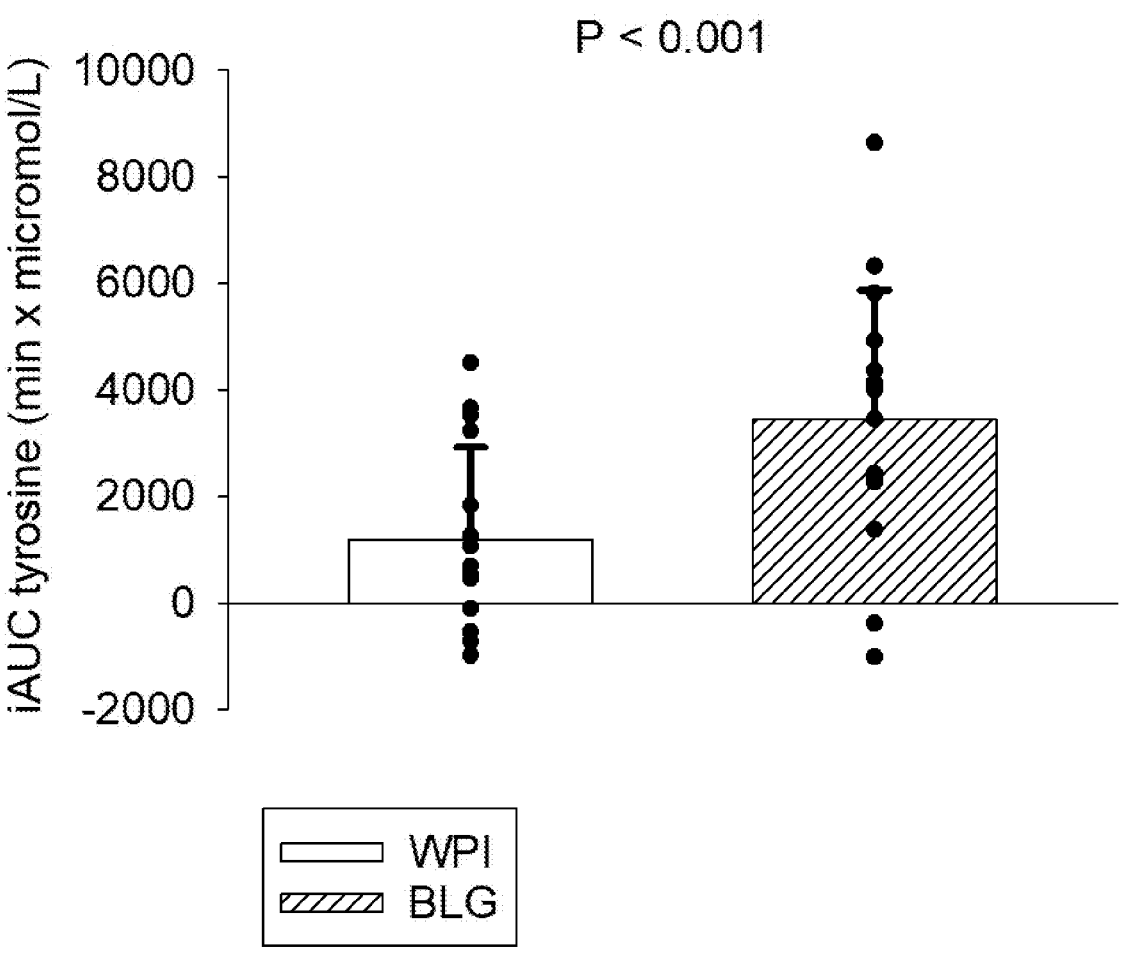

In the context of the present invention, the term "BLG crystal" pertains to protein crystals that primarily contain non-aggregated and preferably native BLG arranged in a highly ordered microscopic structure, forming a crystal lattice that extends in all directions. The BLG crystals may e.g. be monolithic or polycrystalline and may e.g. be intact crystals, fragments of crystals, or a combination thereof. Fragments of crystals are e.g. formed when intact crystals are subjected to mechanical shear during processing. Fragments of crystals also have the highly ordered microscopic structure of crystal but may lack the even surface and/or even edges or corners of an intact crystal. See e.g. FIG. 18 of PCT application no. PCT/EP2017/084553 for an example of many intact BLG crystals and FIG. 13 PCT application no. PCT/EP2017/084553 for an example of fragments of BLG crystals. In both cases, the BLG crystal or crystal fragments can be identified visually as well-defined, compact and coherent structures using light microscopy. BLG crystal or crystal fragments are often at least partially transparent. Protein crystals are furthermore known to be birefringent and this optical property can be used to identify unknown particles having a crystal structure. Non-crystalline BLG aggregates, on the other hand, often appear as poorly defined, non-transparent, and as open or porous lumps of irregular size.

In the context of the present invention, the term "crystallise" pertains to the formation of protein crystals. Crystallisation may e.g. happen spontaneously or be initiated by the addition of crystallisation seeds.

In the context of the present invention, the term "preventing", "prevent" or "prevention" pertains to postponing, slowing or avoiding development of a condition such as metabolic disorder such as diabetes or prediabetes or muscle atrophy in a subject.

In the context of the present invention, the term "treating", "treatment" and "treat" pertains to alleviating, curing or eliminating a condition such as metabolic disorder such as diabetes or prediabetes or muscle atrophy in a subject. Alleviating may result in reduced medication dosage of for example glucose-lowering medicaments.

In some preferred embodiments of the invention, the metabolic disorder is selected from one or more of: metabolic syndrome, obesity, dyslipidemia, hepatic steatosis, diabetes, prediabetes, and glucose intolerance.

In the context of the present invention, "metabolic syndrome" is a complex disorder associated with increased risk of cardiovascular disease and type 2 diabetes. Metabolic syndrome is linked to increased arterial blood pressure, elevated fasting glucose and insulin resistance, overweight (e.g., body mass index (BMI) greater or equal to 25 kg/m2), abdominal obesity, habitual physical inactivity, hypertension (e.g., greater or equal to 140/90 mmHg in adults, HDL cholesterol greater or equal to 35 mg/dl; triglyceride levels greater or equal to 250 mg/dl. (Indian J Endocrinol Metab. 2012 January-February; 16(1): 7-12. Doi:10.41033/2230-821.91175. Changing definitions of metabolic syndrome, Rakesh M. Parikh and Viswanathan Mohan1).

In the context of the present invention, the term "obesity" pertains to a medical condition in which excess body fat has accumulated to an extent that it may have a negative effect on certain health conditions or increased mortality. Humans are generally considered obese when their body mass index (BMI) is over 30 kg/m$^2$. BMI is a measurement, which is obtained by dividing a person's weight by the square of the person's height.

In the context of the present invention, the term "overweight" is defined for an adult when the BMI is in the range of 25-30 kg/m$^2$.

In the context of the present invention, the term "dyslipidemia" pertains to a condition where the person has an abnormal amount of lipids (e.g. triglycerides, cholesterol and/or fat phospholipids) in the blood. When only cholesterol levels are high or low, this is referred to as hypercholesterolemia or hypocholesterolemia.

In the context of the present invention, the term "hypercholesterolemia" thus pertains to a condition of the presence of high levels of non-HDL cholesterol and LDL cholesterol in the blood.

HDL means high density lipoprotein. "Non-HDL cholesterol" is often referred to as the bad cholesterol as it refers to a person's total cholesterol value minus the HDL cholesterol. LDL cholesterol means low density lipoprotein.

Hypercholesterolemia is thus a form of hyperlipidemia, high blood lipids, and hyperlipoproteinemia (elevated levels of lipoproteins in the blood). Elevated levels of non-HDL cholesterol and LDL in the blood may be a consequence of diet, obesity, inherited (genetic) diseases (such as LDL receptor mutations in familial hypercholesterolemia), or the presence of other diseases such as type 2 diabetes and an underactive thyroid.

In the context of the present invention, the term "hepatic steatosis" or "fatty liver disease" refers to a condition where excess fat builds up in the liver. Often there are no or few symptoms. Occasionally there may be tiredness or pain in the upper right side of the abdomen. Complications may include cirrhosis, liver cancer, and esophageal varices.

There are two types of fatty liver disease: non-alcoholic fatty liver disease (NAFLD) and alcoholic liver disease. NAFLD is made up of simple fatty liver and non-alcoholic steatohepatitis (NASH). The primary risks include alcohol, type 2 diabetes, and obesity. Other risk factors include certain medications such as glucocorticoids, and hepatitis C.

In the context of the present invention, the term "hyper-triglyceridemia" pertains to high (-hyper) blood levels (-emia) of triglycerides, the most abundant fatty molecule in most organisms. Elevated levels of triglycerides are associated with atherosclerosis, even in the absence of hypercho-lesterolemia (high cholesterol levels), and predispose to cardiovascular disease. Very high triglyceride levels also increase the risk of acute pancreatitis. Hypertriglyceridemia itself is usually symptomless, although high levels may be associated with skin lesions known as xanthomas.

In the context of the present invention, the term "glucose intolerance" (GI) pertains to dysglycemia that comprises both prediabetes and diabetes. It includes the conditions of impaired fasting glucose (IFG), impaired glucose tolerance (IGT), gestational diabetes mellitus (GDM) and diabetes mellitus (DM).

In the context of the present invention the term "diabetes" or "diabetes mellitus" pertains to a chronic disease that occurs either when the pancreatic beta cells do not produce enough insulin or when the body cannot effectively use the insulin it produces.

Using WHO's definition of diabetes; a human is diagnosed with diabetes either when:

1) the fasting glucose is ≥126 mg/dL (7.0 mmol/L) or
2) 2 hour plasma glucose (PG)≥200 mg/dL (11.1 mmol/L) during oral glucose tolerance test (OGTT). The test should be performed as described by the WHO, using a glucose load containing the equivalent of 75 g anhy-drous glucose dissolved in water or
3) plasma hemoglobin A1c (HbA1C)≥6.5% (48 mmol/mol). The test should be performed in a laboratory using method that is "National Glycohemoglobin Stan-dardization Program" (NGSP) certified and standard-ized to the Diabetes Control and Complications Trial (DCCT) assay or
4) in a patient with classic symptoms of hyperglycemia or hyperglycemic crisis, a random plasma glucose≥200 mg/dl (11.1 mmol/L).

See Diabetes Care. 2010 January; 33(Suppl 1): S62-S69. Diagnosis and Classification of Diabetes Mellitus. American Diabetes Association. doi: 10.2337/dc10-5062.

In the context of the present invention, "fasting" is defined as no caloric intake for at least 8 hours.

A persistently high level of blood glucose is referred to as hyperglycemia, while low levels are referred to as hypogly-cemia. Diabetes mellitus is characterized by persistent hyperglycemia from any of several causes, and is the most prominent disease related to failure of blood sugar regula-tion.

Type 1 diabetes accounts for only 5-10% of patients with diabetes. Type 1 diabetes results from a cellular mediated autoimmune destruction of the beta-cells of the pancreas. The rate of beta-cell destruction is quite variable, being rapid in some individuals (mainly infants and children) and slow in others (mainly adults). Particularly adults may retain residual β-cell function sufficient to prevent ketoacidosis for many years. A way to determine whether a subject has a preserved beta-cell function is by measuring the subject's blood C-peptide level.

A non-insulin treated subject (measured after an overnight fast) having a plasma C-peptide level above the lower reference level of 370 μmol/L has at least some preserved beta-cell function.

Administration of BLG to a subject having type 1 diabe-tes, but with some preserved beta cell function, will be beneficial as this will result in an increase in the circulating GIP and/or GLP-1 and insulin concentrations.

Type 2 diabetes is the most common type of diabetes and it accounts for 90-95% of patients with diabetes. The risk of developing type 2 diabetes increases with age, obesity, and lack of physical activity. It occurs more frequently in women with prior Gestational diabetes (GDM) and in individuals with hypertension or dyslipidemia, and its frequency varies in different racial/ethnic subgroups. It is often associated with a strong genetic predisposition. Hyperglycemia and type 2 diabetes stem from an imbalance between insulin sensitivity and beta cell function. Thus, low beta cell func-tion and/or low insulin sensitivity leads to high blood glucose concentrations, which may be effectively avoided by improving either insulin secretion or insulin sensitivity.

Gestationel diabetes (GDM) develops in 4-5% off all pregnancies in Denmark. Most of the time, this type of diabetes is transient. However, it is well-known that GDM is associated with a substantial risk of developing type 2 diabetes in the years following the pregnancy.

Latent autoimmune diabetes in adulthood (LADA) is a diabetes subtype which is primarily caused by decreasing beta cell function (e.g. low C-peptide) and treatment may initially include usual medicaments for type 2 diabetes for a certain amount of time, after which exogenous insulin treatment will become essential as it is for type 1 diabetes subjects. This has lead to the term type 1.5 diabetes.

In the context of the present invention, the term "predia-betes" pertains to a condition associated with higher risk of developing diabetes later in life. A subject with prediabetes is typically insulin resistant, has impaired glucose tolerance, has metabolic syndrome, is obese or is predisposed (e.g. by family history/genetics; carrying alleles that result in a higher occurrence of diabetes than in the average population or have parents or siblings with diabetes).

Without lifestyle changes, a subject with prediabetes is at increased risk of developing type 2 diabetes.

In some preferred embodiments of the present invention the metabolic disorder is metabolic syndrome, obesity and/or dyslipidemia.

Insulin is known to effectively damper lipid concentra-tions in the blood stream, as insulin increases the uptake of lipids in the muscles. While glucagon has shown to increase energy expenditure and inhibit appetite. As we surprisingly found that BLG increases the concentrations of both insulin and glucagon we trust that BLG advantageously has a potential in being effective in the treatment of metabolic syndrome, obesity and/or dyslipidemia.

In some preferred embodiments of the present invention the metabolic disorder is metabolic syndrome.

In some preferred embodiments of the present invention the metabolic disorder is obesity.

Further to this, it is known that single analogues of glucagon-like peptide-1 (GLP-1), bi-agonists of GLP-1 and glucagon and tri-agonists of GIP, glucagon-like peptide-1 (GLP-1) and glucagon have a potential for being used for treating obesity.

As we surprisingly found that BLG increases the concen-trations of all these three hormones (GIP, GLP-1 and gluca-gon) we trust that BLG advantageously has a potential in being effective in the treatment of obesity.

In some preferred embodiments of the present invention the metabolic disorder is dyslipidemia.

In some preferred embodiments of the present invention the metabolic disorder is diabetes and/or prediabetes.

In some preferred embodiments of the present invention muscle atrophy is selected from one or more of: sarcopenia, cachexia, endocrinopathies, malnutrition, immobility and/or reduced physical activity, side effect of medication, anabolic resistance, insulin resistance, eating disorders such as anorexia nervosa and/or bulimi, hypoalbuminaemia, malabsorption of nutrients such as protein due to for example gastric bypass, sleeve gastrectomy, short bowel disease, Inflammatory Bowel Disease such as Mb Crohn and/or colitis ulcerosa and/or cirrhosis.

In the context of the present invention, the term "sarcopenia", pertains to a type of muscle atrophy, muscle loss, that occurs with aging and/or immobility. It is characterized by the degenerative loss of skeletal muscle mass, quality, and strength. There are many proposed causes of sarcopenia and it is likely the result of multiple interacting factors. Understanding of the causes of sarcopenia is incomplete.

Potential causes of sarcopenia are for example changes in hormones, immobility, age-related muscle changes, nutrition and neurodegenerative changes.

In the context of the present invention, the term "cachexia" pertains to a syndrome associated with an underlying illness causing ongoing muscle loss that is not entirely reversed with nutritional supplementation. A range of diseases can cause cachexia, most commonly cancer, congestive heart failure, chronic obstructive pulmonary disease, chronic kidney disease and AIDS. Cachexia is a serious clinical consequence of almost all chronic diseases at advanced stages, it affects 50-80% of cancer patients and accounts for up to 20% of cancer deaths, with similar numbers valid for chronic heart failure. Systemic inflammation from these conditions can cause detrimental changes to metabolism and body composition. Cachexia causes mostly muscle loss instead of fat loss.

In the context of the present invention, the term "endocrinopathies" pertains to a disease of an endocrine gland. The term endocrinopathy is commonly used as a medical term for a hormone problem. Common endocrinopathies include hyperthyroidism and hypothyroidism.

In the context of the present invention, the term "malnutrition" pertains to a condition that results from eating a diet, which does not supply a healthy/sufficient amount of one or more nutrients. This includes diets that have too little nutrients so that the diet causes health problems. The nutrients involved can include calories, protein, carbohydrates, fat, vitamins or minerals. A lack of nutrients is called undernutrition or undernourishment while a surplus of nutrients cases overnutrition.

In the context of the present invention, the term "immobility" and/or "reduced physical activity" pertains to a condition of disuse of the muscles for a longer period of time. For example due to bedrest this will result in a significant muscle wasting. A reduced level of physical activity will also lead to loss of muscle mass, which may in part relate to a reduced sensitivity/responsiveness of the muscle.

In the context of the present invention, the term "side effect of medication" pertains to a condition of a medication having the unwanted side effect of negatively affecting muscle mass/quality/function. Examples of such medications are anti-cancer drugs, glucocorticoids, biological therapies, anti-rheumatic treatments, proton-pump inhibitors, statins, analgesics etc.

In the context of the present invention, the term "anabolic resistance" pertains to a condition where the skeletal muscle is unable to respond appropriately to anabolic stimuli by stimulating protein synthesis. Anabolic resistance contributes to muscle mass loss in elderly, during immobilization as well as in response to inflammation and cancer.

In the context of the present invention, the term "insulin resistance" pertains to a condition where the cells in muscles, fat, and liver does not respond well to insulin and do not easily take up glucose from the blood. As a result, the pancreas makes more insulin to help glucose enter the cells. As long as the pancreas can make enough insulin to overcome the cells' weak response to insulin, the blood glucose levels will stay in the healthy range.

In the context of the present invention, the term "eating disorders" such as anorexia nervosa and/or bulimi nervosa pertains to a condition of a mental disorder defined by abnormal eating habits that negatively affect a person's physical and/or mental health. Eating disorders include binge eating disorder, where people eat a large amount in a short period of time; anorexia nervosa, where people eat very little due to a fear of gaining weight and thus have a low body weight; bulimia nervosa, where people eat a lot and then try to rid themselves of the food.

In the context of the present invention, the term "hypoalbuminaemia" pertains to a condition with low serum concentrations of albumin. This condition is often caused by insufficient nutritional intake of protein, excessive loss of protein/albumin (e.g. renal excretion and ascites) or a combination of these two. This is for example seen in patients with e.g. glomerulonephritis, cirrhosis, anorexia nervosa, and cancers.

In the context of the present invention, the term "malabsorption" pertains to insufficient gastrointestinal uptake of nutrients (fat, carbohydrate or glucose), minerals or vitamins.

Malabsorption is associated with conditions or procedures such as gastric bypass, gastric sleeve, short bowel disease, Mb chron and/or colitis.

In some preferred embodiments of the present invention muscle atrophy is selected from one or more of: sarcopenia, cachexia, malnutrition, immobility and/or reduced physical activity.

Whey has been shown to promote muscle protein synthesis and improve nutritional status in cachexic patients and improve muscle mass and inhibit inflammation in patients with sarcopenia. These effects have been attributed to the high content of leucine in whey. BLG has a higher leucine content compared to WPI and in addition to this we have found that BLG surprisingly promotes a greater insulin response. We therefore believe that BLG is beneficial in patients with sarcopenia, cachexia, malnutrition, immobilization and/or reduced physical activity.

In some preferred embodiments of the present invention muscle atrophy is selected from one or more of: sarcopenia and cachexia.

An aspect of the present invention pertains to method of preventing and/or treating a metabolic disorder and/or muscle atrophy in a subject, the method comprising administering a therapeutically effective amount of a) beta-lactoglobulin or b) a nutritional composition comprising beta-lactoglobulin in an amount of at least 75% w/w relative to total protein to a subject in need thereof.

Yet an aspect of the present invention pertains to the use of a) beta-lactoglobulin or b) a nutritional composition comprising beta-lactoglobulin in an amount of at least 75% w/w relative to total protein for increasing the level of insulin and/or glucagon in the blood of a subject.

In a preferred embodiment of the present invention the use of a) beta-lactoglobulin or b) a nutritional composition comprising beta-lactoglobulin in an amount of at least 75% w/w relative to total protein for increasing the level of insulin, glucagon and GLP-1 in the blood of a subject.

In a preferred embodiment of the present invention the use of a) beta-lactoglobulin or b) a nutritional composition comprising beta-lactoglobulin in an amount of at least 75% w/w relative to total protein for increasing the level of insulin, glucagon and GIP in the blood of a subject.

In a preferred embodiment of the present invention the use of a) beta-lactoglobulin or b) a nutritional composition comprising beta-lactoglobulin in an amount of at least 75% w/w relative to total protein for increasing the level of insulin, glucagon, GLP-1 and GIP in the blood of a subject.

A further aspect of the present invention pertains to a non-therapeutic use of a) beta-lactoglobulin or b) a nutritional composition comprising BLG in an amount of at least 75% w/w relative to total protein for one or more of: stimulating or prolonging satiety or increasing satiation, reducing food intake, increasing energy expenditure, reducing adiposity, anabolic effect, muscle anabolic effect in a subject.

In the context of the present invention the term "reducing adiposity" pertains to reducing body fat and/or preventing accumulation of body fat.

The inventors have found that BLG has superior insulinotropic and glucagonotropic effects relative to other milk proteins. BLG can therefore be used in a subject for stimulating or prolonging satiety or increasing satiation, reducing food intake, increasing energy expenditure, reducing adiposity, anabolic effect, muscle anabolic effect. See FIGS. 11 and 12 as well as example 4 and 5.

Insulin is known to effectively damper lipid concentrations in the blood stream as insulin increases the uptake of lipids in the muscles, while glucagon have a positive impact on energy expenditure and inhibit appetite. Administration of BLG is beneficial, as this will result in an increase in the circulating glucagon and insulin concentrations.

The inventors have shown that BLG intake increases the concentration of the circulating insulin, glucagon and specific amino acids such as leucine, phenylalanine, methionine, proline, tyrosine, aspartate, glutamate and lysine. The combination of insulin and especially leucine has shown particularly effective anabolic effects in muscles and may therefore be useful for preserving or building up muscle in the general population (including athletes) where maintenance or accretion of muscle tissue/mass is desired.

In a preferred embodiment of the present invention the non-therapeutic use of a) beta-lactoglobulin or b) a nutritional composition comprising BLG in an amount of at least 75% w/w relative to total protein for one or more of: stimulating or prolonging satiety or increasing satiation, reducing food intake, increasing energy expenditure, reducing adiposity in a subject.

In a preferred embodiment of the present invention the non-therapeutic use of a) beta-lactoglobulin or b) a nutritional composition comprising BLG in an amount of at least 75% w/w relative to total protein is for one or more of: increasing energy expenditure and reducing adiposity in a subject.

Another aspect of the present invention pertains to a non-therapeutic method for one or more of: stimulating or prolonging satiety or increasing satiation, reducing food intake, increasing energy expenditure, reducing adiposity , anabolic effect, muscle anabolic effect in a subject comprising administering a) beta-lactoglobulin or b) a nutritional composition comprising beta-lactoglobulin in an amount of at least 75% w/w relative to total protein.

In a preferred embodiment of the present invention the muscle anabolic effect is selected from one or more of: stimulating/increasing muscle protein synthesis, reducing muscle protein breakdown, improving muscle net balance and/or enhancing muscle recovery.

In a preferred embodiment of the present invention the non-therapeutic method of a) beta-lactoglobulin or b) a nutritional composition comprising BLG in an amount of at least 75% w/w relative to total protein for one or more of: stimulating or prolonging satiety or increasing satiation, reducing food intake, increasing energy expenditure, reducing adiposity in a subject.

In a preferred embodiment of the present invention the non-therapeutic method of a) beta-lactoglobulin or b) a nutritional composition comprising BLG in an amount of at least 75% w/w relative to total protein is for one or more of: increasing energy expenditure and reducing adiposity in a subject.

Another aspect of the present invention pertains to a method of increasing the level of insulin/and or glucagon in the blood of a subject, the method comprising administering to a subject a therapeutically effective amount of a) beta-lactoglobulin or b) a nutritional composition comprising BLG in an amount of at least 75% w/w relative to total protein.

In some preferred embodiments of the present invention the use and/or method involves regulating the level of glucose, insulin, glucagon, glucose-dependent insulinotropic polypeptide (GIP) and/or glucagon-like peptide-1 (GLP-1) in the blood.

In the context of the present invention, the term "insulin" pertains to a peptide hormone produce by the beta cells of the pancreatic islets. It is considered to be the main anabolic hormone of the body. Insulin regulates the metabolism of carbohydrates, fats and protein by facilitating glucose transport from the blood into liver, fat and skeletal muscle cells.

In the context of the present invention the term "glucagon" pertains to a peptide hormone secreted by the alpha-cells of the pancreas. The pancreas releases glucagon when the concentration of insulin (and indirectly glucose) in the bloodstream falls too low. Glucagon causes the liver to convert stored glycogen into glucose, which is released into the bloodstream, increasing blood sugar, this is called glycogenesis.

In the context of the present invention, the term "glucose-dependent insulinotropic polypeptide (GIP)" pertains to a 42 amino acid hormone that is predominately produced by enteroendocrine K-cells and released into the circulation in response to nutrient stimulation. GIP stimulates insulin secretion in a glucose-dependent manner and is thus classified as an incretin hormone.

In the context of the present invention, the term "glucagon-like peptide-1 (GLP-1)" pertains to a 30 or 31 amino acid long peptide hormone deriving from the tissue-specific posttranslational processing of the proglucagon peptide.

GLP-1 is an incretin hormone that has insulinotropic effects; thus, it has the ability to decrease the blood sugar levels in a glucose-dependent manner by enhancing the secretion of insulin.

In some preferred embodiments of the present invention the use and/or method involves increasing the level of insulin and/or glucagon in the blood of the subject.

In some preferred embodiments of the present invention the use and/or method involves increasing the level of insulin in the blood of the subject.

In some preferred embodiments of the present invention the use and/or method involves increasing the level of glucagon in the blood of the subject.

It was surprisingly found by the inventors that administration of BLG to human beings with diabetes raises their circulating concentrations of both insulin and glucagon relative to administration of a similar diet containing whey protein.

It is believed that the insulinotrophic effect of BLG may be partly mediated through increased levels of GIP and/or GLP-1 from the gastrointestinal tract. This is demonstrated in Examples 4 and 5.

The inventors have found that administration of BLG as a premeal also increases the concentrations of GIP and GLP-1 and lower the blood glucose.

Some of the advantages of it is satiety and a lower blood glucose level.

In some preferred embodiments of the present invention the use and/or method involves increasing the level of glucose-dependent insulinotropic polypeptide (GIP) in the blood of the subject.

In some preferred embodiments of the present invention the use and/or method involves increasing the level of glucagon-like peptide-1 (GLP-1) in the blood of the subject.

In some preferred embodiments of the present invention the use and/or method involves lowering the level of glucose in the blood of the subject.

It is known that in addition to GLP-1 analogues, bi-agonists of GLP-1 and glucagon and tri-agonists of GIP, GLP-1 and glucagon are under development for treating obesity. As we surprisingly found that BLG increases the concentrations of all these three hormones. BLG can therefore advantageously be used in the treatment and/or prevention of obesity as we have found that BLG surprisingly increases Glucagon, GLP-1 and GIP.

In some preferred embodiments of the present invention the use and/or method involves increasing the level of glucagon and glucagon-like peptide-1 (GLP-1) in the blood of the subject, for use of preventing and/or treating obesity.

BLG thus provide a natural simulation of effect of bi-agonist for the treatment of obesity.

In some preferred embodiments of the present invention the use and/or method involves increasing the level of glucagon, glucose-dependent insulinotropic polypeptide (GIP) and glucagon-like peptide-1 (GLP-1) in the blood of the subject, for use of preventing and/or treating obesity.

BLG thus provide a natural simulation of effect of tri-agonist for the treatment of obesity.

In some preferred embodiments of the present invention the use and/or method involves increasing the level of glucagon and glucagon-like peptide-1 (GLP-1) in the blood of the subject.

In some preferred embodiments of the present invention the use and/or method involves increasing the level of glucagon, glucose-dependent insulinotropic polypeptide (GIP) and glucagon-like peptide-1 (GLP-1) in the blood of the subject.

In some preferred embodiments of the present invention the use and/or method involves increasing the level of glucagon and glucose-dependent insulinotropic polypeptide (GIP) in the blood of the subject.

The inventors surprisingly found that consuming BLG as a premeal resulted in elevated concentrations of leucine and phenylalanine which have been shown to stimulate insulin secretion. Likewise, methionine and tyrosine have been shown to increase glucagon concentrations. Studies on dogs and rodents have shown that aspartate, glutamate, lysine, and proline stimulate glucagon secretion as well. All these aforementioned amino acids were more elevated in plasma after BLG consumption compared with WPI.

In some preferred embodiments of the present invention the administration of a) BLG or b) the nutritional composition involves increasing the amount of amino acids stimulating the concentration of glucagon and/or insulin in the blood.

In some preferred embodiments of the present invention the amino acids are tyrosine, methionine, proline, aspartate, glutamate, lysine, leucine and/or phenylalanine.

In a preferred embodiment of the present invention the subject is a human being.

In some preferred embodiments of the present invention the subject is selected from one or more of: an obese, a subject suffering from dyslipidemia, a subject suffering from hepatic steatosis, a subject having prediabetes or diabetes, a subject having metabolic syndrome, a subject having hypo-glycaemia, a subject having glucose intolerance, a subject at risk of sarcopenia, a subject at risk of cachexia, a subject having endocrinopathies, a malnourished human being, immobilized or reduced physical activity, a subject suffering from side effects of medication, a subject having anabolic resistance, a subject having insulin resistance, a subject having eating disorders, a subject having malabsorption, a subject having hypoalbiminaemia and/or a subject having cirrhosis In some preferred embodiments of the present invention the subject is obese, have a metabolic syndrome, has dys-lipidemia, diabetes, prediabetes, has sarcopenia, cachexia, is malnourished, immobilized and/or have reduced physical activity.

In some preferred embodiments of the present invention the subject is obese, has a metabolic syndrome, dyslipi-demia, diabetes and/or prediabetes.

In some preferred embodiments of the present invention the subject is obese, has a metabolic syndrome, and/or dyslipidemia.

In some preferred embodiments of the present invention the subject is obese.

In some preferred embodiments of the present invention the subject has a metabolic syndrome.

In some preferred embodiments of the present invention the subject has dyslipidemia.

In some preferred embodiments of the present invention the subject has sarcopenia, cachexia, is malnourished, immobilized and/or has reduced physical activity.

In some preferred embodiments of the present invention the subject has sarcopenia or cachexia.

In some preferred embodiments of the present invention the subject is a healthy human being.

In some preferred embodiments of the present invention the subject is selected from one or more of athletes, over-weight/obese, sedentary, recreationally active, middle-aged, elderly, bodybuilder, human being with a reduced muscle mass, aiming at increasing or maintaining muscle mass, human being at risk of developing a reduced muscle mass and/or being malnourished.

In some preferred embodiments of the present invention the subject has prediabetes or diabetes.

In some preferred embodiments of the present invention the subject is obese and/or is having a metabolic syndrome.

In some preferred embodiments of the present invention the subject is suffering from sarcopenia and/or cachexia.

In some preferred embodiments of the present invention the nutritional composition b) comprises a total amount of protein of at least 1.0% w/w relative to the weight of the nutritional composition.

The inventors have found that administration of BLG according to the present invention surprisingly has a superior insulinotropic effect relative to other milk proteins and can therefore be used in preventing and/or treating diabetes in a subject. It has thus been found that BLG surprisingly increases circulating concentrations of insulin and GIP, which are hormones (and pharmaceuticals) known to reduce hyperglycemia. The effects are superior to using similar doses of WPI or casein as a protein source.

An aspect of the invention pertains to beta-lactoglobulin for use in preventing and/or treating diabetes or prediabetes in a subject.

The inventors have found that BLG has superior insulinotropic effects relative to other milk proteins and therefore can be used to prevent and/or treat diabetes or prediabetes. It thus has an insulin increasing potential in various subgroups of prediabetes and/or diabetes such as for example type 2 diabetes (TDM2), metabolic syndrome, gestational diabetes (GDM), Latent Autoimmune Diabetes in Adulthood (LADA), different varieties of prediabetes, and early phases of type 1 diabetes (TDM1), where the beta-cell function is not totally extinct.

In some preferred embodiments of the invention, the diabetes is selected from the group consisting of type 2 diabetes, type 1 diabetes, gestational diabetes (GDM), and/or Latent Autoimmune Diabetes in Adulthood (LADA) or a combination thereof.

In some preferred embodiments of the invention, the diabetes is a type 2 diabetes.

In some embodiments of the invention, the diabetes is type 1 diabetes, wherein the subject has a degree of preserved beta cell function. In some other embodiments of the invention, the diabetes is gestational diabetes (GDM). In other embodiments of the invention, the diabetes is Latent Autoimmune Diabetes in Adulthood (LADA).

In some preferred embodiments of the invention, the diabetes is type 2 diabetes and/or Latent Autoimmune Diabetes in Adulthood (LADA).

In some preferred embodiments of the invention the diabetes is type 2 diabetes and/or gestational diabetes (GDM).

In some preferred embodiments of the invention, the subject has diabetes or pre-diabetes.

In some preferred embodiments of the invention, the subject has diabetes. In some preferred embodiments of the invention, the subject has prediabetes.

In the context of the present invention, the term "mammal" or "mammalian" includes but is not limited to rodents, aquatic mammals, domestic animals such as dogs and cats, farm animals such as sheep, pigs, cows and horses and humans. Wherein the term mammal or mammalian is used, it is contemplated that it also applies to other animals that are capable of the effect exhibited or intended to be exhibited by the mammal.

In a preferred embodiment of the present invention, the subject is a mammal.

In some preferred embodiments of the invention, the subject is selected from the group consisting of a mammal including domestic animals and human beings.

In some preferred embodiments of the invention, the subject is a human being.

Diabetes or prediabetes, for example type 2 diabetes, is observed with human beings, but diabetes is also becoming more widespread among domestic animals and particularly with animals kept as pet animals. Therefore, in some embodiments of the invention, the subject is preferably a dog or a cat.

In some embodiments of the present invention, the subject is a human being, a dog and/or a cat.

In the context of the present invention, the term "blood plasma" pertains to the light yellowish liquid component of blood that holds the blood cells in whole blood in suspension. It is the liquid part of the blood that carries cells and proteins throughout the body. The blood plasma makes up to about 55% of the body's total blood volume. Blood plasma comprises mostly water (making up to 95% by volume), and contains dissolved proteins (6-8%) (e.g. serum albumins, glob-ulins, and fibrinogen), glucose, clotting factors, electrolytes (Na+, Ca2+, Mg2+, HCO3−, Cl−, etc.), hormones, carbon dioxide and oxygen.

In the context of the present invention, the term "blood serum" pertains to the blood plasma without the clotting factors such as fibrinogens.

In some preferred embodiments of the invention, the use involves lowering the blood glucose level.

In the context of the present invention, the term "glucose" pertains to a simple sugar with the molecular form $C_6H_{12}O_6$. Glucose circulates in the blood. Approximately 4 grams of glucose are present in the blood of a 70 kilogram human at all times. A persistent elevation in blood glucose leads to glucose toxicity, which contributes to cell dysfunction and diabetes. Glucose can be transported from the intestines or liver to other tissues in the body via the bloodstream. Cellular glucose uptake is primarily regulated by insulin.

Transient elevations in blood glucose will appear following a standard meal. Insulin is the most potent hormone in the regulation of glucose homeostasis. Higher insulin concentrations preceding, during and following a meal will therefore most likely circumvent or damper unwanted glucose fluctuations.

In some preferred embodiments of the invention, the use involves regulating the level of insulin, glucagon, glucose-dependent insulinotropic polypeptide (GIP) and/or glucagon-like peptide-1 (GLP-1) in the blood.

In some preferred embodiments of the invention, the use involves increasing the level of insulin in the blood.

It was surprisingly found by the inventors that administration of BLG to human beings with provoked insulin resistance, similar to that found in diabetes or prediabetes patients, raises their circulating concentrations of insulin with 62% relative to administration of a similar diet containing casein and with 30% relative to a similar diet containing whey protein.

Insulin resistance also occurs in subjects with diabetes and prediabetes and administration of BLG can therefore be used to treat such patients.

It is believed that the insulinotrophic effect of BLG may be partly mediated through increased levels of GIP and/or GLP-1 from the gastrointestinal tract. This is demonstrated in Example 4.

Inflammation, bedrest and fasting (as used in this trial, see Example 4) are all known to cause insulin resistance. The insulinotropic effects of BLG may therefore also be present in subjects with diabetes or prediabetes having a preserved beta cell function.

In some preferred embodiments of the invention, the use involves increasing the level of GIP in the blood.

The inventors also surprisingly found that administration of BLG to human subjects with provoked insulin resistance, similar to that found in patients with diabetes or prediabetes, raises the blood concentrations of GIP. This is demonstrated in Example 4.

It was found that plasma GIP (which is mainly secreted from enteroendocrine K-cells in the proximal small intestine) increased more after ingestion of BLG compared to casein and whey protein. This could be part of a mechanistic explanation for the higher insulin concentrations detected after BLG administration compared with casein and whey/WPI. Both GIP and GLP-1 stimulate insulin secretion from beta cells (incretin effect).

In some preferred embodiments of the invention, the use involves increasing the level of glucagon-like peptide-1 (GLP-1) in the blood.

It was surprisingly found that GLP-1 increased more after ingestion of BLG compared to casein. This could be part of a mechanistic explanation for the higher insulin concentrations detected after BLG administration compared with casein. Both GIP and GLP-1 stimulate insulin secretion from beta cells (incretin effect).

In some preferred embodiments of the invention, the use involves increasing the level of glucagon in the blood.

In some preferred embodiments of the invention, the beta-lactoglobulin is administered in the form of a nutritional composition.

In the context of the present invention, the term "nutritional product" or "nutritional composition" means food products comprising one or more macro nutrients and optionally further components comprising fibres, vitamins, flavouring agents, artificial sweeteners, minerals and trace elements. A nutritional product or nutritional composition may comprise protein as the only nutrient or may for example comprise protein and a flavouring agent.

The term "nutrient" means a substance used by an organism to survive, grow and reproduce. Nutrients can be either macronutrients or micronutrients. Macronutrients are nutrients that provide energy when consumed e.g. protein, lipid and carbohydrate. Micronutrients are nutrients like vitamins, minerals and trace elements.

A nutritional composition may also contain flavours including natural and synthetic flavours, colorants and enhancers, thickening agents, pH modifiers, stabilizers, antiseptics, glycerine, alcohols, carbonating agents used for carbonated beverages, and so forth.

In some preferred embodiments of the invention, the beta-lactoglobulin is administered in the form of a liquid nutritional composition.

In the context of the present invention, the terms "liquid" and "solution" encompass both compositions that are free of particulate matter and compositions that contain a combination of liquid and solid and/or semi-solid particles, such as e.g. protein crystals or other protein particles. A "liquid" or a "solution" may therefore be a suspension or even a slurry. However, a "liquid" and "solution" are preferably pumpable.

In the context of the present invention, the term "liquid nutritional composition" relates to any water based nutritional liquid which can be ingested as drink, e.g. by pouring or tube feeding.

It is particularly preferred that the nutritional composition comprises a BLG isolate, e.g. in combination with other protein sources, preferably as the main protein source and possibly even as the only protein source.

The liquid nutritional composition typically contains a total amount of water in the range of 50-99% w/w, preferably in the range of 45-98% w/w, more preferably in the range of 40-95% w/w, even more preferably in the range of 35-90% w/w, and most preferably in the range of 30-85% w/w.

In some other preferred embodiments of the invention, the liquid nutritional composition contains a total amount of water in the range of 55-90% w/w, preferably in the range of 57-85% w/w, more preferably in the range of 60-80% w/w, even more preferably in the range of 62-75% w/w, and most preferably in the range of 65-70% w/w.

In some other preferred embodiments of the invention, the liquid nutritional composition contains a high amount of water, such as a total amount of water in the range of 85-98% w/w, preferably in the range of 92-97.5% w/w, more preferably in the range of 94-97% w/w, even more preferably in the range of 95-97% w/w, and most preferably in the range of 96-97% w/w. These embodiments are e.g. useful for transparent, water-like beverages. In some other embodiments, it is preferred that the liquid nutritional composition contains a total amount of water in the range of 95-96% w/w.

In some preferred embodiments of the invention, the beta-lactoglobulin is administered in the form of a solid nutritional composition, preferably as a bar, as flakes, as biscuits or as pellets.

In some preferred embodiments of the invention, the beta-lactoglobulin is administered in the form of pellets, powders, granules, crystals or tablets.

In some preferred embodiments of the invention BLG is administered in the form of a tablet.

It is particularly preferred that the nutritional composition is in the form of a rehydrated instant powder.

The term "instant powder" means a nutritional powder-which can be converted to a liquid composition by addition of a liquid, such as water.

In some preferred embodiments of the invention, BLG is in the form of BLG crystals. The BLG crystals are converted to a liquid composition by addition of a liquid, such as water.

In some preferred embodiments of the invention, the beta-lactoglobulin is present in an amount of at least 1.0% w/w relative to the weight of the nutritional composition.

In some preferred embodiments of the present invention, the beta-lactoglobulin is present in an amount of at least 5.0% w/w relative to the weight of the composition, more preferably at least 10.0% w/w relative to the weight of the composition, preferably at least 20.0% w/w relative to the weight of the composition.

In other preferred embodiments of the present invention, the beta-lactoglobulin is present in an amount of 1.0 to 45% w/w relative to the weight of the composition, more preferably 2.0 to 35% w/w, even more preferably 3.0 to 32% w/w, even more preferably 4.0 to 30% w/w and most preferred 5.0 to 25% w/w relative to the weight of the composition.

In some embodiments of the invention, it is advantageous that the beta-lactoglobulin is present in the nutritional composition in an amount of 2.0 to 15.0% w/w relative to the weight of the composition.

Therefore, in some embodiments of the invention, the beta-lactoglobulin is most preferably present in the nutritional composition in an amount of 2.0 to 15% w/w relative to the weight of the composition, preferably a total amount of BLG of 3.0 to 12% w/w relative to the weight of the composition, preferably a total amount of BLG of 5.0 to 10% w/w relative to the weight of the composition, preferably a total amount of BLG of 6.0 to 8.0% w/w relative to the weight of the composition.

In some other embodiments of the invention, it is advantageous that the beta-lactoglobulin content of the nutritional composition is high such as 10.0 to 45.0% w/w relative to the weight of the composition.

Therefore, in some embodiments of the present invention the beta-lactoglobulin is most preferably present in an amount of 10.0 to 40.0% w/w relative to the weight of the composition, preferably a total amount of BLG of 12.0 to 35% w/w relative to the weight of the composition, preferably a total amount of BLG of 15 to 30% w/w relative to the weight of the composition, preferably a total amount of BLG of 20 to 25% w/w relative to the weight of the composition.

In other preferred embodiments of the invention, it is advantageous that the beta-lactoglobulin is present in the nutritional composition in an amount of 5.0 to 45.0% w/w relative to the weight of the nutritional composition, preferably 6.0 to 35% w/w, more preferably 7.0 to 34% w/w, even more preferred 8.0-32% w/w, and most preferred 10-30% w/w.

In other preferred embodiments of the invention it is advantageous that the beta-lactoglobulin is present in a high amount of 21-35% w/w, the beta-lactoglobulin is thus preferably present in an amount of 21 to 35% w/w relative to the weight of the nutritional composition, preferably a total amount of BLG of 25 to 35% w/w relative to the weight of the nutritional composition, more preferably a total amount of BLG of 28 to 35% w/w relative to the weight of the nutritional composition, and even more preferably a total amount of BLG of 30 to 35% w/w relative to the weight of the nutritional composition.

In other preferred embodiments of the present invention, the beta-lactoglobulin is present in the nutritional composition in an amount of 5.0 to 45% w/w relative to the weight of the composition, more preferably 5.0 to 35% w/w, even more preferably 5.0 to 34% w/w, and most preferred 5.0 to 32% w/w.

In the context of the present invention, the term "dry" or "dried" means that the composition or product in question comprises at most 10% w/w water, preferably at most 6% w/w and more preferably even less.

In some preferred embodiments of the invention, the nutritional composition comprises a total amount of protein of at least 1.0% w/w relative to the weight of the nutritional composition and wherein at least 75% w/w of the protein is beta-lactoglobulin.

In some preferred embodiments of the present invention the nutritional composition comprises BLG in an amount of at least 80% w/w relative to total protein, more preferably at least 85 w/w % relative to total protein, more preferably at least 88% w/w relative to total protein, more preferably at least 90% w/w relative to total protein, even more preferably at least 91% w/w relative to total protein, and most preferably at least 92% w/w relative to total protein of the protein is BLG.

Preferably, at least 80% w/w, more preferably, at least 85 w/w %, more preferably, at least 88% w/w of the protein is BLG, more preferably at least 90% w/w, even more preferably at least 91% w/w, and most preferably at least 92% w/w of the protein is BLG.

Even higher relative amounts of BLG are both feasible and desirable thus in some preferred embodiments of the invention, at least 94% w/w of the protein is BLG, more preferably at least 96% w/w of the protein is BLG, even more preferably at least 98% w/w of the protein is BLG, and most preferably approx. 100% w/w of the protein is BLG.

For example, the nutritional composition preferably comprises BLG in an amount of at least 97.5% w/w relative to total protein, preferably at least 98.0% w/w relative to total protein, more preferably at least 98.5% w/w relative to total protein, even more preferably at least 99.0% relative to total protein, and most preferably BLG in an amount of at least 99.5% w/w relative to total protein, such as approx. 100.0% w/w relative to total protein.

For example, the nutritional composition preferably comprises BLG in an amount of 88.0 to 100% w/w relative to total protein, preferably 90.0 to 99.5% w/w, more preferably 95.0 to 99.0% w/w, even more preferably 96.0 to 98.0% w/w, and most preferably BLG in an amount of 97.0 to 99.0% w/w relative to total protein.

In some preferred embodiments of the present invention, the nutritional composition comprises a total amount of protein of at least 1.0% w/w relative to the weight of the composition, preferably at least 5.0% w/w relative to the weight of the composition, more preferably at least 10.0% w/w relative to the weight of the composition, preferably at least 20.0% w/w relative to the weight of the composition.

In other preferred embodiments of the present invention, the nutritional composition comprises a total amount of protein of 1.0 to 45% w/w relative to the weight of the composition, more preferably 2.0 to 35% w/w, even more preferably 3.0 to 32% w/w, even more preferably 4.0 to 30% w/w and most preferred 5.0 to 25% w/w.

In some embodiments of the invention, it is advantageous that the nutritional composition has a protein content of 2.0 to 15.0% w/w relative to the weight of the composition.

Therefore, in some embodiments of the invention, the nutritional composition preferably comprises a total amount of protein of 2.0 to 15% w/w relative to the weight of the composition, preferably a total amount of protein of 3.0 to 12% w/w relative to the weight of the composition, preferably a total amount of protein of 5.0 to 10% w/w relative to the weight of the composition, preferably a total amount of protein of 6.0 to 8.0% w/w relative to the weight of the composition.

In some embodiments of the invention, it is advantageous that the protein content of the nutritional composition is high such as 10.0 to 45.0% w/w relative to the weight of the composition. High concentrations of protein such as 10.0 to 45.0% w/w are particularly relevant when the composition is administered as a pre-meal.

Therefore in some embodiments of the present invention, the nutritional composition preferably comprises a total amount of protein of 10.0 to 40.0% w/w relative to the weight of the composition, preferably a total amount of protein of 12.0 to 35% w/w relative to the weight of the composition, preferably a total amount of protein of 15 to 30% w/w relative to the weight of the composition, preferably a total amount of protein of 20 to 25% w/w relative to the weight of the composition.

In other preferred embodiments of the invention, it is advantageous that the protein content of the nutritional composition is 5.0 to 45.0% w/w relative to the weight of the nutritional composition, preferably 6.0 to 35% w/w, more preferably 7.0 to 34% w/w, even more preferred 8.0-32% w/w, and most preferred 10-30% w/w.

In other preferred embodiments of the invention, the nutritional composition preferably comprises a total amount of protein of 21 to 35% w/w relative to the weight of the nutritional composition, preferably a total amount of protein of 25 to 35% w/w relative to the weight of the nutritional composition, more preferably a total amount of protein of 28 to 35% w/w relative to the weight of the nutritional composition, and even more preferably a total amount of protein of 30 to 35% w/w relative to the weight of the nutritional composition.

In other preferred embodiments of the present invention, the nutritional composition comprises a total amount of protein of 5.0 to 45% w/w relative to the weight of the composition, more preferably 5.0 to 35% w/w, even more preferably 5.0 to 34% w/w, and most preferred 5.0 to 32% w/w.

In even further preferred embodiments of the present invention, the nutritional composition, e.g. in the form of a powder, granules, crystal, pellet or a tablet, comprises a total amount of protein of 46 to 100% w/w relative to the weight of the composition, more preferably 50 to 99% w/w, even more preferably 60 to 95% w/w, even more preferably 60 to 92% w/w and most preferred 70 to 90% w/w.

In some embodiments of the present invention, the nutritional composition has a pH in the range of 3.0-4.7.

In some embodiments of the present invention, the nutritional composition has a pH in the range of 3.0-4.3. The inventors have found that this pH-range is particularly preferred for production of transparent liquid compositions having low viscosity and improved taste.

In some preferred embodiments of the invention, the nutritional composition has a pH in the range of 3.1-4.6, or preferably 3.2-4.4, or preferably 3.4-4.2, more preferably 3.5-4.0, and even more preferably 3.5-3.9.

In some preferred embodiments of the invention, the nutritional composition has a pH in the range of 4.1-4.7 this pH range is particularly relevant for the production of stable compositions having a milky appearance and a high turbidity while still having a low viscosity.

In some preferred embodiments of the invention, the nutritional composition has a pH in the range of 6.5-8.0. Most preferably the pH employed is a pH of 6.5 to 7.5 or a pH of 6.8 to 7.2.

The nutritional composition preferably has a pH in the range of 5.5 to 6.2, alternatively the nutritional composition has a pH in the range of 6.2-8.0.

The nutritional composition of the invention was found preferably to be clear and transparent having a low viscosity at a pH in the range of 6.2-8.0., preferably pH 6.3-7.6, more preferably a pH of 6.5 to 7.2.

In some preferred embodiments of the invention, the nutritional composition is at least pasteurised.

In some preferred embodiments of the invention, the nutritional composition is sterilised, and hence sterile.

In the context of the present invention, the term "sterile" means that the sterile composition or product in question does not contain any viable microorganisms and therefore is devoid of microbial growth during storage at room temperature. A composition that has been sterilised is sterile.

When a liquid, such as a nutritional composition, is sterilised and packaged aseptically in a sterile container, it typically has a shelf life of at least six months at room temperature. The sterilization treatment kills spores and microorganisms that could cause spoilage of the liquid.

The terms "consists essentially of" and "consisting essentially of" mean that the claim or feature in question encompasses the specified materials or steps and those that do not materially affect the basic and novel characteristic(s) of the claimed invention.

In the context of the present invention, the phrase "Y and/or X" means "Y" or "X" or "Y and X". Along the same line of logic, the phrase "$n_1$, $n_2$, . . . , $n_{i-1}$, and/or $n_i$" means "$n_1$" or "$n_2$" or . . . or "$n_{i-1}$" or "$n_i$" or any combination of the components: $n_1$, $n_2$, . . . $n_{i-1}$, and $n_i$.

In the context of the present invention, the weight percentage (% w/w) of a component of a certain composition, product, or material means the weight percentage of that component relative to the weight of the specific composition, product, or material, unless another reference (e.g. total solids or total protein) is specifically mentioned.

In the context of the present invention, the term "weight ratio" between component X and component Y means the value obtained by the calculation $m_X/m_Y$ wherein $m_X$ is the amount (weight) of components X and $m_Y$ is the amount (weight) of components Y.

In some preferred embodiments of the invention, the a) beta-lactoglobulin or b) nutritional composition is administered to the subject in a serving dose of at least 0.01 g protein/kg body weight, preferably at least 0.03 g protein/kg body weight, more preferably at least 0.05 g protein/kg body weight, even more preferably at least 0.06 g protein/kg body weight, most preferably at least 0.07 g protein/kg body weight.

In other preferred embodiments of the invention, it is advantageous that the a) beta-lactoglobulin or b) nutritional composition is administered to the subject in a serving dose of 0.01 to 0.60 g protein/kg body weight, preferably in a serving dose of 0.02 to 0.50 g protein/kg body weight, more preferably in a serving dose of 0.03 to 0.40 g protein/kg body weight, even more preferably in a serving dose of 0.05 to 0.35 g protein/kg body weight, most preferably in a serving dose of 0.07-0.30 g protein/kg body weight.

In other preferred embodiments of the invention, it is advantageous that the a) beta-lactoglobulin or b) nutritional composition is administered to the subject in a serving dose of 0.10 to 0.60 g protein/kg body weight, preferably in a serving dose of 0.20 to 0.55 g protein/kg body weight, more preferably in a serving dose of 0.25 to 0.45 g protein/kg body weight.

These serving doses will provide a subject with a sufficient quantity of beta-lactoglobulin to treat and/or prevent a metabolic disorder and/or muscle atrophy.

These serving doses are also particularly relevant to treat and/or prevent metabolic syndrome, obesity and/or dyslipidemia.

These serving doses are also particularly relevant to treat and/or prevent sarcopenia, cachexia, malnutrition, immobility and/or reduced physical activity These doses will provide a subject with a sufficient quantity of beta-lactoglobulin to treat and/or prevent diabetes or prediabetes.

Low serving doses of BLG is advantageous, when it is important to keep the calorie content low. The administration of low doses of beta-lactoglobulin of the present invention is also preferred for patients suffering from kidney diseases or otherwise having a reduced kidney function, as high doses of protein can further reduce the kidney function over time.

Thus, in other preferred embodiments of the invention, it is advantageous that the a) beta-lactoglobulin or b) nutritional composition is administered to the subject in a serving dose of 0.01 to 0.15 g protein/kg body weight, preferably in a serving dose of 0.02 to 0.12 g protein/kg body weight, more preferably in a serving dose of 0.03 to 0.10 g protein/kg body weight, even more preferably in a serving dose of 0.05 to 0.09 g protein/kg body weight.

In other preferred embodiments of the invention, it is advantageous that the a) beta-lactoglobulin or b) nutritional composition is administered to the subject in a serving dose of 0.10 to 0.60 g protein/kg body weight, preferably in a serving dose of 0.12 to 0.50 g protein/kg body weight, more preferably in a serving dose of 0.15 to 0.45 g protein/kg body weight, even more preferably in a serving dose of 0.30 to 0.40 g protein/kg body weight.

For the calculation of serving dose or daily dose an average bodyweight of 70 kg is used, the subject may be a male or a female.

In other preferred embodiments of the invention, it is advantageous that the a) beta-lactoglobulin or b) nutritional composition is administered to the subject in a serving dose of 0.7 g to 40 g protein, preferably in a serving dose of 1 to 30 g protein, more preferably in a serving dose of 3 to 25 g protein, even more preferably in a serving dose of 4 to 22 g protein, most preferably in a serving dose of 5 to 20 g protein.

In some preferred embodiments of the invention, the a) beta-lactoglobulin or b) nutritional composition is administered to a subject in a daily dose of at least 0.03 g protein/kg body weight, preferably at least 0.09 g protein/kg bodyweight, more preferably at least 0.15 g protein/kg body weight, even more preferably at least 0.18 g protein/kg body weight, most preferably at least 0.20 g protein/kg body weight In other preferred embodiments of the invention, it is advantageous that the a) beta-lactoglobulin or b) nutritional composition is administered to the subject in a daily dose of 0.03 to 1.8 g protein/kg body weight, preferably in a daily dose of 0.05 to 1.6 g protein/kg body weight, more preferably in a daily dose of 0.09 to 1.2 g protein/kg body weight, even more preferably in a daily dose of 0.10 to 1.0 g protein/kg body weight, most preferably in a daily dose of 0.20-0.90 g protein/kg body weight.

These daily doses will provide a subject with a sufficient quantity of beta-lactoglobulin to treat and/or prevent a metabolic disorder and/or muscle atrophy.

In particular, these daily doses are relevant to provide a subject with a sufficient quantity of beta-lactoglobulin to treat and/or prevent metabolic syndrome, obesity and/or dyslipidemia.

The inventors have also found that these daily doses are relevant to provide a subject with a sufficient quantity of beta-lactoglobulin to treat and/or prevent sarcopenia, cachexia, malnutrition, immobility and/or reduced physical activity.

In other preferred embodiments of the invention, it is advantageous that the a)beta-lactoglobulin or b) nutritional composition is administered to the subject in a daily dose of 0.03 to 0.70 g protein/kg body weight, preferably in a daily dose of 0.05 to 0.60 g protein/kg body weight, more preferably in a daily dose of 0.09 to 0.50 g protein/kg body weight, even more preferably in a daily dose of 0.1 to 0.4 g protein/kg body weight, most preferably in a daily dose of 0.20-0.30 g protein/kg body weight.

In other preferred embodiments of the invention, it is advantageous that the a)beta-lactoglobulin or b) nutritional composition is administered to the subject in a daily dose of 0.50 to 2 g protein/kg body weight, preferably in a daily dose of 1.0 to 1.8 g protein/kg body weight, more preferably in a daily dose of 1.2 to 1.6 g protein/kg body weight, even more preferably in a daily dose of 1.3 to 1.5 g protein/kg body weight, most preferably in a daily dose of 1.2-1.4 g protein/kg body weight.

In other preferred embodiments of the invention, it is advantageous that the a) beta-lactoglobulin or b) nutritional composition is administered to the subject in a daily dose of 2 g to 120 g protein, preferably in a daily dose of 5 to 100 g protein, more preferably in a daily dose of 10 to 90 g protein, even more preferably in a daily dose of 12 to 80 g protein, most preferably in a daily dose of 15 to 60 g protein.

In other preferred embodiments of the invention, it is advantageous that the a) beta-lactoglobulin or b) nutritional composition is administered to the subject in a daily dose of 0.30 to 1.80 g protein/kg body weight, preferably in a serving dose of 0.60 to 1.65 g protein/kg body weight, more preferably in a serving dose of 0.75 to 1.35 g protein/kg body weight.

In some preferred embodiments of the invention, the a) beta-lactoglobulin or b) nutritional composition is administered as a pre-meal.

In the context of the present invention, a "pre-meal" is defined as a small meal consumed 0-90 minutes before the actual meal.

In some preferred embodiments of the present invention, the pre-meal may even essentially consist of protein and water.

In some preferred embodiments of the present invention, the pre-meal is administered multiple times per day, preferably three times a day.

In other preferred embodiments of the present invention the pre-meal is administered two times a day.

In some preferred embodiments of the present invention the a) the beta-lactoglobulin or b) the nutritional composition is administered 0-60 minutes prior to a meal, more preferred 0-40 minutes prior to a meal, even more preferred 0-30 minutes prior to a meal.

In some preferred embodiments of the present invention the a) the beta-lactoglobulin or b) the nutritional composition is administered 15-60 minutes prior to a meal, more preferably 20-40 minutes prior to a meal, even more preferably 25-35 minutes prior to a meal.

In some preferred embodiments of the invention, the a) beta-lactoglobulin or b) nutritional composition is administered 0-90 minutes prior to a meal, preferably 5-70 minutes prior to a meal, more preferably 10-50 minutes prior to a meal, even more preferably 20-30 minutes prior to a meal.

In a preferred embodiment of the present invention, the a) beta-lactoglobulin or b) nutritional composition is administered 0-60 minutes prior to a meal, even more preferred 0-30 minutes prior to a meal. In other preferred embodiments of the present invention the beta-lactoglobulin is administered 2-30 minutes prior to a meal, more preferably 5-30 minutes prior to a meal, even more preferably 10-30 minutes prior to a meal.

In other embodiments of the present invention, the a) beta-lactoglobulin or b) nutritional composition is administered 30-90 minutes prior to a meal, preferably 35-70 minutes prior to a meal, more preferably 40-50 minutes prior to a meal.

In other embodiments of the present invention, the a) beta-lactoglobulin or b) nutritional composition is administered at least 5 minutes prior to a meal, preferably at least 10 minutes prior to a meal, more preferably at least 20 minutes prior to a meal, even more preferably at least 40 minutes prior to a meal.

In a preferred embodiment of the invention, the a)beta-lactoglobulin or b) nutritional composition is administered as part or at the end of a meal.

A typical meal comprises 25-40E % fat, 45-60E % carbohydrates and 10-20E % protein.

In a preferred embodiment of the invention, a meal comprises less than 30E % fat, 20-75E % carbohydrates and 25-50E % protein.

In another preferred embodiment of the invention, the meal comprises 20-25E % protein In some preferred embodiments of the invention, the a) beta-lactoglobulin or b) nutritional composition is administered in combination with an additional medicament.

In a preferred embodiment of the invention, the additional medicament has an antiglycemic effect.

In an embodiment of the invention, the additional medicament is selected from the group consisting of: sulfonylthiourea, Sglt2 inhibitors, metformin, insulin, DPP4 inhibitors, GLP-1 analogues and combinations thereof.

In a preferred embodiments of the invention, the additional medicament is sulfonylthiourea.

In some other preferred embodiments of the present invention the additional medicament is selected from one or more of: statins, fibrates, anion exchange resins, niacin derivates and Ezetimibe.

In some preferred embodiments of the present invention the additional medicament is selected from one or more of Orlistat and/or Saxenda. Saxenda is a GLP-1 analogue.

In some preferred embodiments of the present invention the additional medicament is sulfonylthiourea.

In some preferred embodiments of the present invention the administration of a) BLG or b) the nutritional composition is by oral administration.

In the context of the present invention, the term "oral administration" or "administered orally" pertains to a route of administration, wherein a substance is taken through the mouth. It also comprises enteral administration, which is defined as a way to provide a substance through a tube placed in the nose, the stomach or the small intestine, it is also known as tube feeding.

In some preferred embodiments of the invention, the native conformation of BLG is maintained. The native conformation of the proteins is preferably maintained by avoiding heat-treatments that result in irreversible changes in protein conformation of at least BLG, and preferably of all the proteins.

The degree of protein nativeness depends on a number of factors including protein concentration, pH, temperature and time of heat-treatment.

In some preferred embodiments of the invention, the beta-lactoglobulin has a degree of protein denaturation of at most 10%.

Preferably a degree of protein denaturation of at most 8%, more preferably a degree of protein denaturation of at most 5%, even more preferably a degree of protein denaturation of at most 3%, even more preferably a degree of protein denaturation of at most 1%, and most preferably a degree of protein denaturation of at most 0.5%.

In some preferred embodiments of the present invention, the degree of protein denaturation is 0.5 to 10%, even more preferably a degree of protein denaturation of 1 to 8%, even more preferably a degree of protein denaturation of 1 to 5% and most preferably a degree of protein denaturation of 0.5 to 3%.

When the BLG has been subjected for example to a high temperature heat-treatment or other means of denaturation, the degree of protein denaturation increases.

In some embodiments of the invention, the degree of protein denaturation is more than 10%, more preferably a degree of protein denaturation of more than 20%, preferably a degree of protein denaturation of more than 30%, preferably a degree of protein denaturation of more than 40%, or preferably a degree of protein denaturation of more than 50%, or preferably a degree of protein denaturation of more than 60% or preferably a degree of protein denaturation of more than 70%, or preferably a degree of protein denaturation of more than 80%, or preferably a degree of protein denaturation of more than 90%, or preferably more than 95%, or preferably more than 99%.

In a preferred embodiment of the invention, the beta-lactoglobulin has a degree of protein denaturation of more than 10%.

In some preferred embodiments of the present invention the degree of protein denaturation is 10 to 99%, even more preferably a degree of protein denaturation of 20 to 90%, even more preferably a degree of protein denaturation of 25 to 90% and even more preferably a degree of protein denaturation of 30 to 90% and even more preferably a degree of protein denaturation of 50 to 95% and most preferably a degree of protein denaturation of 60 to 99%.

In some preferred embodiments of the present invention, the nutritional composition may even essentially consist of protein. In some preferred embodiments of the invention, the protein is BLG.

The present inventors have found that it can be advantageous to add additional ingredients to the nutritional composition.

In some embodiments of the invention, the nutritional composition furthermore comprises at least one additional ingredient selected from the group consisting of vitamins, flavouring agent, minerals, sweeteners, antioxidants, food acid, lipids, carbohydrate, prebiotics, probiotics, whole milk and non-whey protein or a combination thereof.

In some preferred embodiments of the present invention, the nutritional composition furthermore comprises a flavoring agent. In other preferred embodiments of the present invention, the nutritional composition comprises BLG a flavoring agent and water. In other preferred embodiments of the present invention, the nutritional composition furthermore comprises a sweetener. In some preferred embodiments of the present invention, the nutritional composition furthermore comprises a flavoring agent and a sweetener.

In other preferred embodiments of the present invention, the nutritional composition furthermore comprises soluble fibers.

In the concept of the present invention, the term "soluble fiber", "dietary fibers" or "non-digestible polysaccharides" pertains to soluble fibers such as agar, alginates, carubin, pectin, e.g. pectins from fruits and vegetables, e.g. from citrus fruits and apples, and its derivatives, betaglucan, such as oat betaglucan, carrageenans, in particular kappa, lambda and iota carrageenans, furcellaran, inulin, arabinogalactan, cellulose and its derivatives, scleroglucan, psyllium, such as psyllium seed husk, mucilages and gums, e.g. commonly available vegetable gums and more particularly konjac gum, xanthan gum, guar gum (guaran gum), locust bean gum, tara bean gum, gum tragacanth, arabic gum, karaya gum, gum ghatti, gellan gum and other related sterculia gum, alfalfa, clover, fenugreek, tamarind flour. Native and modified, e.g. hydrolyzed, soluble fibers may be used.

In some preferred embodiments of the present invention, the nutritional composition contains one or more food acids selected from the group consisting of citric acid, malic acid, tartaric acid, acetic acid, benzoic acid, butyric acid, lactic acid, fumaric acid, succinic acid, ascorbic acid, adipic acid, phosphoric acid, and mixtures thereof.

In an embodiment of the present invention, the nutritional composition furthermore comprises a flavour selected from the group consisting of salt, flavourings, flavour enhancers and/or spices. In a preferred embodiment of the invention, the flavour comprises chocolate, lemon, orange, lime, strawberry, banana, forest fruit flavour or combinations thereof. The choice of flavour may depend on the nutritional composition to be produced.

If used, the total amount of flavour is typically in the range of 0.01-2% w/w. For example, the total amount of flavour may be in the range of 0.03-1.5% w/w. Alternatively the total amount of flavour may be in the range of 0.05-1.2% w/w.

In some embodiments of the invention, the nutritional composition furthermore comprises at least one high intensity sweetener. In one embodiment, the at least one high intensity sweetener is selected from the group consisting of aspartame, cyclamate, sucralose, acesulfame salt, neotame, saccharin, stevia extract, a steviol glycoside such as e.g.

rebaudioside A, or a combination thereof. In some embodiments of the invention, it is particularly preferred that the sweetener comprises or even consists of one or more high intensity sweeteners (HIS).

HIS are found among both natural and artificial sweeteners and typically have a sweetening intensity of at least 10 times that of sucrose. If used, the total amount of HIS is typically in the range of 0.01-2% w/w. For example, the total amount of HIS may be in the range of 0.05-1.5% w/w. Alternatively, the total amount of HIS may be in the range of 0.1-1.0% w/w.

The choice of the sweetener may depend on the composition to be produced, e.g. high-intensity sugar sweeteners (e.g. aspartame, acetsulfam-K or sucralose) may be used in compositions where no energy contribution from the sweetener is desired, whereas for compositions having a natural profile natural sweeteners (e.g. steviol glycosides, sorbitol or sucrose) may be used.

It may furthermore be preferred that the sweetener comprises or even consists of one or more polyol sweetener(s). Non-limiting examples of useful polyol sweetener are maltitol, mannitol, lactitol, sorbitol, inositol, xylitol, threitol, galactitol or combinations thereof. If used, the total amount of polyol sweetener is typically in the range of 1-20% w/w. For example, the total amount of polyol sweetener may be in the range of 2-15% w/w. Alternatively, the total amount of polyol sweetener may be in the range of 4-10% w/w.

In some embodiments of the invention, the nutritional composition furthermore comprises milk, preferably whole milk. The milk is preferably from mammal milk, and preferably from ruminant milk such as e.g. milk from cow, sheep, goat, buffalo, camel, llama, mare and/or deer. Bovine milk is particularly preferred.

The nutritional composition of the present invention may comprise other macronutrients than proteins. In some preferred embodiments of the invention, the nutritional composition furthermore comprises carbohydrates.

In one exemplary embodiment, the at least one source of carbohydrate is selected from the group consisting of: sucrose, maltodextrin, corn syrup solids, saccharose, maltose, sucromalt, maltitol powder, glycerine, glucose polymers, corn syrup, modified starches, resistant starches, rice-derived carbohydrates, isomaltulose, white sugar, glucose, fructose, lactose, high fructose corn syrup, honey, sugar alcohols, fructooligosaccharides, soy fiber, corn fiber, guar gum, konjac flour, polydextrose, Fibersol, and combinations thereof.

In some preferred embodiments of the invention, the nutritional composition comprises sugar polymers, i.e. oligosaccharides and/or polysaccharides.

In some preferred embodiments, the nutritional composition furthermore comprises carbohydrates in a range between 0 to 95% of the total energy content of the composition, preferably in a range between 10 to 85% of the total energy content of the composition, preferably in a range between 20 to 75% of the total energy content of the composition or preferably in a range between 30 to 60% of the total energy content of the composition.

Even lower carbohydrate content is often preferred, thus, in some preferred embodiments of the invention, the carbohydrate content of the nutritional composition is preferably in a range between 0 to 30% of the total energy content of the composition more preferably in a range between 0 to 20% of the total energy content of the composition even more preferably in a range between 0 to 10% of the total energy content of the composition.

In some preferred embodiments of the invention, the carbohydrate content of nutritional composition is at most 5% of the total energy content of the composition, more preferably at most 1% of the total energy content of the composition, and even more preferably at most 0.1% of the total energy content of the composition.

In one embodiment of the invention, the nutritional composition comprises a plurality of vitamins. In one exemplary embodiment, the nutritional composition comprises at least ten vitamins. In one exemplary embodiment, the nutritional composition comprises a plurality of vitamins selected from the group consisting of: Vitamin A, vitamin B1, vitamin B2, vitamin B3, vitamin B5, vitamin B6, vitamin B7, vitamin B9, vitamin B12, vitamin C, vitamin D, vitamin K, Riboflavin, pantothenic Acid, vitamin E, thiamin, niacin, folic acid, biotin, and combinations thereof.

In one embodiment of the invention, the nutritional composition comprises a plurality of vitamins and a plurality of minerals.

The nutritional composition of the present invention may comprise other macronutrients than proteins. In some embodiments of the invention, nutritional composition furthermore comprises lipids. The total lipid content in the nutritional composition of the invention depends on the intended use of the nutritional composition.

In some preferred embodiments of the invention, nutritional composition has a lipid content between 0 to 60% of the total energy content of the composition, or preferably in a range between 0 to 50% of the total energy content of the composition or preferably in a range between 0 to 45% of the total energy content of the composition, or preferably in a range between 0 to 30% of the total energy content of the composition or preferably in a range between 0 to 20% of the total energy content of the composition or preferably in a range between 0 to 10% of the total energy content of the composition or preferably in a range between 0 to 5% of the total energy content of the composition.

The amount of lipid is determined according to ISO 1211:2010 (Determination of Fat Content—Röse-Gottlieb Gravimetric Method).

In some preferred embodiments of the invention, the lipid content of the nutritional composition is at most 3% of the total energy content of the composition, more preferably at most 1% of the total energy content of the composition, and even more preferably at most 0.1% of the total energy content of the composition.

In some preferred embodiments of the present invention the composition comprises a total amount of lipid of at most 10E %, preferably at most at most 1E %.

In the context of the present invention the terms "lipid", "fat", and "oil" as used herein unless otherwise specified, are used interchangeably to refer to lipid materials derived or processed from plants or animals. These terms also include synthetic lipid materials so long as such synthetic materials are suitable for human consumption.

In the context of the present invention, the term "energy content" means the total content of energy contained in a food product. The energy content can be measured in kilojoule (kJ) or kilo calories (kcal) and are referred to as calories per amount of food product, e.g. kcal per 100 gram of the food product. One example is a composition having an energy content of 350 kcal/100 gram of the composition.

The total energy content of a food product or nutritional composition includes the energy contribution from all the macronutrients present in the food product, e.g. energy from protein, lipid and carbohydrate. The distribution of energy from the macronutrients in the food product can be calculated based on the amount of the macronutrients in the food product and the contribution of the macronutrient to the total energy content of the food product. The energy distribution can be stated as energy percent (E %) of the total energy content of the food product. For example for a composition comprising 20E % protein, 50E % carbohydrate and 30E % lipid, this means that 20% of the total energy comes from protein, 50% of the total energy comes from carbohydrate and 30% of the total energy comes from fat (lipid).

In some preferred embodiments of the present invention, when the nutritional composition is administered as a meal, it is particularly preferred that the nutritional composition is a nutritionally complete nutritional supplement and comprises preferably a total amount of lipid of less than 30E %, preferably in the range of 20-50% of the total energy content, preferably in a range between 30-40E %.

In some preferred embodiments of the present invention, the nutritionally complete nutritional supplement comprises e.g. a total amount of lipid in the range of 20-60% of the total energy content, preferably in a range between 30-50E %.

In a preferred embodiment of the invention, the nutritionally complete nutritional supplement comprises less than 30E % lipid, 20-75E % carbohydrates and 25-50E % protein.

In another preferred embodiment of the invention, the nutritionally complete nutritional supplement comprises, less than 30E % lipid, 45-80E % carbohydrates and 20-25E % protein In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating a metabolic disorder, wherein the metabolic disorder is metabolic syndrome, obesity and/or dyslipidemia and wherein the use involves increasing the level of insulin and/or glucagon in the blood of the subject.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating a metabolic disorder, wherein the metabolic disorder is metabolic syndrome, obesity and/or dyslipidemia and wherein the use involves increasing the level of insulin and/or glucagon in the blood of the subject and wherein the a) Beta-lactoglobulin or b) the nutritional composition is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating a metabolic disorder, wherein the metabolic disorder is metabolic syndrome, obesity and/or dyslipidemia and wherein the use involves increasing the level of insulin and/or glucagon in the blood of the subject and wherein a) beta-lactoglobulin or b) the nutritional composition is administered as a nutritional composition in the form of a premeal in a daily dose of 0.09-1.2 g protein/kg body weight, even more preferably in a daily dose of 0.10-1.0 g protein/kg body weight, most preferably in a daily dose of 0.20-0.90 g protein/kg body weight.

In a preferred embodiment of the present invention the a) Beta-lactoglobulin or b) a nutritional composition comprising beta-lactoglobulin in an amount of at least 75% w/w relative to total protein in a therapeutically effective amount, for use in preventing and/or treating metabolic syndrome and wherein the use involves increasing the level of insulin and/or glucagon in the blood of the subject and wherein the a) beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating obesity and wherein the use involves increasing the level of insulin and/or glucagon in the blood of the subject and wherein the a) Beta-lacto-globulin or b) a nutritional composition comprising beta-lactoglobulin in an amount of at least 75% w/w relative to total protein is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating dyslipidemia and wherein the use involves increasing the level of insulin and/or glucagon in the blood of the subject and wherein the a) Beta-lactoglobulin or b) a nutritional composition comprising beta-lactoglobulin in an amount of at least 75% w/w relative to total protein is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating a metabolic disorder, wherein the metabolic disorder is metabolic syndrome, obesity and/or dyslipidemia and wherein the use involves increasing the level of insulin, glucagon, GIP and/or GLP-1 in the blood of the subject.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating muscle atrophy, wherein the muscle atrophy is sarcopenia, cachexia, malnutrition and/or immobility/reduced physical activity and wherein the use involves increasing the level of insulin and/or glucagon in the blood of the subject.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating muscle atrophy, wherein the muscle atrophy is sarcopenia, cachexia, malnutrition and/or immobility/reduced physical activity and wherein the use involves increasing the level of insulin and/or glucagon in the blood of the subject and wherein the a) Beta-lactoglobulin or the b) nutritional composition is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating muscle atrophy, wherein the muscle atrophy is sarcopenia, cachexia, malnutrition and/or immobility/reduced physical activity and wherein the use involves increasing the level of insulin and/or glucagon in the blood of the subject and wherein the BLG is administered as a nutritional composition in the form of a premeal in a daily dose of 0.09-1.2 g protein/kg body weight, even more preferably in a daily dose of 0.10-1.0 g protein/kg body weight, most preferably in a daily dose of 0.20-0.90 g protein/kg body weight.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating muscle atrophy wherein the use involves increasing the level of insulin and/or glucagon in the blood of the subject and wherein the a) Beta-lactoglobulin or the b) nutritional composition is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating cachexia and wherein the use involves increasing the level of insulin and/or glucagon in the blood of the subject and wherein the a) Beta-lactoglobulin or the b) nutritional composition is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating malnutrition and/or immobility/reduced physical activity and wherein the use involves increasing the level of insulin and/or glucagon in the blood of the subject and wherein the a) Beta-lactoglobulin or the b) nutritional composition is administered as a pre-meal, preferably 0-60 minutes prior to a meal, even more preferred 0-30 minutes prior to a meal.

In a preferred embodiment of the present invention the a) Beta-lactoglobulin or b) a nutritional composition comprising beta-lactoglobulin in an amount of at least 75% w/w relative to total protein, more preferably at least 85 w/w % relative to total protein, more preferably at least 90% w/w relative to total protein in a therapeutically effective amount, for use in preventing and/or treating muscle atrophy, wherein the muscle atrophy is sarcopenia, cachexia, malnutrition and/or immobility/reduced physical activity and wherein the use involves increasing the level of insulin, glucagon, GIP and/or GLP-1 in the blood of the subject.

In a preferred embodiment of the present invention, the beta lactoglobulin for use in preventing and/or treating diabetes, preferably type 2 diabetes in a human being, wherein the use involves increasing the level of insulin and/or GIP in the blood.

In a preferred embodiment of the present invention, the beta lactoglobulin for use in preventing and/or treating diabetes, preferably type 2 diabetes, in a human being, wherein the beta lactoglobulin is administered in the form of a nutritional composition wherein the nutritional composition comprises a total amount of protein of at least 1.0 wt % relative to the weight of the nutritional composition and wherein at least 90 wt % of the protein is beta-lactoglobulin.

In a preferred embodiment of the present invention, the beta-lactoglobulin for use in preventing and/or treating diabetes in a human being, wherein the beta-lactoglobulin is administered in the form of a nutritional composition in a serving dose of at least 0.05 g protein/kg body weight, even more preferably at least 0.06 g protein/kg body weight, most preferably at least 0.07 g protein/kg body weight.

In a preferred embodiment of the present invention, the beta-lactoglobulin for use in preventing and/or treating diabetes, preferably types 2 diabetes, in a human being, wherein the beta-lactoglobulin is administered in the form of a nutritional composition in a daily dose of at least 0.15 g protein/kg body weight, even more preferably at least 0.18 g protein/kg body weight, most preferably at least 0.20 g protein/kg body weight.

In a preferred embodiment of the present invention, the beta-lactoglobulin for use in preventing and/or treating diabetes in a human being, wherein the beta-lactoglobulin is administered in the form of a nutritional composition in a serving dose of 0.03-0.40 g protein/kg body weight, even more preferably in a serving dose of 0.05-0.35 g protein/kg body weight, most preferably in a serving dose of 0.07-0.30 g protein/kg body weight.

In a preferred embodiment of the present invention, the beta-lactoglobulin for use in preventing and/or treating diabetes, preferably types 2 diabetes, in a human being, wherein the beta-lactoglobulin is administered in the form of a nutritional composition in a daily dose of 0.09-1.2 g protein/kg body weight, even more preferably in a daily dose of 0.10-1.0 g protein/kg body weight, most preferably in a daily dose of 0.20-0.90 g protein/kg body weight.

In a preferred embodiment of the present invention, the beta-lactoglobulin for use in preventing and/or treating diabetes, preferably types 2 diabetes, in a human being, wherein the beta lactoglobulin is administered as a pre-meal, wherein the pre-meal essentially consist of protein, preferably of BLG.

In a preferred embodiment of the present invention, the beta-lactoglobulin for use in preventing and/or treating diabetes, preferably types 2 diabetes, in a human being, wherein the beta-lactoglobulin is administered as a pre-meal, wherein the pre-meal furthermore comprises at least one additional ingredient selected from the group consisting of vitamins, flavouring agent, minerals, sweeteners, antioxidants, food acid, lipids, carbohydrate, prebiotics, probiotics, whole milk and non-whey protein or a combination thereof.

In a preferred embodiment of the present invention, the beta-lactoglobulin for use in preventing and/or treating diabetes, preferably types 2 diabetes, in a human being, wherein the beta-lactoglobulin is administered as a pre-meal, wherein the pre-meal furthermore comprises a flavouring agent and/or a high intensity sweetener.

In a preferred embodiment of the present invention, the beta-lactoglobulin for use in preventing and/or treating diabetes, preferably types 2 diabetes, in a human being, wherein the beta-lactoglobulin is administered as a pre-meal 0-90 minutes prior to a meal, preferably 5-70 minutes prior to a meal, more preferably 10-50 minutes prior to a meal, even more preferably 20-30 minutes prior to a meal.

In a preferred embodiment of the present invention, the beta-lactoglobulin for use in preventing and/or treating diabetes in a human being, wherein the beta-lactoglobulin is administered in the form of a nutritional composition that comprises less than 30E % lipid, 20-75E % carbohydrates and 25-50E % protein.

In a preferred embodiment of the present invention, the beta lactoglobulin for use in preventing and/or treating diabetes in a human being, wherein the beta lactoglobulin is administered in the form of a nutritional composition that comprises less than 30E % lipid, 45-80E % carbohydrates and 20-25E % protein.

In a preferred embodiment of the present invention, the beta-lactoglobulin for use in preventing and/or treating diabetes in a human being, wherein the beta-lactoglobulin is administered in the form of a nutritional composition as a pre-meal 0-90 minutes prior to a meal, preferably 5-70 minutes prior to a meal in a serving dose of 0.03-0.40 g protein/kg body weight, even more preferably in a serving dose of 0.05-0.35 g protein/kg body weight, most preferably in a serving dose of 0.07-0.30 g protein/kg body weight.

In a preferred embodiment of the present invention, the beta-lactoglobulin for use in preventing and/or treating diabetes, preferably types 2 diabetes in a human being, wherein the beta-lactoglobulin is administered in the form of a nutritional composition as a pre-meal 0-90 minutes prior to a meal, preferably 5-70 minutes prior to a meal in a serving dose of 0.03-0.40 g protein/kg body weight, even more preferably in a serving dose of 0.05-0.35 g protein/kg body weight, most preferably in a serving dose of 0.07-0.30 g protein/kg body weight.

In a preferred embodiment of the present invention, the beta-lactoglobulin for use in preventing and/or treating diabetes, preferably types 2 diabetes in a human being, wherein the beta-lactoglobulin is administered in the form of a nutritional composition that comprises a total amount of protein of at least 1.0 wt % relative to the weight of the nutritional composition and wherein at least 90 wt % of the protein is beta-lactoglobulin, said composition is administered as a premeal 0-90 minutes prior to a meal, preferably 5-70 minutes prior to a meal in a serving dose of 0.03-0.40 g protein/kg body weight, even more preferably in a serving dose of 0.05-0.35 g protein/kg body weight, most preferably in a serving dose of 0.07-0.30 g protein/kg body weight.

An aspect of the invention pertains to a nutritional composition as defined herein for use in preventing and/or treating diabetes or prediabetes in a subject, wherein the nutritional composition comprises a total amount of protein of at least 1.0 wt % relative to the weight of the nutritional composition, wherein at least 75 wt % of the protein is beta-lactoglobulin.

An aspect of the present invention pertains to a method of treating and/or preventing diabetes or prediabetes in a subject, the method comprising: administering BLG to the subject to treat and/or prevent diabetes or prediabetes.

An aspect of the present invention pertains to BLG for use in treatment and/or prevention of diabetes or prediabetes in a subject.

Another aspect of the present invention pertains to use of BLG in the manufacture/preparation of a medicament for the treatment and/or prevention of diabetes or prediabetes in a subject.

It should be noted that the embodiments and features described in the context of one of the aspects of the present invention also apply to the other aspects of the invention.

All patent and non-patent references cited in the present application are hereby incorporated by reference in their entirety.

The invention will now be described in further details in the following non-limiting examples.

EXAMPLES

Example 1.1

Determination of the Degree of Protein Denaturation of a Whey Protein Composition Denatured whey protein is known to have a lower solubility at pH 4.6 than at pH values below or above pH 4.6, therefore the degree of denaturation of a whey protein composition is determined by measuring the amount of soluble protein at pH 4.6 relative to the total amount of protein at a pH where the proteins in the solution are stable.

More specifically for whey proteins, the whey protein composition to be analysed (e.g. a powder or an aqueous solution) is converted to:

a first aqueous solution containing 5.0% (w/w) total protein and having a pH of 7.0 or 3.0, and a second aqueous solution containing 5.0% (w/w) total protein and having a pH of 4.6.

pH adjustments are made using 3% (w/w) NaOH (aq) or 5% (w/w) HCl (aq).

The total protein content ($P_{pH\ 7.0\ or\ 3.0}$) of the first aqueous solution is determined according to example 1.3.

The second aqueous solution is stored for 2 hours at room temperature and subsequently centrifuged at 3000 g for 5 minutes. A sample of the supernatant is recovered and analysed according to Example 1.3 to give the protein concentration in the supernatant ($S_{pH\ 4.6}$).

The degree of protein denaturation, D, of the whey protein composition is calculated as:

$$D=((P_{pH\ 7.0\ or\ 3.0}-S_{pH\ 4.6})/P_{pH\ 7.0\ or\ 3.0})*100\%$$

Example 1.2

Determination of Protein Denaturation (with pH 4.6 Acid Precipitation) Using Reverse Phase UPLC Analysis BLG samples were diluted to 2% in MQ water. 5 mL protein solution, 10 mL Milli-Q, 4 mL 10% acetic acid and 6 mL 1.0M NaOAc are mixed and stirred for 20 minutes to allow precipitation agglomeration of denatured protein around pH 4.6. The solution is filtered through 0.22 μm filter to remove agglomerates and non-native proteins.

All samples were subjected to the same degree of dilution by adding polished water.

For each sample, the same volume was loaded on an UPLC system with a UPLC column (Protein BEH C4; 300 Å; 1.7 µm; 150×2.1 mm) and detected at 214 nm.

The samples were run using the following conditions:

Buffer A: Milli-Q water, 0.1% w/w TFA

Buffer B: HPLC grade acetonitrile, 0.1% w/w TFA

Flow: 0.4 ml/min

Gradient: 0-6.00 minutes 24-45% B; 6.00-6.50 minutes 45-90% B; 6.50-7.00 minutes 90% B; 7.00-7.50 minutes 90-24% B and 7.50-10.00 minutes 24% B.

The area of BLG peaks against a protein standard (Sigma L0130) was used to determine the concentration of native bLG in samples (5 level calibration curve).

Samples were diluted further and reinjected if outside linear range.

Example 1.3

Determination Total Protein

The total protein content (true protein) of a sample is determined by:

1) Determining the total nitrogen of the sample following ISO 8968-1/2 ÅIDF 020-1/2-Milk—Determination of nitrogen content—Part 1/2: Determination of nitrogen content using the Kjeldahl method.

2) Determining the non-protein nitrogen of the sample following ISO 8968-4 ÅIDF 020-4-Milk—Determination of nitrogen content—Part 4: Determination of non-protein-nitrogen content.

3) Calculating the total amount protein as $(m_{total\ nitrogen} - m_{non-protein-nitrogen})*6.38$.

Example 1.4

Determination of Non-Aggregated BLG, ALA, AND CMP

The content of non-aggregated alpha-lactalbumin (ALA), beta-lactoglobulin (BLG) and caseinomacropeptide (CMP), respectively was analysed by HPLC analysis at 0.4 mL/min. 25 microL filtered sample is injected onto 2 TSKgel3000PWxI (7.8 mm 30 cm, Tosohass, Japan) columns connected in series with attached pre-column PWxl (6 mm×4 cm, Tosohass, Japan) equilibrated in the eluent (consisting of 465 g Milli-Q water, 417.3 g acetonitrile and 1 mL triflouroacetic acid) and using a UV detector at 210 nm.

Quantitative determination of the contents of native alpha-lactalbumin ($C_{alpha}$), beta-lactoglobulin ($C_{beta}$), and caseinomacropeptide ($C_{CMP}$) was performed by comparing the peak areas obtained for the corresponding standard proteins with those of the samples.

The total amount of additional protein (non-BLG protein) was determined by subtracting the amount of BLG from the amount of total protein (determined according to Example 1.3)

Example 1.5

Determination of Ash Content

The ash content of a food product is determined according to NMKL 173:2005 "Ash, gravimetric determination in foods".

Example 1.6

Determination of the Total Solids of a Solution

The total solids of a solution may be determined according NMKL 110 $2^{nd}$ Edition, 2005 (Total solids (Water)—Gravimetric determination in milk and milk products). NMKL is an abbreviation for "Nordisk Metodikkomité for Næringsmidler".

The water content of the solution can be calculated as 100% minus the relative amount of total solids (% w/w).

Example 1.7

Determination of pH

All pH values are measured using a pH glass electrode and are normalised to 25 degrees Celsius.

The pH glass electrode (having temperature compensation) is rinsed carefully before and calibrated before use.

When the sample is in liquid form, then pH is measured directly in the liquid solution at 25 degrees Celsius.

When the sample is a powder, 10 gram of a powder is dissolved in 90 ml of demineralised water at room temperature while stirring vigorously. The pH of the solution is then measured at 25 degrees Celsius.

Example 1.8

Determination of the Water Content of a Powder

The water content of a food product is determined according to ISO 5537:2004 (Dried milk—Determination of moisture content (Reference method)). NMKL is an abbreviation for "Nordisk Metodikkomité for Næringsmidler".

Example 1.9

Determination of the Total Amount of Lactose

The total amount of lactose is determined according to ISO 5765-2:2002 (IDF 79-2: 2002) "Dried milk, dried ice-mixes and processed cheese—Determination of lactose content—Part 2: Enzymatic method utilizing the galactose moiety of the lactose".

Example 1.10

Determination of the Total Amount of Carbohydrate

The amount of carbohydrates in a beverage is determined by use of Sigma Aldrich Total Carbohydrate Assay Kit (Cat MAK104-1KT) in which carbohydrates are hydrolysed and converted to furfural and hydroxyfurfurals which are converted to a chromagen that is monitored spectrophotometrically at 490 nm.

Example 1.11

Determination of the Total Amount of Lipids

The amount of lipid is determined according to ISO 1211:2010 (Determination of Fat Content—Röse-Gottlieb Gravimetric Method).

Example 1.12

Determination of Brix

Brix measurements were conducted using a PAL-α digital hand-held refractometer (Atago) calibrated against polished water (water filtered by reverse osmosis to obtain a conductivity of at most 0.05 mS/cm).

Approx. 500 µl of sample was transferred to the prism surface of the instrument and the measurement was started. The measured value was read and recorded.

The Brix of a whey protein solution is proportional to the content of total solids (TS) and TS (% w/w) is approx. Brix*0.85.

Example 1.13

Determination of Plasma Glucose

Plasma glucose concentrations were measured using a glucose laboratory instrument intended for use in clinical care and sports medicine applications. For this study we used the instrument: YSI 2300 model Stat Plus (Bie & Berntsen).

Plasma glucose concentrations were analysed immediately after sampling, whereas samples for insulin, GIP, GLP-1 and glucagon measurements were frozen immediately after sampling and kept at minus 80 degrees Celsius until study completion. Thereafter samples were batch-analysed.

Example 1.14

Determination of Serum Insulin

Serum insulin concentrations were analysed using ELISA (Mercodia Insulin ELISA, Sweden).

Example 1.15

Determination of Plasma Glucagon

Plasma glucagon concentrations were analysed by radio-immunoassay (EMD Millipore's Glucagon Radioimmuno-assay (RIA) Kit, Germany).

Example 1.16

Determination of GLP-1 and GIP

Blood was collected for determining total GLP-1 and GIP into chilled tubes containing EDTA (7.4 mmol/liter) and were kept at minus 80 degrees Celsius until analysis.

GLP-1 concentrations were determined with radioimmunoassay (RIA) using a C-terminally directed antiserum (code no. 89390) for total GLP-1 (Orskov C, Rabenhøj L, Wettergren A, Kofod H, Holst J J. Tissue and plasma concentrations of amidated and glycine-extended glucagon-like peptide I in humans. Diabetes. 1994 April; 43(4):535-9).

Total GIP was analyzed using a C-terminally directed antiserum (code no. 80867) raised in rabbits immunized with a C-terminal fragment of GIP [GIP (28-42)] conjugated to keyhole limpet hemocyanin via its N-terminus (Lindgren O, Carr R D, Deacon C F, et al. Incretin hormone and insulin responses to oral versus intravenous lipid administration in humans. J Clin Endocrinol Metab 2011; 96:2519-2524).

Example 1.17

Determination of Leucine and Total Plasma Essential Amino Acid Concentration After deproteination with methanol aliquots of the supernatant were added to 100 µL of an internal standard mixture (isotope labelled amino acids) and dried under nitrogen. After derivatization, the samples were dried with $N_2$ again and reconstituted with mobile phase.

10 µl of these samples were injected and separated over 25 minutes with a C18-HPLC column running a gradient profile. The measurement was done with a Tandem Mass Spectrometer in ESI mode. The amino acids were measured in MRM-mode and quantitated using the corresponding/appropriate internal standard and calibrated against certificated reference materials.

With every batch, a set of certificated control materials were measured to ensure the quality standards. Total plasma amino acid concentrations were calculated by adding values of all 21 essential amino acids in the blood.

The used internal standards are:

| | |
|---|---|
| 2-Aminobutyric acid | Glycine (2-$^{13}$C,$^{15}$N) |
| Alanine | L-Alanine (2,3,3,3 -D$_4$) |
| Arginine | L-Arginine:HCl (5-$^{13}$C, 4,4,5,5 -D$_4$) |
| Asparagine | Glycine (2-$^{13}$C,$^{15}$N) |
| Aspartic acid | L-Aspartic Acid (2,3,3-D$_3$) |
| Citrulline | L-Citrulline (5,5-D$_2$) |
| Cystine | L-Valine (D$_8$) |
| Glutamic acid | DL-Glutamic Acid (2,4,4-D$_3$) |
| Glutamine | Glycine (2-$^{13}$C,$^{15}$N) |
| Glycine | Glycine (2-$^{13}$C,$^{15}$N) |
| Histidine | Glycine (2-$^{13}$C,$^{15}$N) |
| Hydroxyproline | L-Alanine (2,3,3,3 -D$_4$) |
| Isoleucine | L-Leucine (5,5,5-D$_3$) |
| Leucine | L-Leucine (5,5,5-D$_3$) |
| Lysine | Glycine (2-$^{13}$C,$^{15}$N) |
| Methionine | L-Methionine (methyl-D$_3$) |
| Ornithine | L-Ornithine:HCl (5,5-D$_2$) |
| Phenylalanine | L-Phenylalanine (ring-$^{13}$C$_6$) |
| Proline | L-Alanine (2,3,3,3 -D$_4$) |
| Serine | Glycine (2-$^{13}$C,$^{15}$N) |
| Threonin | Glycine (2-$^{13}$C,$^{15}$N) |
| Tyrosine | L-Tyrosine (ring-$^{13}$C$_6$) |
| Valine | L-Valine (D$_8$) |

Example 1.18

Determination of the Amount of BLG, ALA, and CMP

This procedure is a liquid chromatographic (HPLC) method for the quantitative analysis of proteins such as ALA, BLG and CMP and optionally also other protein species in a composition. Contrary to the method of Example 1.4, the present method also measures proteins that are present in aggregated and therefore provides a measure of the total amount of the protein species in the composition in question.

The mode of separation is Size Exclusion Chromatography (SEC) and the method uses 6M Guanidine HCl buffer as both sample solvent and HPLC mobile phase. Mercaptoethanol is used as a reducing agent to reduce the disulphide (S—S) in the proteins or protein aggregates to create unfolded monomeric structures.

The sample preparation is easily achieved by dissolving 10 mg protein equivalent in the mobile phase.

Two TSK-GEL G3000SWXL (7.7 mm×30.0 cm) columns (GPC columns) and a guard column are placed in series to achieve adequate separation of the major proteins in raw materials.

The eluted analytes are detected and quantified by UV detection (280 nm).

Equipment/Materials:

1. HPLC Pump 515 with manual seal wash (Waters)
2. HPLC Pump Controller Module II (Waters)
3. Autosampler 717 (Waters)
4. Dual Absorbance Detector 2487 (Waters)
5. Computer software capable of generating quantitative reports (Empower 3, Waters)
6. Analytical column: Two TSK-GEL G3000SWXL (7.8× 300 mm, P/N: 08541). Guard Column: TSK-Guard Column SWxL (6.0×40 mm, P/N: 08543).
7. Ultrasonic Bath (Branson 5200)
8. 25 mm Syringe filter with 0.2 μm Cellulose Acetate membrane. (514-0060, VWR)

Procedure:

Mobile Phase:

A. Stock Buffer Solution.

1. Weigh 56.6 g of $Na_2HPO_4$, 3.5 g of $NaH_2PO_4$, and 2.9 g of EDTA in to a 1000 mL beaker. Dissolve in 800 mL of water.
2. Measure pH and adjust to 7.5±0.1, if necessary, with HCl (decrease pH) or NaOH (increase pH).
3. Transfer to a 1000 mL volumetric flask and dilute to volume with water.

B. 6M Guanidine HCl Mobile Phase.

1. Weigh 1146 g of Guanidine HCl in to a 2000 mL beaker, and add 200 mL of the stock buffer solution(A)
2. Dilute this solution to about 1600 mL with water while mixing with a magnetic stir bar (50° C.)
3. Adjust the pH to 7.5±0.1 with NaOH.
4. Transfer into a 2000 mL volumetric flask and dilute to volume with water.
5. Filter using the solvent filtration apparatus with the 0.22 μm membranefilter.

Calibration Standards.

Calibration Standards of Each Protein to be Quantified are Prepared the Following Way:

1. Weigh accurately (to 0.01 mg) about 25 mg of the protein reference standard into a 10 mL volumetric flask and dissolve in 10 mL of water.
   This is the protein stock standard solution (51) of the protein
2. Pipette 200 μl of S1 into a 20 ml volumetric flask and dilute to volume with mobile phase. This is the low working standard solution WS1.
3. Pipette 500 μL of S1 into a 10 mL volumetric flask and dilute to volume with mobile phase. This is standard solution WS2.
4. Pipette 500 μL of S1 into a 5 mL volumetric flask and dilute to volume with mobile phase. This is standard solution WS3.
5. Pipette 750 μL of S1 into a 5 mL volumetric flask and dilute to volume with mobile phase. This is standard solution WS4.
6. Pipette 1.0 mL of S1 into a 5 mL volumetric flask and dilute to volume with mobile phase. This is the high working standard solution WS5.
7. Using graduated disposable pipettes transfer 1.5 mL of WS1-5 into separate vials. Add 10 μL of 2-mercaptoethanol to each vial and cap. Vortex the solutions for 10 sec. Let the standards stay at ambient temperature for about 1 hr.

8. Filter the standards using 0.22 μm Cellulose Acetate syringe filters.

The purity of protein is measured using Kjeldahl (N×6.38) and the area % from standard solution WS5 using the HPLC.

$$protein\ (mg)=\text{"protein standard weight"}\ (mg)×P1×P2$$

P1=P % (Kjeldahl)

P2=protein area % (HPLC)

Sample Preparation

1. Weigh the equivalent of 25 mg of protein of the original sample into a 25 mL volumetric flask.
2. Add approximately 20 mL of mobile phase and let the sample dissolve for about 30 min.
3. Add mobile phase to volume and add 167 μL of 2-mercaptoethanol to the 25 ml sample solution.
4. Sonicate for about 30 min and afterwards let the sample stay at ambient temperature for about 1½ hours.
5. Mix the solution and filter using 0.22 μl Cellulose Acetate syringe filters.

HPLC System/Columns

Column Equilibration

1. Connect the GPC guard column and the two GPC analytical columns in series.
   New columns are generally shipped in a phosphate-salt buffer.
2. Run water through a new column gradually from 0.1 to 0.5 mL/min in 30 to 60 mins.
   Continue flushing for about 1 hour.
3. Gradually decrease flow rate from 0.5 mL/min to 0.1 mL/min and replace with mobile phase in the reservoir.
4. Increase pump flow rate gradually from 0.1 to 0.5 mL/min in 30 to 60 mins to avoid pressure shock and leave at 0.5 mL/min.
5. Inject ten samples to allow the column to be saturated and wait for the peaks to elute.
   This will aid in the conditioning of the column.
   This step is done without the need of waiting for each injection to be complete before injecting the next.
6. Equilibrate with the mobile phase at least 1 hour.

Calculation of the Results

Quantitative determination of the contents of the proteins to be quantified, e.g. alpha-lactalbumin, beta-lactoglobulin, and caseinomacropeptide, is performed by comparing the peak areas obtained for the corresponding standard proteins with those of the samples. The results are reported as g specific protein/100 g of the original sample or weight percentage of the specific protein relative to the weight of the original sample.

Example 2

Preparation of Generic Nutritional Compositions Comprising Whey Protein

Dried BLG isolate protein powders containing ≥85% BLG on protein basis are dispersed in up to about 95% of the demineralized water required to reach a desired final protein concentration.

Acidic BLG isolate powders is produced as outlined in example 2 of PCT/EP2019/067015 while pH 5.5 BLG isolate powder are produced as outlined in example 7 of (PCT/EP2017/084553) WO2018115520 (A1).

As described in WO2018115520 (A1) (PCT/EP2017/ 084553), dissolution of BLG material may be aided by addition of acid, base, or salt (selected among one or more food-grade acid, bases or salts, such as phosphoric acid, hydrochloric acid, citric acid, malic acid or salts in their dissolved or powder forms). If pH is reduced during disso-
lution by acid addition, the pH should preferably not pass
desired target pH (i.e. avoid unnecessary titration with acid
and/or base).

Optionally, minerals, sweeteners, flavours, stabilizers,
emulsifiers or other components can be added also including
sources of fats and carbohydrates. The employed process
comprises the following steps:

In case fat is included then first heat oil to 70° C. in water
bath,

Mix with emulsifier (typically to 0.2 w/w % in final
recipe); for example the emulsifier Grindsted Citrem
LR10 which is a citric acid ester, recommended for
phosphate-free applications. Allow to cool to 60° C. (to
avoid/reduce potential denaturation/aggregation when
mixed with protein)

Mix slowly with preheated water (60° C.)

Add all powdered ingredients in premixed form (to avoid
'fisheyes'); this includes premixing of carbohydrates
and protein, Optionally add minerals (NaCl, KCl, CaCl2 and MgCl2)
to achieve the desired concentrations of Na, K, Ca and
Mg. Minerals were dissolved in demineralized water
and added to reach desired concentrations of Na, K, Ca
and Mg. Other food grade minerals may further be used
and added in dissolved or powder forms.

Adjust pH if necessary to final pH using up to 10%
phosphoric acid (or other food grade acid) or up to 10%
NaOH.

Remaining water is added to reach desired protein con-
centration and the composition is optionally homog-
enized ('upstream homogenization').

Optionally, subject the composition to heat-treatment

Optionally homogenize ('downstream homogenization').

Samples were stored at 20° C. in a dark environment.

Example 3

Preparation of Isocaloric, Isonitrogenous Beverages

For testing the insulinotropic effects of different milk
proteins, three different beverages comprising respectively,
at least 85% Beta-lactoglobulin of total protein (BLG),
Casein (CAS) and Whey protein (WHE) were prepared.

The employed process comprises the following steps:

Mix all dry ingredients

Add water to a suitable container (preferably a shaker
with a spiral wire)

Add the powder to water

Shake/mix until homogenous (about 15-30 seconds)

The composition of the three samples is shown in table 1
and 2 below.

For the BLG sample a pH 5.5 BLG crystal powder was
used, it comprises 98.6% BLG of total protein and has a
water content of 3.43. It has a degree of protein denaturation
0.84% (measured according to example 1.1).

The pH 5.5 BLG crystal powder is produced as outlined
in example 7 of (PCT/EP2017/084553) WO2018115520
(A1).

For the comparison, whey protein isolate (Lacprodan
DI-9224, Arla food ingredients) or caseinate (Na caseinate
Miprodan 30, Arla food ingredients replace the 98.6% BLG
product in the making of reference samples while preserving
remaining steps.

Whey protein isolate (WPI) comprises a number of dif-
ferent proteins and peptides, including beta-lactoglobulin,
alpha-lactalbumin, serum albumin, immunoglobulines, lactoferrin, proteose peptone 3, osteopontin, glycomacropep-
tide, lactoperoxidase, lysozyme, cathepsin D, acid phos-
phatase, ribonucleases.

TABLE 1

Composition of three isocaloric, isonitrogenous
beverage shakes; BLG, CAS and WHE.

|  | BLG (wt %) | Cas (Casein) (wt %) | WHE (WPI) (wt %) |
|---|---|---|---|
| PSNU30200, pH 5.4 BLG Crystal powder % | 10.7 | 0 | 0 |
| Na Caseinate, Miprodan 30, Aria foods ingredient) % | 0 | 11 | 0 |
| WPI-1 (Lacprodan DI-9224, Aria foods ingredient) % | 0 | 0 | 11.3 |
| Acesulfame K Sunett % | 0.13 | 0.13 | 0.13 |
| Orange Flavor (pow-der) SC649946 IFF % | 0.08 | 0.08 | 0.08 |
| WMP % (Whole milk powder Arla 26%) | 0.2 | 0 | 0 |
| Water, tap % | 88.9 | 88.8 | 88.5 |
| Total % | 100 | | |
| Total dry matter (%) | 11.1 | 11.2 | 11.5 |

TABLE 2

Composition of three isocaloric, isonitrogenous beverages
(shakes) BLG, CAS and WHE.

|  | BLG | Cas (Casein) | WHE (WPI) |
|---|---|---|---|
| Protein wt % | 10.1 | 10.1 | 10.1 |
| Fat wt % | 0.05 | 0.09 | 0.23 |
| Carbohydrates wt % | 0.14 | 0.08 | 0.08 |
| Total_Solids wt % | 10.6 | 10.6 | 10.8 |
| Lactose wt % | 0.08 | 0.03 | 0.02 |
| Calcium wt % | 0.01 | 0.02 | 0.01 |
| Energy_kJ/100 g | 175.9 | 176.0 | 180.7 |
| Energy_kcal/100 g | 41.4 | 41.4 | 42.6 |

Example 4

Investigation of the Insulinotropic Effects of Beta-Lactoglobulin, Casein and Whey Following Endotoxemia Methods:

Participants:

Participants eligible for the study were of male gender,
healthy and without regular intake of medication, had a body
mass index (BMI) between 20-30 kg*m$^{-2}$, were between 20
to 40 years of age. Participants underwent blood-screen-test,
an electrocardiography, a medical interview and a physical
examination prior to the study. Participants were without
febrile illness at least seven days before each study. They
were requested not to exercise 48 hours prior to the study, eat
a normal meal the night before the study (the comprised
protein 10-20%, fat max 30%, carbohydrates 50-60%) and
then fast from 10.00 PM.

Study Design:

The study used a double-blinded, randomized, crossover
design including 10 healthy, lean, male participants. Partici-
pants were investigated on three different occasions with 6-8
weeks apart.

To mimic disease conditions a validated catabolic inflammatory model was used. The model comprised inflammation using 1 ng lipopolysaccharide (LPS) of *E. coli*/kg bodyweight followed by 36 hours of fast and bedrest. Thereby, the model combines two catabolic models i.e. "Amino acid supplementation is anabolic during the acute phase of endotoxin-induced inflammation: A human randomized crossover trial", Rittig N, Bach E, Thomsen H H, Johannsen M, Jørgensen J O, Richelsen B, Jessen N, Møller N. Clin Nutr. 2016 April; 35(2):322-330. doi: 10.1016/j.clnu.2015.03.021. Epub 2015 Apr. 9. PMID: 25896101, and "Anabolic effects of leucine-rich whey protein, carbohydrate, and soy protein with and without beta-hydroxy-beta-methylbutyrate (HMB) during fasting-induced catabolism: A human randomized crossover trial", Rittig et al, Clin Nutr. 2017 June; 36(3): 697-705. doi: 10.1016/j.clnu.2016.05.004. Epub 2016 May 25.

The catabolic inflammatory model used, effectively induced insulin resistance, with a decrease in insulin sensitivity of 41% compared with healthy conditions (an overnight fast) using the golden standard clamp methodology.

In the current study, each visit consisted of two consecutive days (a pre-study day and a study day, see flowchart on FIG. 1). Participants arrived by taxi after an overnight fast before LPS was intravenously administered, fasting continued and bedrest initiated. Participants stayed overnight at the hospital to ensure bedrest and fasting.

On the study day three isocaloric, isonitrogenous (0.6 g protein/kg bodyweight) beverages were given. The samples were prepared as described in example 3. One third (⅓) was given as a bolus and the remaining (⅔) as sip every 20 minutes (See flowchart, FIG. 1).

The three different interventions were:
1) "Inflammation+36 hour fasting and bedrest"+Beta-Lactoglobulin (BLG)
2) "Inflammation+36 hour fasting and bedrest"+Casein (CAS)
3) "Inflammation+36 hour fasting and bedrest"+Whey proteins (WHE)

The exact ingredients of BLG, CAS and WHE are shown in table 3.

TABLE 3

Amino acid composition of the three isocaloric, isonitrogenous beverages.

| | BLG (g/100 g protein) | CAS (g/100 g protein) | WHE (g/100 g protein) |
|---|---|---|---|
| Methionine | 3.10 | 2.97 | 2.55 |
| Cysteine + Cystine | 2.69 | 0.40 | 2.38 |
| Lysine | 12.36 | 8.63 | 10.99 |
| Threonine | 5.34 | 4.59 | 8.09 |
| Isoleucine | 6.40 | 5.38 | 7.23 |
| Leucine | 16.05 | 10.00 | 12.19 |
| Histidin | 1.64 | 3.00 | 1.70 |
| Phenylalanin | 3.65 | 5.46 | 3.25 |
| Tyrosine | 3.74 | 5.80 | 3.09 |
| Valine | 6.09 | 6.96 | 6.61 |
| Alanine | 7.02 | 3.16 | 6.16 |
| Arginine | 2.71 | 3.81 | 2.35 |
| Asparagin acid | 11.93 | 7.63 | 12.19 |
| Glutamin acid, total | 19.74 | 23.04 | 19.77 |
| Glycine | 1.37 | 1.91 | 1.64 |
| Hydroxyprolin | <0.05 | <0.05 | <0.05 |
| Ornitine | <0.05 | <0.05 | <0.05 |
| Proline | 5.11 | 11.58 | 6.78 |
| Serine | 3.89 | 6.12 | 5.33 |
| Tryptophan | 2.23 | 1.37 | 1.93 |

During the study day, a catheter was inserted into the dorsal vein of the hand and heated in a warming cloth to mimic arterialized blood for blood sampling.

Randomization:
Participants were randomized using a computerized randomization system by the primary investigator.

Lipopolysaccharide (LPS):
Intravenous bolus injection of LPS (1 ng/kg bodyweight) of *E. coli* endotoxin (10,000 USP Endotoxin, lot HOK354; The United States Pharmacopeia Convention, Inc., Rockville, Maryland) was infused during two minutes at t=−24 hours on the pre-study day followed by 10 ml saline infusion. The injection of LPS caused transient rise in axillary temperature (1.7 degrees Celsius) and heart rate (25 beats/min) with various degrees of headache, nausea, shivering and muscle pain and caused elevated C-reactive peptide on the study day, which is a marker of the late phase of inflammation.

Blood Sample Analysis
Blood samples were stored at minus 80 degrees Celsius and then analysed in the same assay after study completion to minimize analytic variation.

The plasma glucose (example 1.13), serum insulin (example 1.14), plasma glucagon (example 1.15), plasma GIP and GLP-1 (example 1.16), Total plasma amino acid concentrations (example 1.17) and plasma leucine concentrations (example 1.17) were measured.

Statistics:
For the figures and statistical analysis, Sigma Plot 11 (San Jose, California, USA) and STATA 13 (College Station, Texas, USA) were used. QQ-plots were inspected to ensure normal distribution of data. If data were not normally distributed or showed variance heterogeneity, logarithmic transformation was performed. Data are presented as means±sem, medians (range) or mean difference/median-ratio [95% confidence interval (CI)]. P-values<0.05 were considered significant. For measurements with three or more data points, iAUC (incremental area under the curve) was used.

Results
Ten participants were randomized in the study. One participant was excluded due to technical reasons, leaving a total of 9 participants included in the study and analysis. The study was conducted between December 2017 and October 2018 with a median of 54 days (range 40 to 85 days) between each visit. The baseline characteristics of the nine men participating in the study are depicted in table 4.

TABLE 4

Baseline characteristics.
Baseline characteristics

| | | Median (min max) |
|---|---|---|
| Age | years | 25 (22 29) |
| Height | cm | 182 (170 188) |
| Weight | kg | 81 (69.2 87) |
| BMI | kg/m² | 24.3 (20.7 28.0) |

Interventions:
Participants consumed an average of 48.5±0.60 grams of protein mixed with tap-water (~11% protein solution) at each visit, with no difference in grams of protein consumed between BLG, CAS and WHE (p=0.89). The intervention dose was 0.6 g protein/kg bodyweight. The composition of the three different proteins is shown in table 3.

Figure 2:
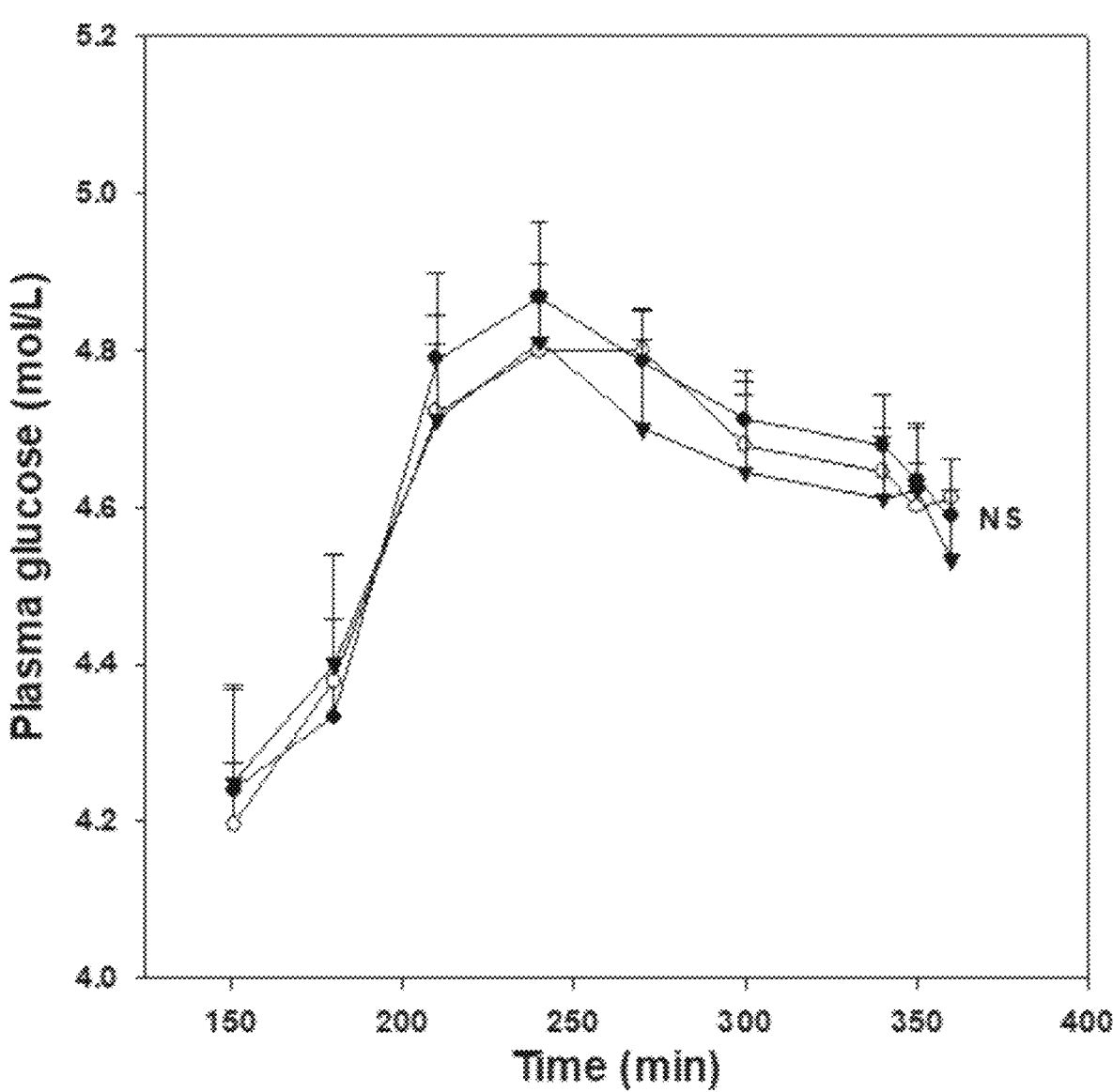
FIG. 2 illustrates the mean blood glucose concentrations after interventions with BLG (black dot), CAS (white dot) and WHE (black triangle) with SEM (error bars). NS=No significant difference between interventions. Repeated measures mixed modeling on incremental area under the curve (iAUC) was used to compare interventions.
Figure 3:
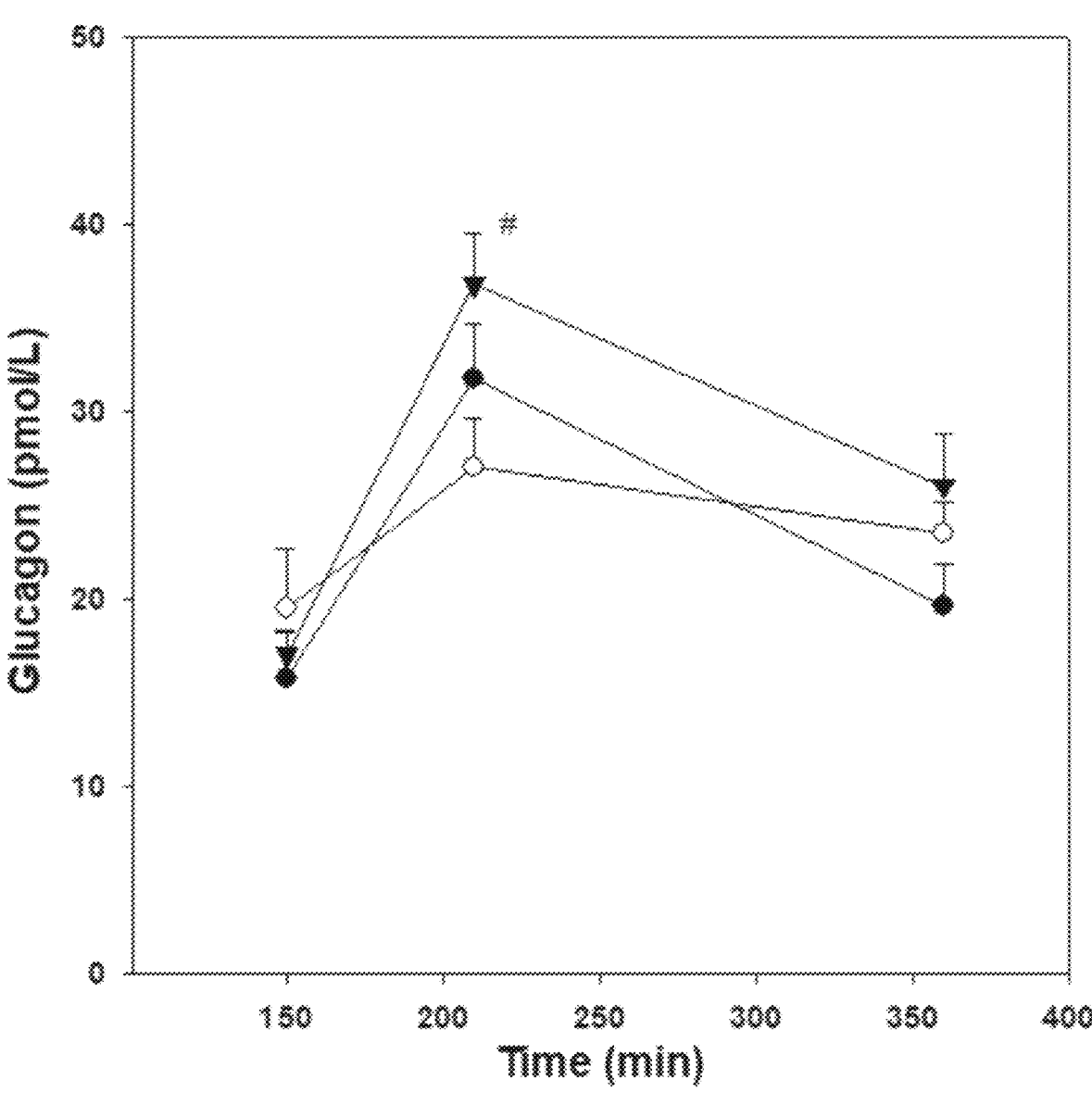
FIG. 3 illustrates the mean plasma concentrations of glucagon after interventions with BLG (black dot), CAS (white dot) and WHE (black triangle) with SEM (error bars). #=significantly different from casein. Repeated measures mixed modeling on iAUC was used to compare interventions.
Figure 4:
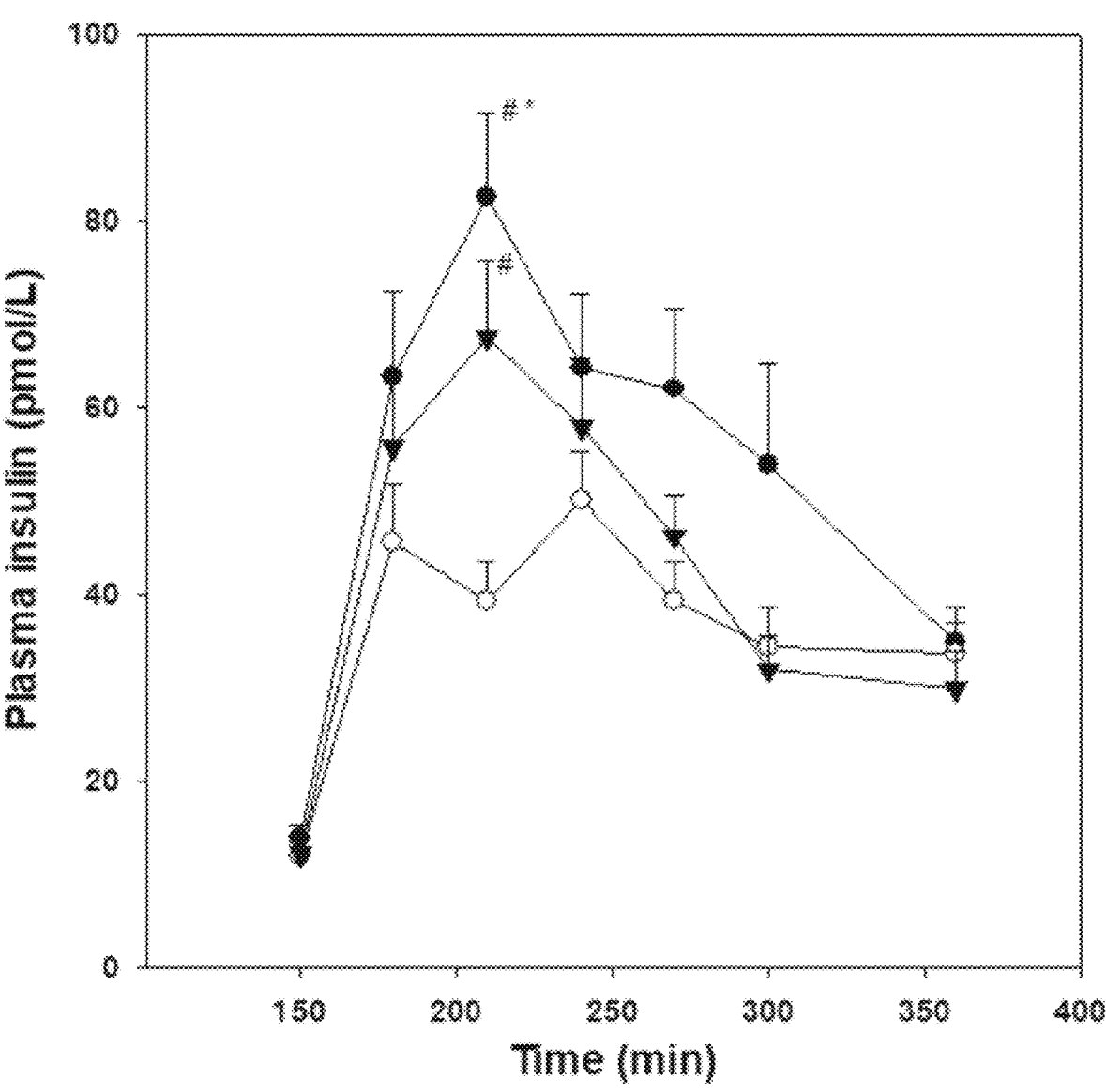
FIG. 4 illustrates the mean serum insulin concentrations after interventions with BLG (black dot), CAS (white dot) and WHE (black triangle) with SEM (error bars). #=significantly different from casein, *=significantly different from WHE. Repeated measures mixed modeling on iAUC was used to compare interventions.
Figure 5:
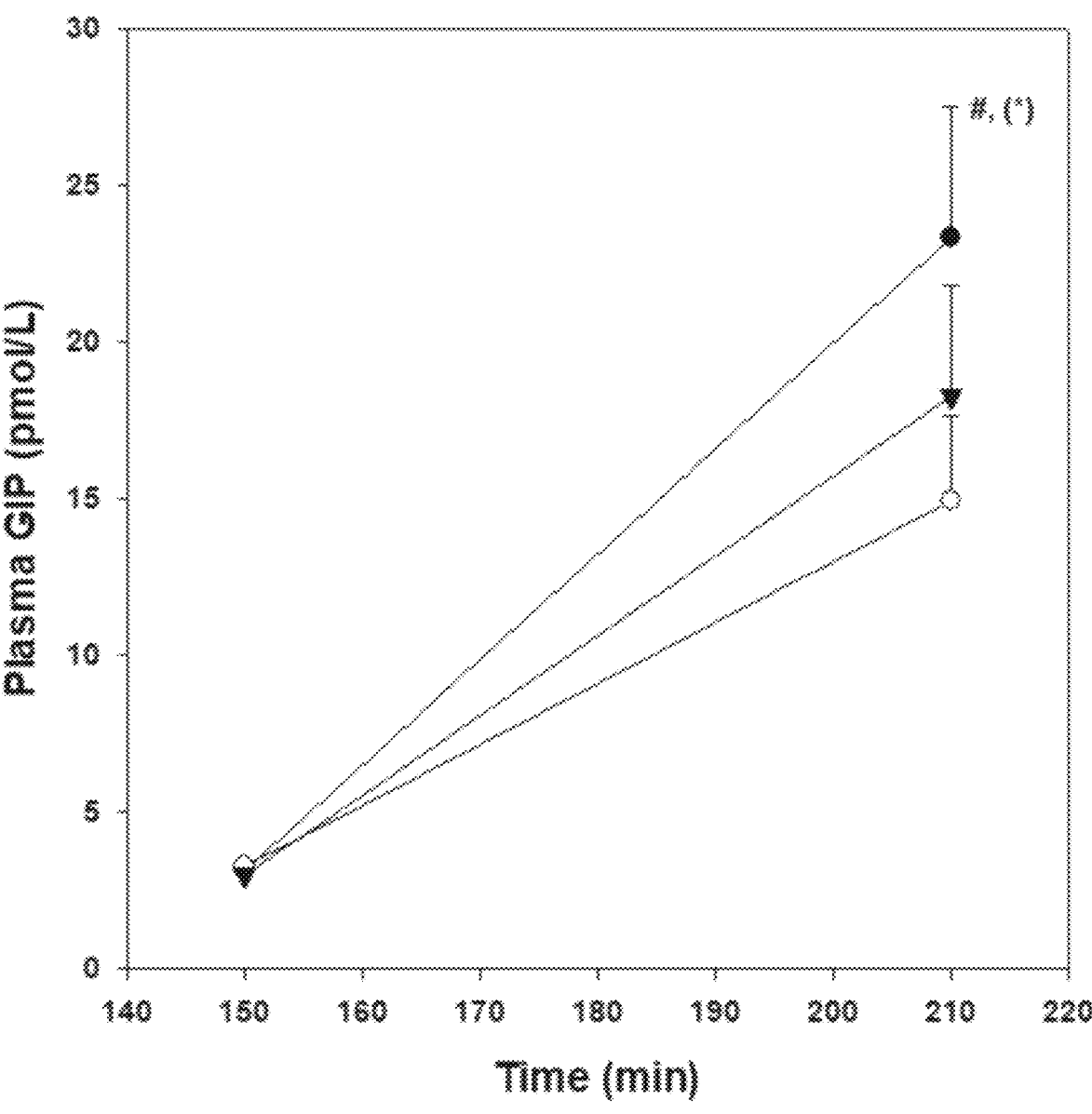
FIG. 5 illustrates the mean plasma GIP concentrations after interventions with BLG (black dot), CAS (white dot) and WHE (black triangle) with SEM (error bars). #=significantly different from casein (p=0.001), (*)=different from whey (p=0.057). Repeated measures mixed modeling on delta GIP (t=210 minus t=150) was used to compare interventions.
Figure 6:
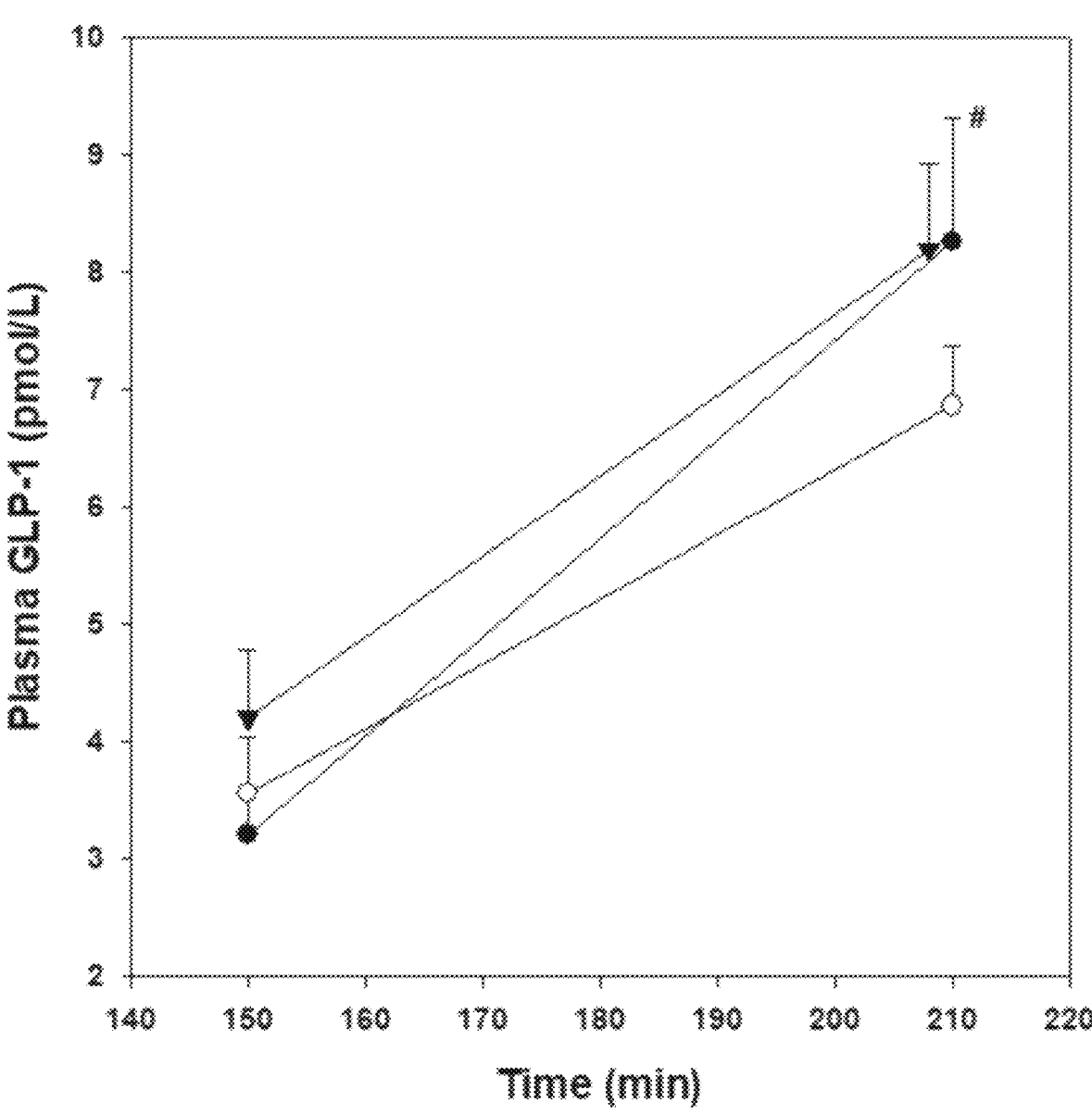
FIG. 6 illustrates the mean plasma GLP-1 concentrations after interventions with BLG (black dot), CAS (white dot) and WHE (black triangle) with SEM (error bars). #=significantly different from casein (p<0.05). Repeated measures mixed modeling on delta GLP-1 (t=210 minus t=150) was used to compare interventions.
Figure 7:
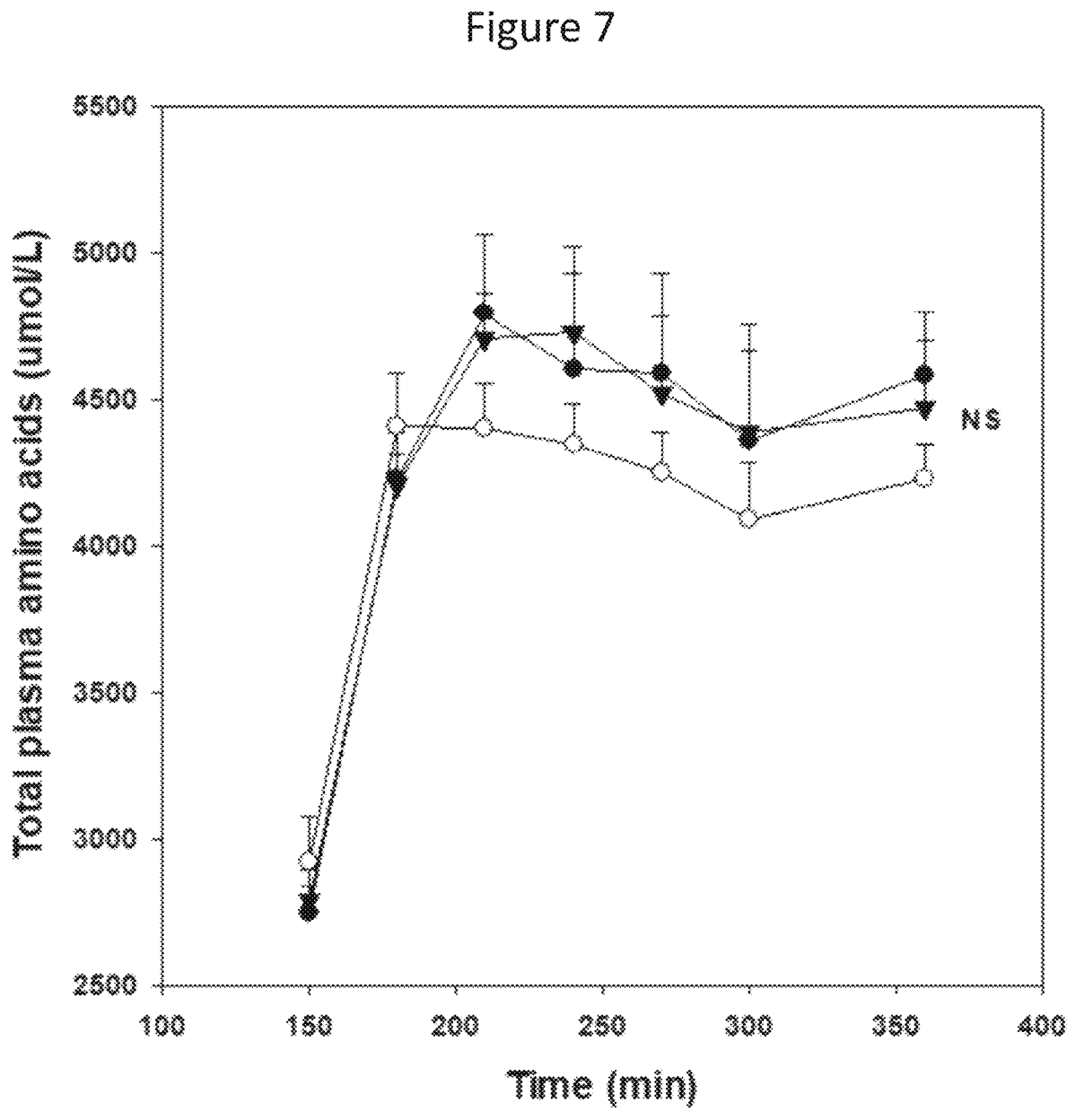
Figure 8:
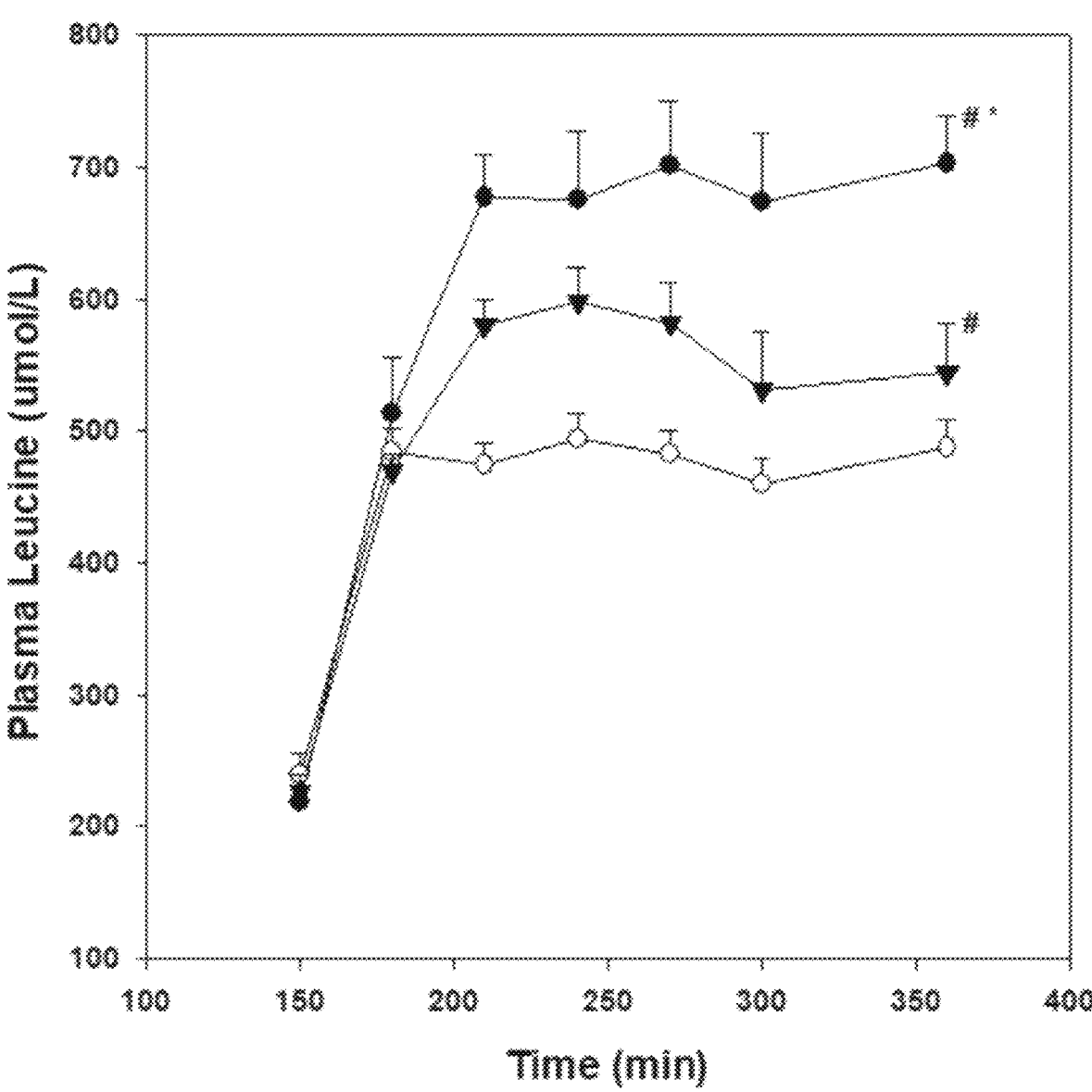
FIG. 8 illustrates plasma leucine concentrations after interventions with BLG (black dot), CAS (white dot) and WHE (black triangle) with SEM (error bars). #=significantly different from casein. *=significantly different from whey. Repeated measures mixed modeling on iAUC was used to compare interventions.

The results are presented in FIG. 2 (glucose), FIG. 3 (plasma glucagon), FIG. 4 (serum insulin), FIG. 5 (plasma GIP), FIG. 6 (plasma GLP-1), FIG. 7 (plasma amino acids concentrations) and FIG. 8 (plasma leucine concentrations).
Glucose Concentrations:

Interventions with BLG, CAS or WHE did not result in differences in iAUC of plasma glucose (p=0.5) as illustrated in FIG. 2.

The participants had been fasting for 36 hours before the intervention with proteins (BLG, CAS or WHE), and their blood glucose was therefore low before the intervention was initiated. Furthermore, the intervention consisted of solely protein with almost no carbohydrates. We therefore did not see an additional lowering of the blood glucose due to the intake of BLG compared to WHE or CAS in this population, since a healthy body, without diabetes, always strives to maintain a normal blood glucose level, and lowering the blood glucose would be "un-physiological".
Plasma Glucagon Concentrations:

It was found that plasma glucagon iAUC was significantly higher in WHE compared with CAS (p=0.015), whereas no difference was observed between WHE and BLG or BLG and CAS see FIG. 3.
Insulin Concentrations:

BLG increased iAUC of serum insulin compared with CAS (median-ratio [95% CI]; 1.62 [1.37 1.87], p<0.0001) and WHE (median-ratio[95% CI]; 1.30 [1.10 1.51], p=0.002), and WHE increased insulin iAUC more than CAS (median-ratio[95% CI]; 1.25 [1.06 1.48], p=0.006) (FIG. 4).

Although the insulinotropic effects of BLG did not change blood glucose in healthy participants undergoing inflammatory disease conditions, we expect that the insulinotropic effect might prove beneficial in a population suffering from diabetes, since medicamental manipulation with the body's GIP, GLP-1 and insulin levels (e.g.; exogenous insulin, DDP4-inhibitors and GLP-1 agonists) in diabetic subjects have already proven effective in lowering blood glucose levels.
Gastric Inhibitory Polypeptide (GIP) Concentrations:

GIP measurements are shown in FIG. 5. At the time of insulin peak (t=210), deltaGIP (delta=GIP(210 min) minus GIP(150 min)) levels were higher after BLG compared with CAS and WHE (median-ratio [95% CI]; 1.7 [1.25 2.3], p=0.001 and 1.34 [0.99 1.82], p=0.057) whereas no difference between WHE and CAS was observed (1.27 [0.94 1.72], p=0.12).
Glucagon-Like Peptide-1 (GLP-1) Concentrations:

GLP-1 measurements are shown in FIG. 6. DeltaGLP-1 (Delta=GLP-1(210 min) minusGLP-1(150 min)) was higher in BLG compared with CAS (mean±sem: 5.07±0.94 μmol/L vs 3.31±0.56 μmol/L, p=0.028), whereas no difference was shown between BLG and WHE (p=0.16) and WHE and CAS (p=0.35).

Plasma GIP (which is mainly secreted from enteroendocrine K-cells in the proximal small intestine) increased more after ingestion of BLG compared with CAS and WHE. This could be part of a mechanistic explanation for the higher insulin secretion. Both GIP and GLP-1 stimulate insulin secretion from beta cells (incretin effect).

Likewise, plasma GLP-1 (which is mainly secreted from enteroendocrine L-cells at more distal sites of the small intestine) also increased more after intake of BLG compared with CAS, but no difference was shown between BLG and WHE.

It should be noted that the baseline level of GLP-1 appeared more scattered between trials (BLG, WHE and CAS) than that of GIP.

It could be speculated, that the difference in insulin secretion between BLG and WHE is therefore more dependent on GIP secretion, potentially elicited in proximal parts of the ileum where specific BLG peptides may induce GIP secretion. CAS induces a smaller secretion of both GIP and GLP-1 compared to BLG.
Amino Acids Concentrations:

Total amino acid concentration in plasma (iAUC) was not different between groups (p=0.12) (FIG. 7). Plasma leucine concentration was significantly higher after BLG compared with CAS and WHE (median-ratio[95% CI]; 1.82 [1.50 2.22], p<0.0001 and 1.37 [1.13 1.67], p=0.002, respectively) and after WHE compared with CAS (median-ratio[95% CI]; 1.33 [1.10 1.62], p=0.005) (FIG. 8).
Conclusions:

We surprisingly found that intake of BLG beverages raises blood concentration of insulin with 62% more compared with isocaloric and isonitrogenous casein and 30% more than isocaloric and isonitrogenous whey in healthy, lean young study participants following LPS-exposure, bedrest, and fasting. Without being bound by theory the insulinotrophic effect of BLG might be mediated through increased levels of GIP from the gastrointestinal tract.

Previous studies have found that serving a protein premeal may effectively damper glucose fluctuations following a meal or an oral glucose tolerance test (OGTT). These effects have primarily been attributed to GIP and GLP-1 release and subsequent insulin release. We therefore believe that BLG compared to whey proteins or casein may be especially potent and serve as a strategy to alleviate, treat, or hinder diabetes and high circulating concentrations of glucose.

Example 5

Investigation of the Insulinotropic Effects of Beta-Lactoglobulin and Whey in Participants with T2DM Methods
Participants:

Inclusion criteria were: Type 2 Diabetes Mellitus (T2DM), age between 18 and 80 years old, BMI between 20 and 35 kg/m², hemoglobin(Hb)-A1c between 40 and 69 mmol/L, and c-peptide between 370 and 1200 μmol/L. participants were recruited through social media (Facebook) and local newspapers. Exclusion criteria were: milk allergies, daily intake of protein supplements, anti-glycemic medication other than metformin or inability to speak or understand Danish. Participants were screened with blood test on HbA1c, kidney and liver parameters, thyrotropin, c-reactive-protein, hemoglobin and c-peptide before inclusion. Participants ate according to Danish nutritional guidelines (15% fat, 30% protein and 55% carbohydrates) for 48 hours prior to the study days and avoided vigorous physical activity. Metformin was paused for five days prior to and during the study. They had fasted from 10.00 PM before attending the laboratory next morning.
Design:

The design was a randomized, double-blinded, crossover trial with two intervention arms. Study days included the interventions and an oral glucose tolerance test (OGTT) performed in our laboratory and four days of monitoring at home. The two interventions consisted of: i) 25 g BLG and ii) 25 g whey protein isolate (WPI). The washout period between the laboratory study days was between one week and a maximum of six weeks. Investigators and participants were blinded to the interventions.

For the BLG sample an acidic BLG powder was used, it comprises 98.2% BLG of total protein. It is produced as outlined in example 2 of WO2020/002426. For the comparison whey protein isolate (Lacprodan® DI-9213, Arla food ingredient) replace the 98.2% BLG product in the making of a reference sample.

At the laboratory, the participants consumed either 25 g of WPI or BLG protein 30 minutes before consuming a 75 g OGTT (75 g of glucose dissolved in 200 mL of water). The test is performed to assess a participant's ability to clear glucose from the circulation. The result depends on the individual's insulin secretion and insulin sensitivity. Blood was sampled through an intravenous catheter placed in an antecubital vein and collected at arrival and consecutively the three following hours of the OGTT. Blood samples were drawn at −30, 0, 10, 20, 30, 40, 50, 60, 90, 120, 150 and 180 minutes following the OGTT.

Figure 9:
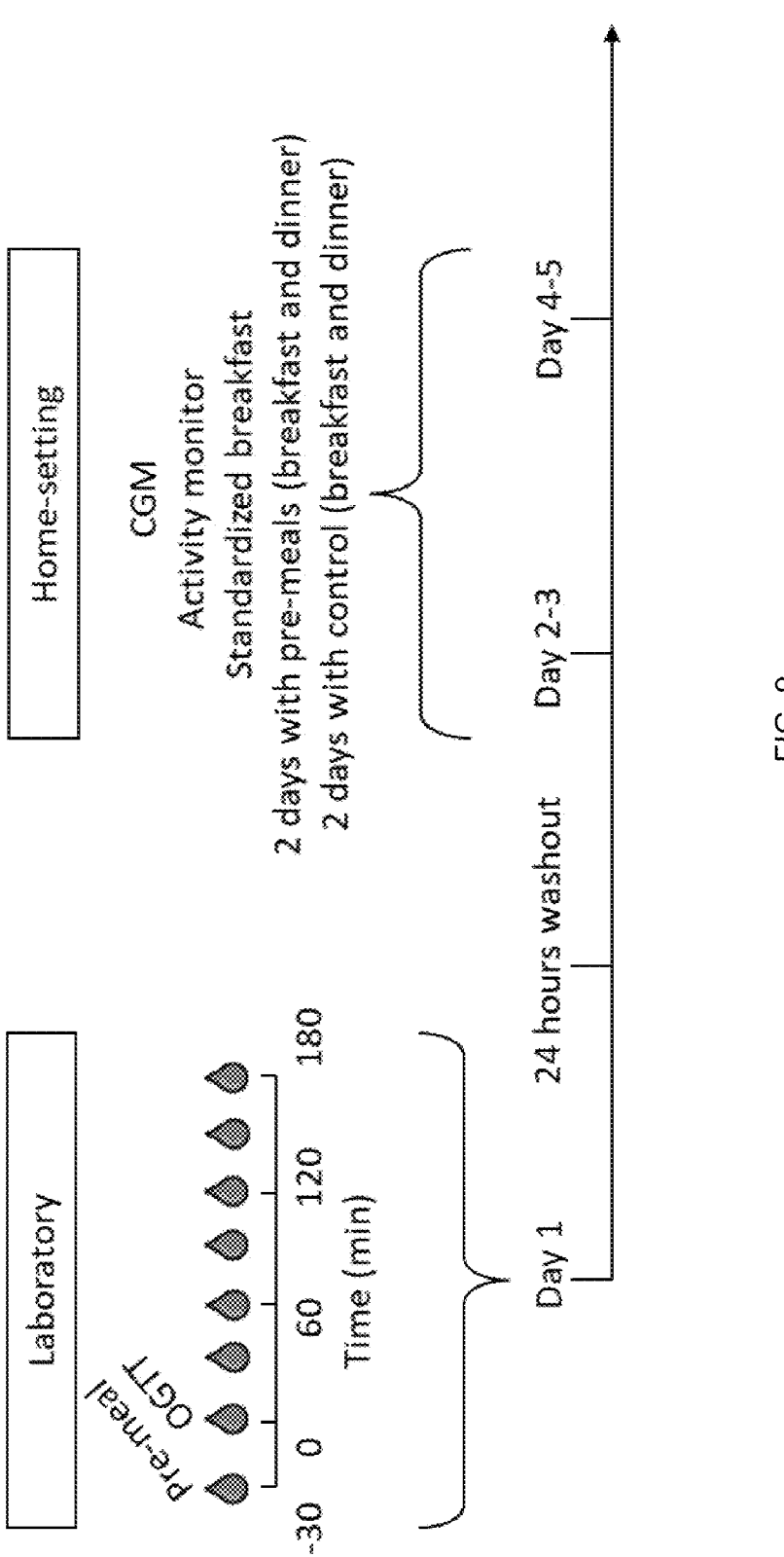
FIG. 9: Flowchart of the study. The subjects were randomized to ingest one of two pre-meals i) β-lactoglobulin (BLG) or ii) whey protein isolate (WPI) 30 minutes prior to a 75 g oral glucose tolerance test (OGTT) in the laboratory or prior to breakfast and dinner at home. The subjects wore a continuous glucose monitor (CGM), an activity monitor, and were provided with standardized breakfast meals. The subjects were also randomized to ingest pre-meals before breakfast and dinner day 2-3 or day 4-5 and control (tap-water) the other two days. The study days were repeated after 1-6 weeks from the OGTT.

Following the laboratory study day, participants were equipped with a continuous glucose monitor (CGM) and an activity monitor. They received four standardized breakfasts (50 g cornflakes (Vores Cornflakes 500 g), 31 g raisins (Svansoe Rosiner 1500 g) and 250 mL skimmed milk (Aria® Skummetmaelk 0.1% 250 mL) equivalent to 77.6 g carbohydrates, 13.9 g protein, 1 g fat/1,593 kJ/375 kCal) and four plastic bags with 25 gram of the protein intervention. Each participant consumed the protein pre-meals 30 minutes before the breakfast and dinner for two days (day 2-3) and the control (iso-voluminous amount of tap-water) 30 minutes prior to breakfast and dinner for two days (day 4-5). The sequence of day 2-3 and 4-5 was randomized (FIG. 9). They avoided vigorous physical activity and ate likewise during the home experiment. The participants kept a food-diary with timestamps for pre-meals and meals for the CGM analyses.

For study plan, see FIG. 9.

Interventions:

Preparation before serving: 1) Add 200 ml water to a suitable container (preferably a shaker with a spiral wire), 2) Add protein powder to water (26.7 g BLG and 28.3 g WPI) to produce a sample comprising 25 g protein, 3) Shake until homogenous (about 15-30 seconds). The composition of amino acids of BLG and WPI is shown in table 5.

TABLE 5

Amino acid composition of the BLG and WPI powders/products.

| /100 g product | BLG | WPI |
| --- | --- | --- |
| Total energy, kCal | 375 | 355 |
| Fat, g | 0.1 | 0.1 |
| Carbohydrate, g | 0.1 | 0.1 |
| Protein, g | 93.5 | 88.3 |
| Alanine, g | 6.58 | 5.32 |
| Arginine, g | 2.63 | 2.03 |
| Aspartic acid, g | 11.30 | 10.40 |
| Cysteine, g | 2.89 | 2.30 |
| Glutamic acid, g | 18.80 | 17.40 |
| Glycine, g | 1.28 | 1.40 |
| Histidine, g | 1.55 | 1.46 |
| Hydroxyproline, g | <0.05 | <0.05 |
| Isoleucine, g | 5.91 | 6.21 |
| Leucine, g | 15.00 | 10.30 |
| Lysine, g | 11.50 | 9.39 |
| Methionine, g | 2.62 | 2.14 |
| Ornithine, g | <0.05 | <0.05 |
| Phenylalanine, g | 3.32 | 2.70 |
| Poline, g | 5.05 | 6.02 |
| Serine, g | 3.67 | 4.65 |

TABLE 5-continued

Amino acid composition of the BLG and WPI powders/products.

| /100 g product | BLG | WPI |
| --- | --- | --- |
| Threonine, g | 4.99 | 7.07 |
| Tryptophan, g | 2.06 | 1.66 |
| Tyrosine, g | 3.41 | 2.58 |
| Valine, g | 5.68 | 5.68 |
| Sum, g | 108.24 | 98.71 |

Randomization:

Participants were randomized using a computerized randomization system by the primary investigator.

Blood Sample Analysis

Blood samples were stored at minus 80 degrees Celsius and then analyzed on the same assay after study completion to minimize analytic variation.

Methods for analyzing: plasma glucose: example 1.13, serum insulin: example 1.14, plasma glucagon: enzyme-linked immunosorbent assay (ELISA) technique using a commercial kit (Mercodia Glucagon ELISA, Sweden), plasma GIP and GLP-1: example 1.16, plasma amino acids: high pressure liquid chromatography (HPLC). A Thermo Scientific Ultimate 3000 system was used. First samples were diluted 1.11× with 2 M Perchloric acid ($HClO_4$). Then they were centrifuged at 14,000 G at 4° C. for 10 minutes. The supernatant was then removed and a spin filter (0.22 μm) was used for filtration at 14,000 G for 1 min. Then the samples were diluted 50× by adding 0.2 M $HClO_4$. The samples reached a final dilution factor of 55.5. Then samples were injected into the HPLC. A Kinetex EVO C18 2.6 μm 4.6×150 mm column (Phenomenex) was used for separation. Fluorometric detection was done with an excitation on 337 nm and emission on 442 nm.

Continuous Glucose Monitoring (CGM)

A CGM device form Nordiclnfu Care Denmark, Dexcom G6, Dexcom Inc., San Diego, CA, USA was used for collection of glucose concentrations in the interstitial fluid (ISF). A subcutaneous sensor is inserted into the skin on the abdomen. The device was blinded so that participants were unaware of their glucose level. The software CLARITY (Dexcom Inc., San Diego, CA, USA) was used for obtaining: mean glucose±standard deviation (SD), daily maximum glucose level and the coefficient of variation (CV %).

Activity Monitor

A device (Actiheart) which is a combined accelerometer and heart rate (HR) monitor (Actiheart, AH) was used to collect measurements on activity and energy expenditure during the home investigation period. The device is worn on the chest. The AH software (Actiheart software, version 5.1.10, camNtech ltd., Cambridge, UK) was used to obtain: total energy expenditure, activity energy expenditure, heart rate (HR), maximum HR, and activity counts.

Statistics:

For figures and statistical analyses the nlme (version 3.1-142), Epi (version 2.37) in R (R Foundation for Statistical Computing, Vienna, Austria, version 3.6.2) and Sigma-Plot (San Jose, California, USA, version 14.0) was used. If data were not normally distributed data were log transformed (natural logarithm). Data are presented as means with 95% confidence intervals or medians with ranges. Curves were fitted using random effects models with a natural cubic spline specification for time. Interaction terms were included for each time term and a binary variable that coded for the two pre-meals. This was combined with appropriate contrast matrices to estimate curves for both pre-meals and their difference at any time point during the study. As the outcomes were log-transformed (natural logarithm) before running the models due to their skewed distribution, the difference between curves is given in percentages. We included individual specific random intercepts and slopes in the models to account for the dependence within the data due to its repeated measurement nature. For the analysis on glucose following breakfast, measurements were included for analysis if their time points were after the recorded time of breakfast and dinner, but within three hours of the recorded time of the meals. The incremental area under the curve (iAUC) was calculated using the trapezoidal approach and a paired t-test was used for comparing each outcome during the laboratory day, and One way repeated measures ANOVA was used to compare iAUC of glucose home measurements. A random effects model was used to compare CGM-based summary variables between interventions and controls. P-values<0.05 and 95% confidence intervals not containing zero were considered statistical significant.

Results

Sixteen participants attended both laboratory study days. The study days were performed between January 2020 and June 2020. One participant failed to complete the home part of the study and so these analyses are based on n=15. Patient characteristics are shown in (Table 6). The washout-period was a median of 8.5 days (range 7-23 days).

TABLE 6

Baseline characteristics.

| Characteristics | n = 16 |
|---|---|
| Age, years | 67.5 (40-78) |
| BMI, kg/m² | 26.95 (21.2-32.9) |
| Women, % | 56.2 |
| Metformin treatment, n | 14 |
| HbA1c, mmol/mol | 49.5 (43-55) |
| Fasting c-peptide, nmol/L | 931.5 (499-1155) |
| Fasting insulin, pmol/L | 40 (20-94) |

Data are presented as absolute numbers or medians (ranges)

OGTT

Figure 10:
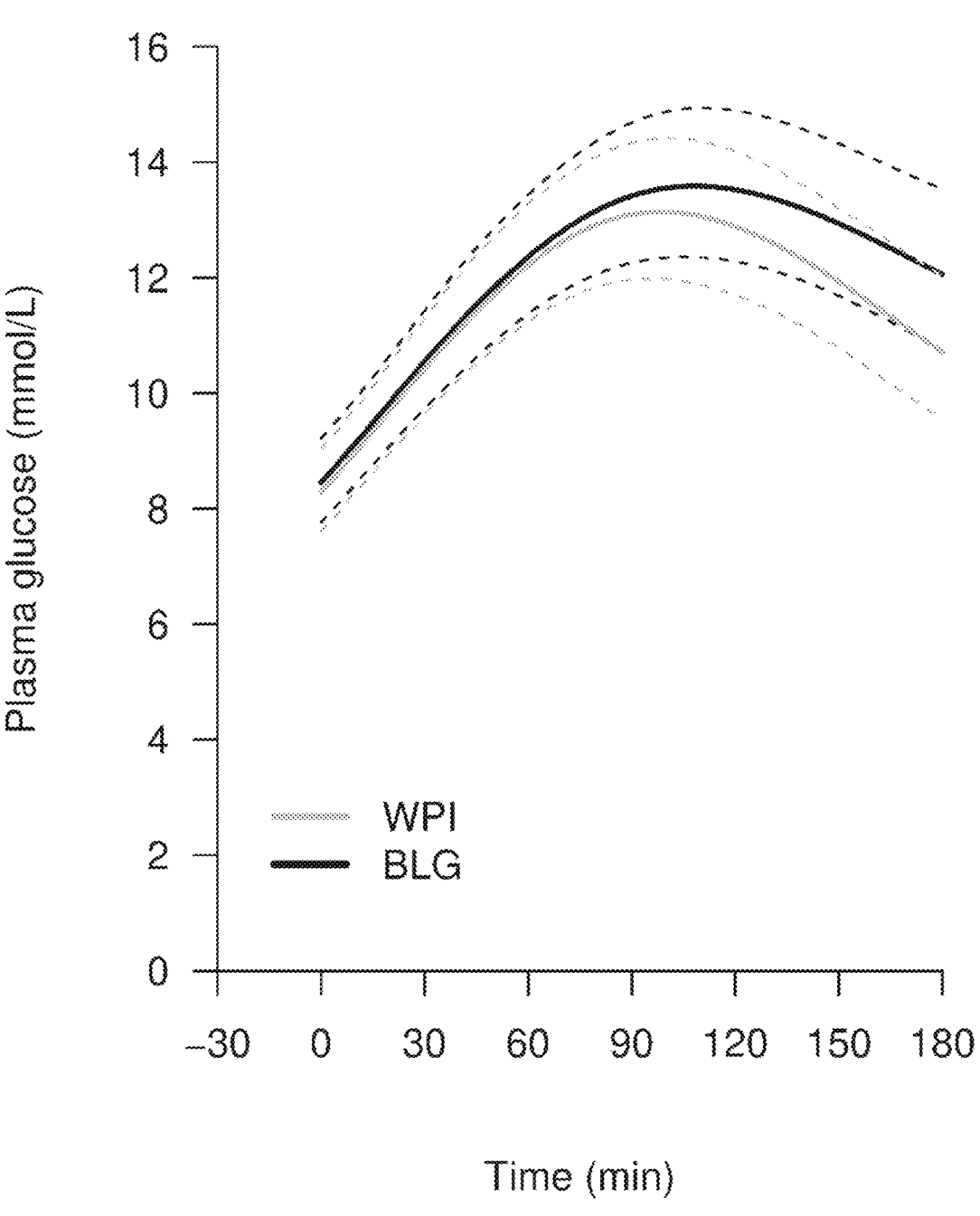
FIG. 10a+b illustrates mean plasma glucose curves by intervention (black: BLG, grey: WPI) and their difference as percentage, both with 95% CIs based on a mixed effect model.
FIG. 10c illustrates the individual incremental area under the curve (iAUC) with a bar plot that shows the mean±standard deviation.
Figure 10:
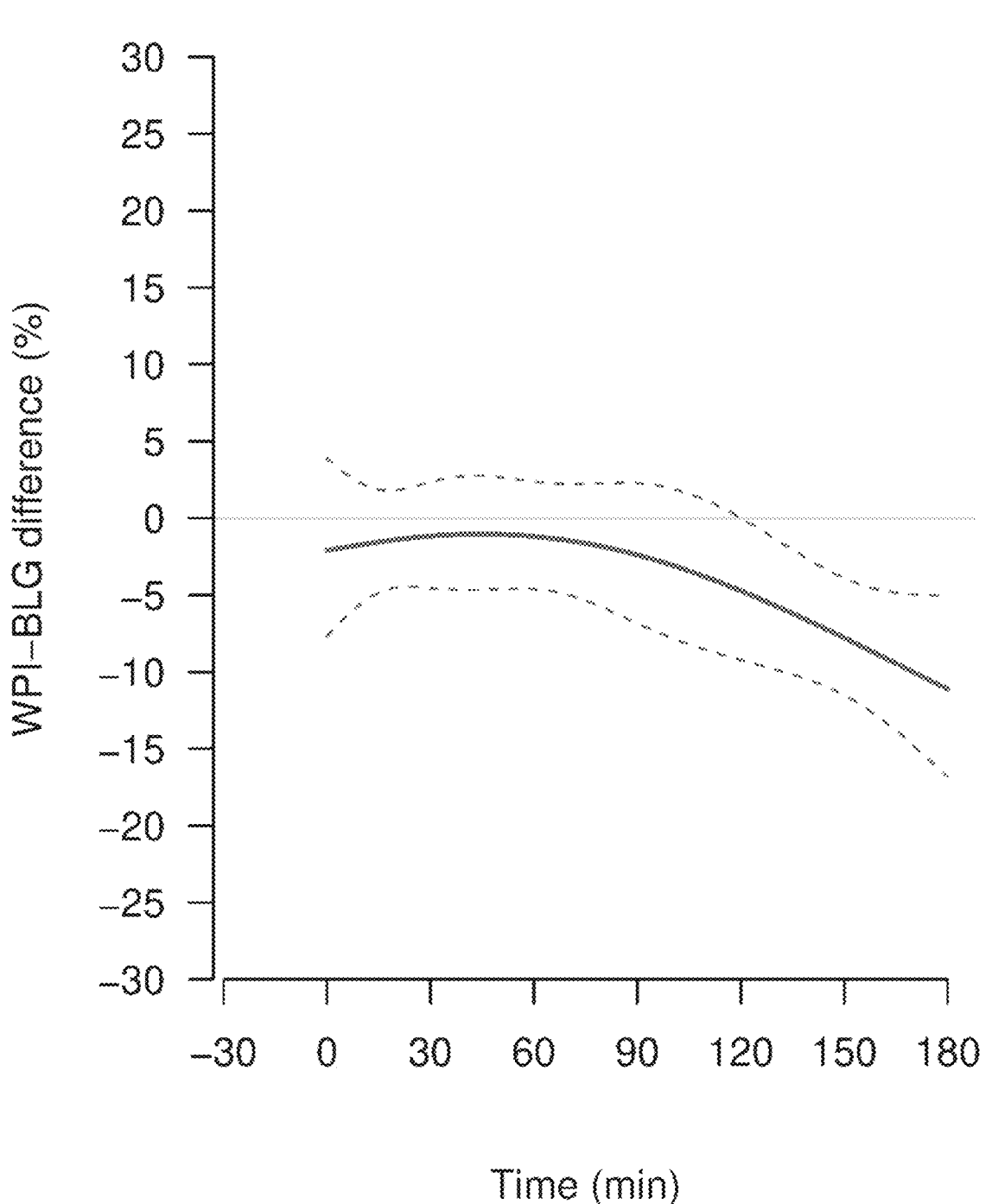
Figure 10:
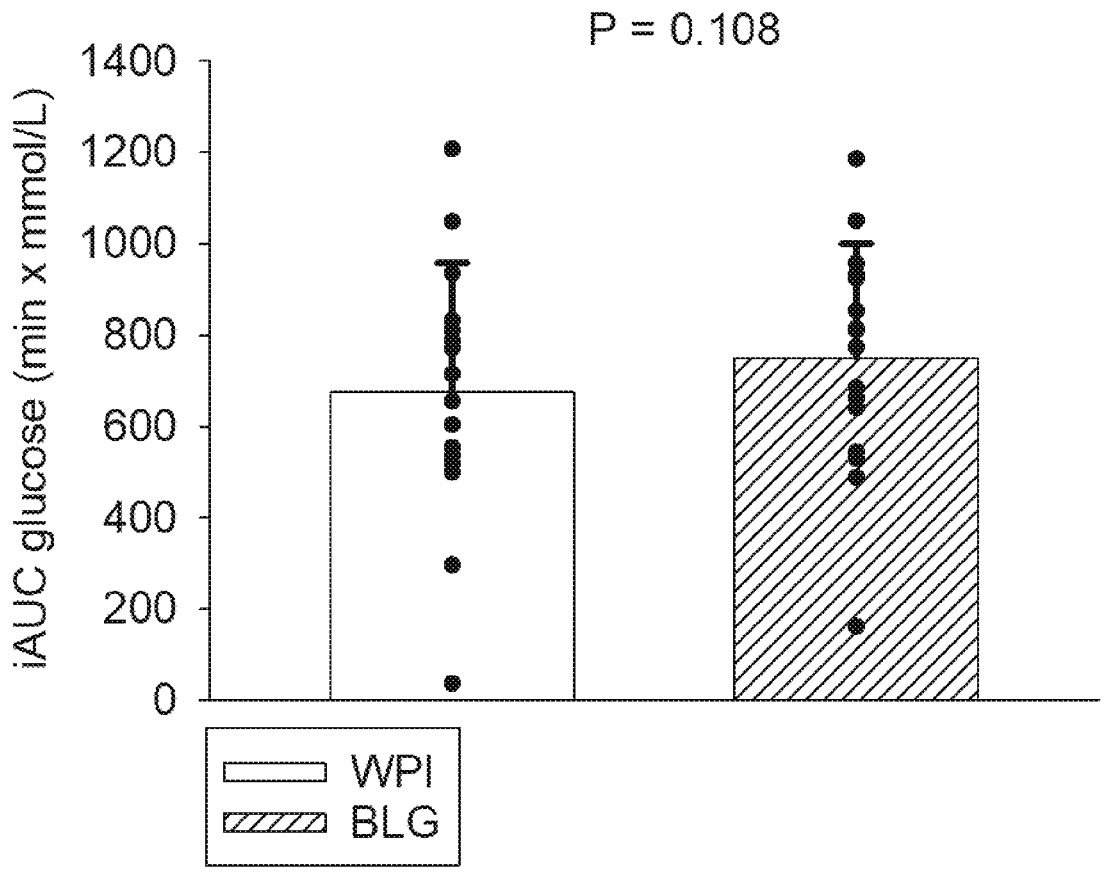

The concentration of plasma glucose was higher after ~120 minutes after BLG consumption compared with WPI with a maximum difference of ~10% 180 minutes following the OGTT (FIG. 10). The concentration of serum insulin was

Figure 11:
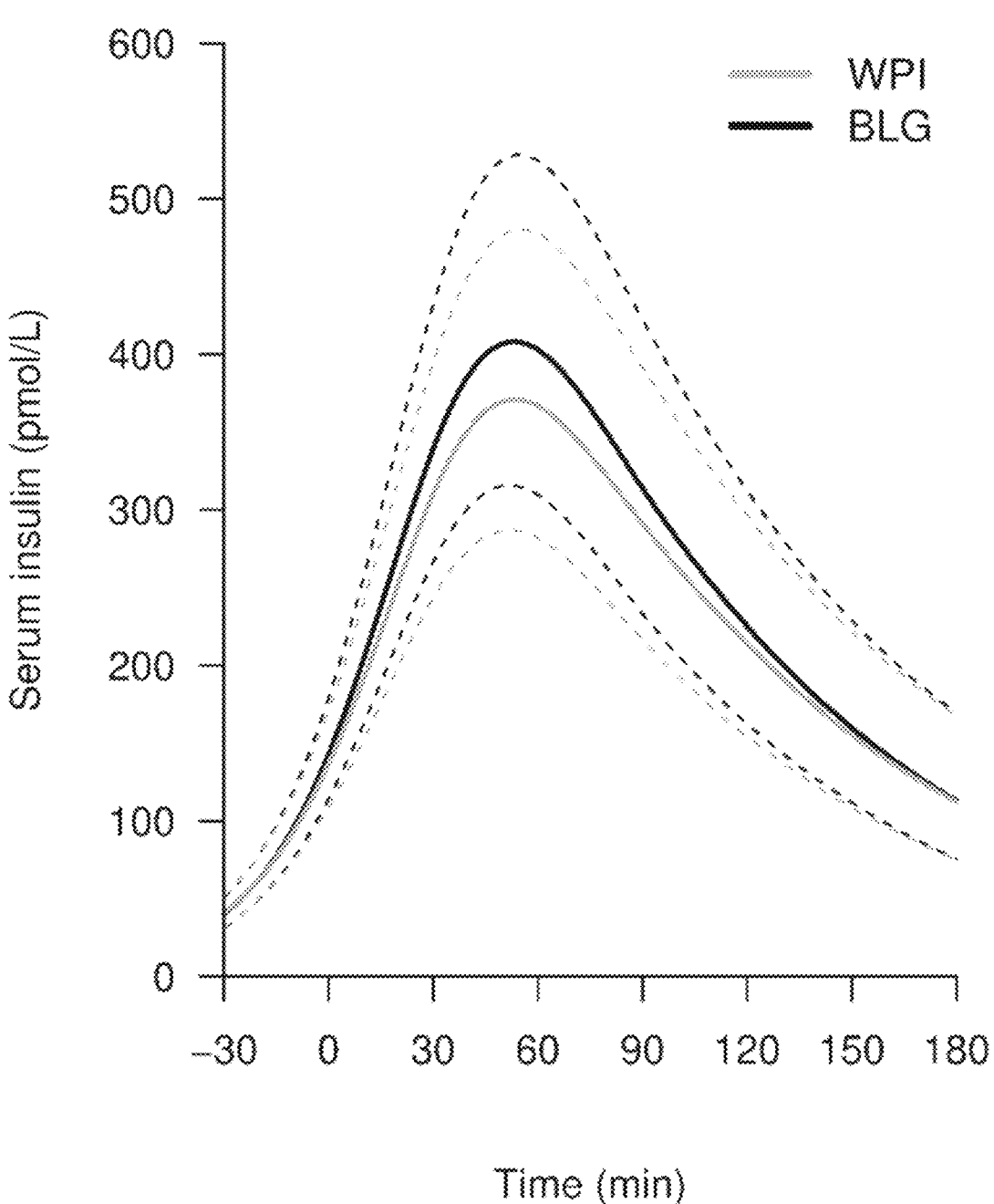
FIG. 11a+b illustrates the mean serum insulin curves by intervention (black: BLG, grey: WPI) and their difference as percentage, both with 95% CIs based on a mixed effect model.
FIG. 11c illustrates the individual incremental area under the curve (iAUC) with a bar plot that shows the mean±standard deviation.
Figure 11:
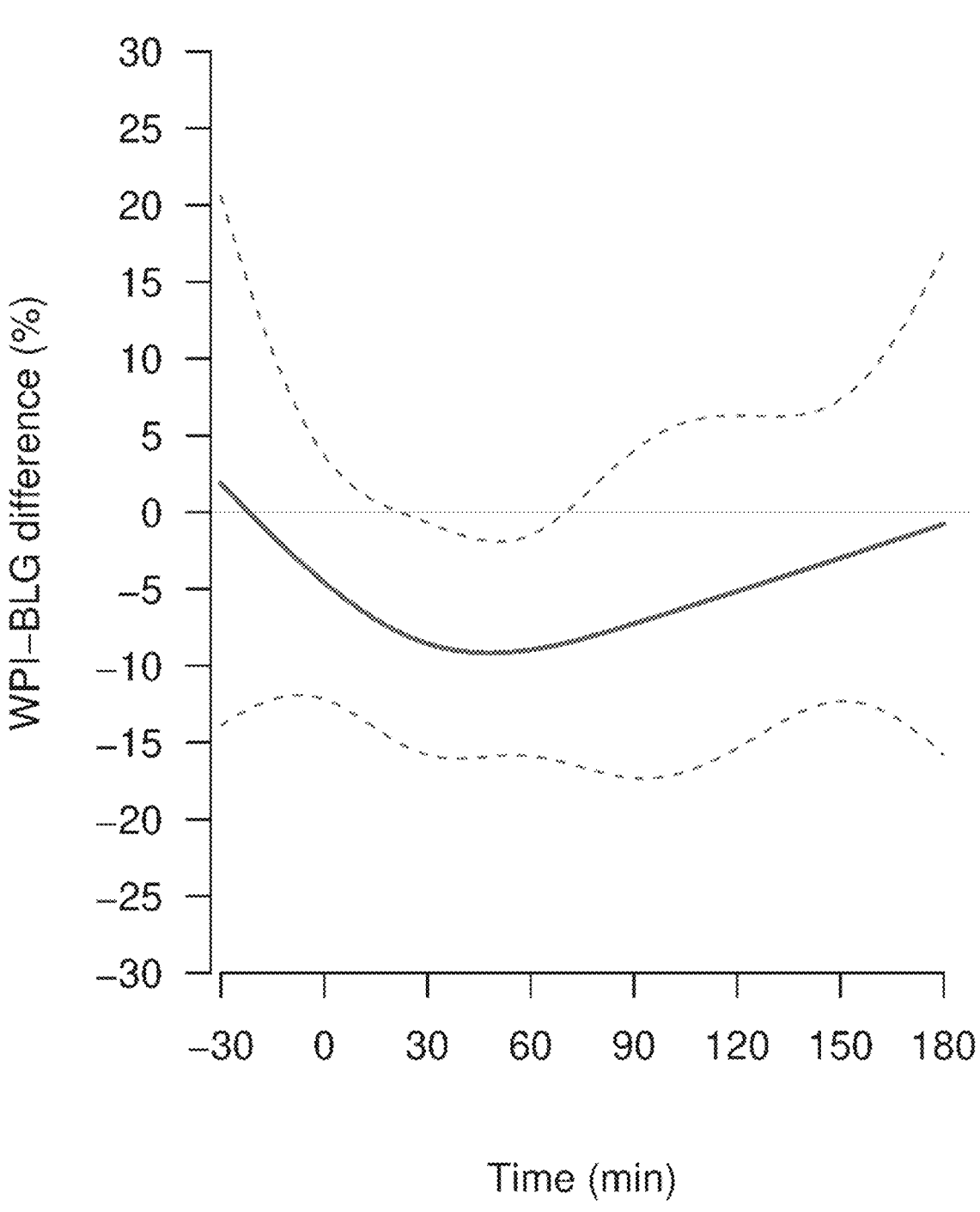
Figure 11:
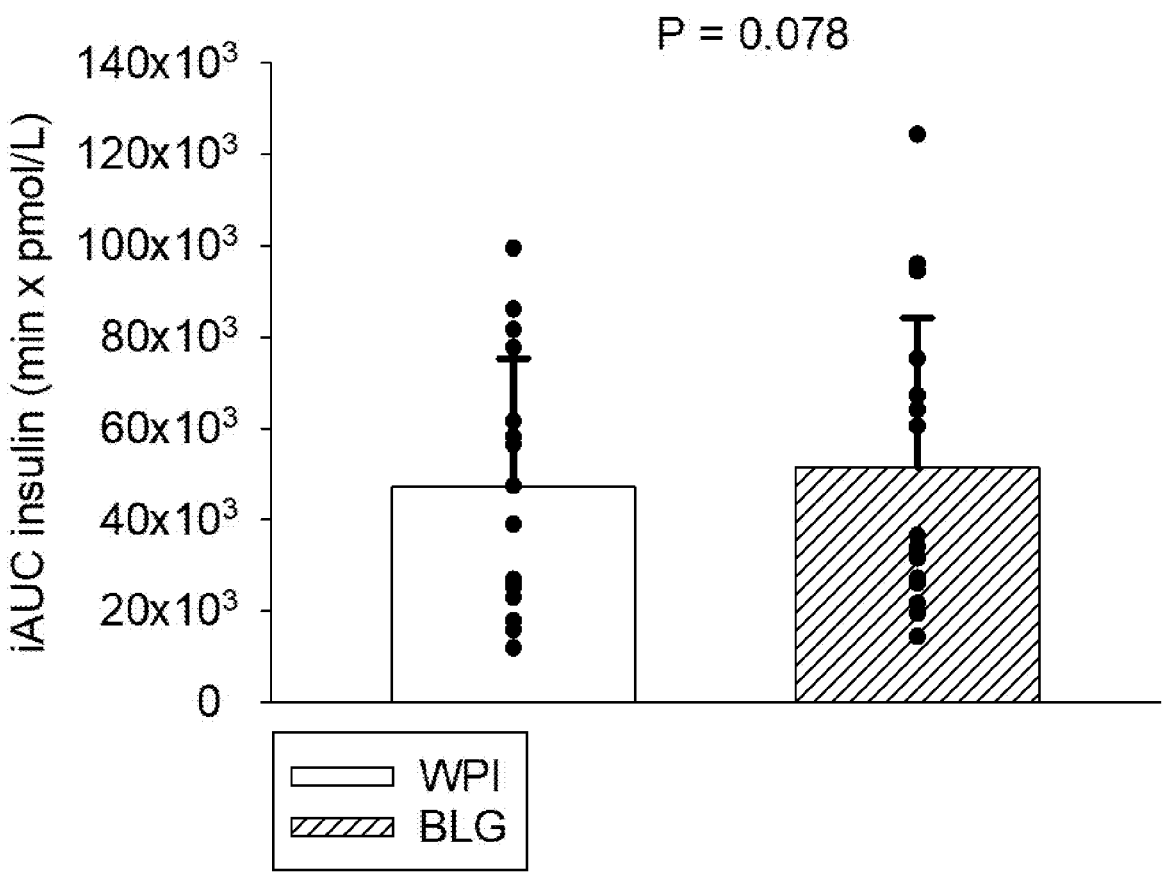
Figure 12:
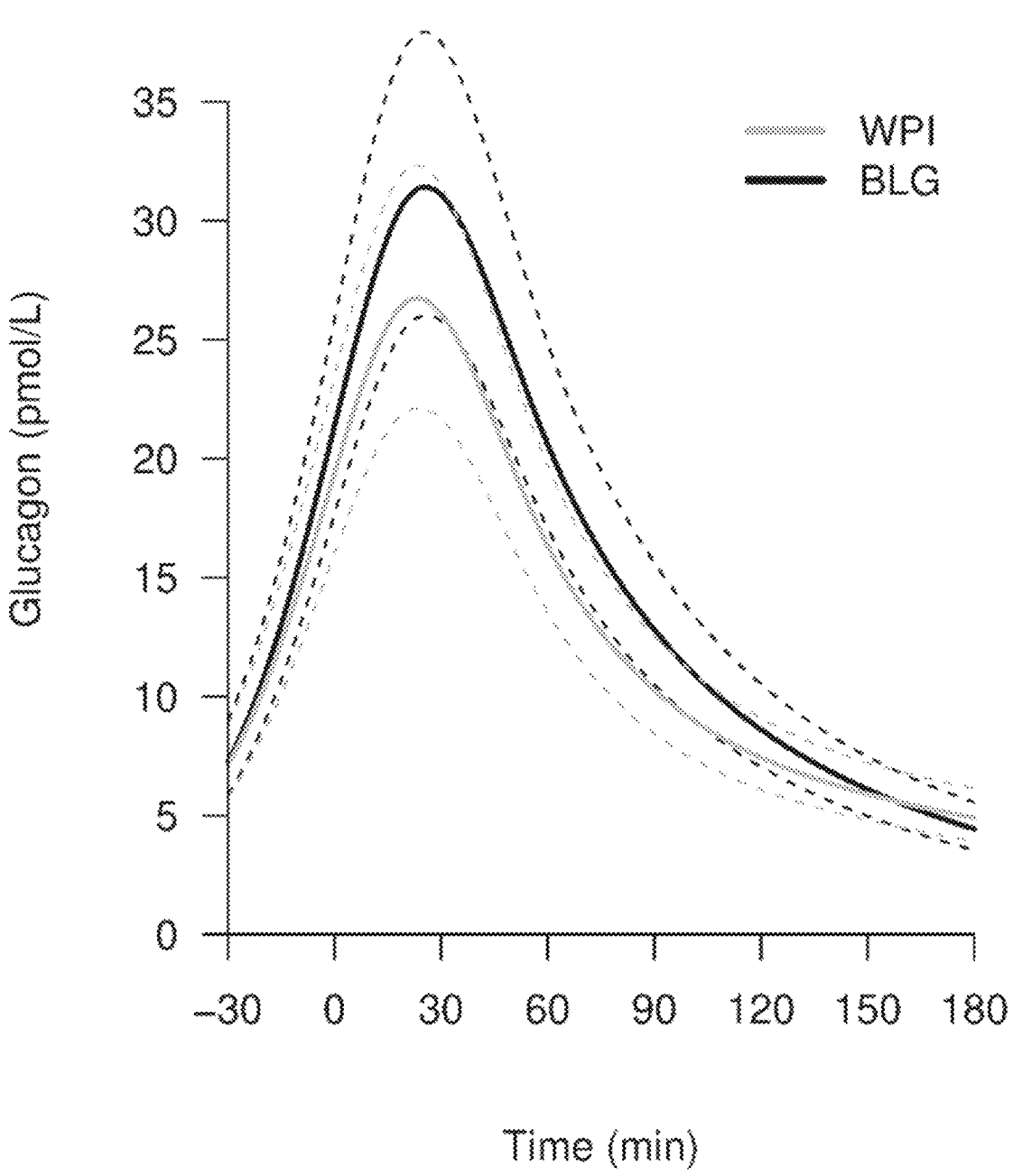
FIG. 12a+b illustrates the mean serum glucagon curves by intervention (black: BLG, grey: WPI) and their difference as percentage, both with 95% CIs based on a mixed effect model.
FIG. 12c illustrates the individual incremental area under the curve (iAUC) with a bar plot that shows the mean±standard deviation.
Figure 12:
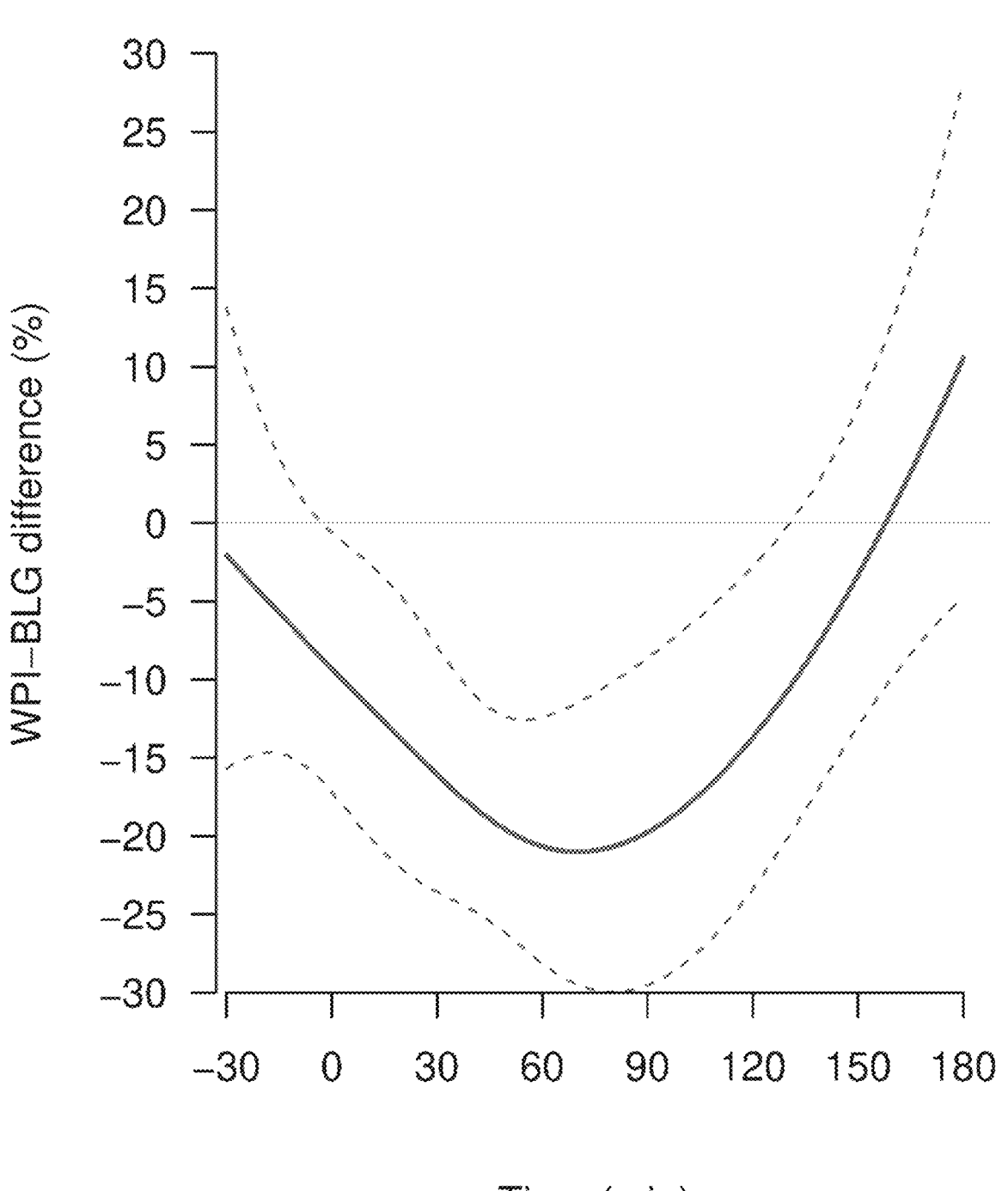
Figure 12:
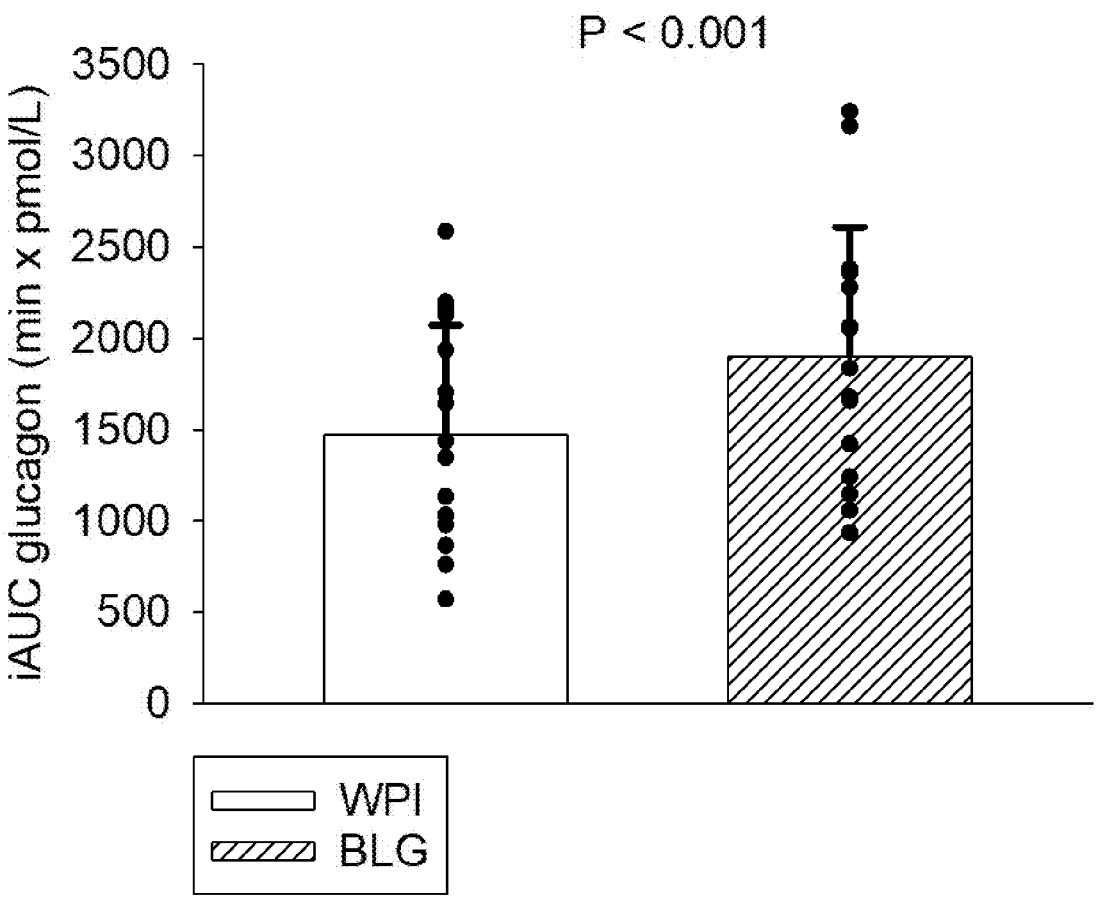
Figure 13:
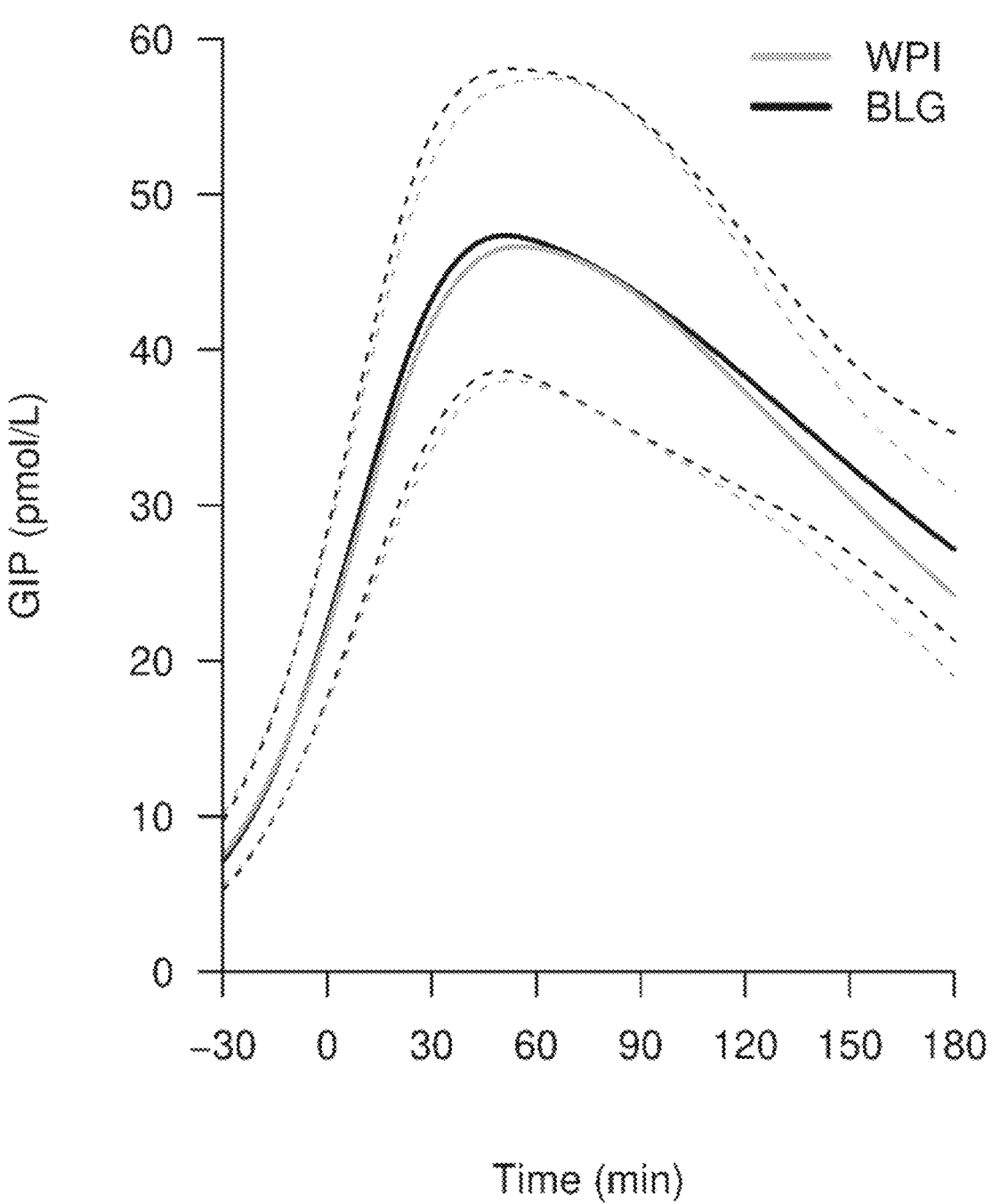
FIG. 13a+b illustrates the mean plasma GIP curves by intervention (black: BLG, grey: WPI) and their difference as percentage, both with 95% CIs based on a mixed effect model.
FIG. 13c illustrates the individual incremental area under the curve (iAUC) with a bar plot that shows the mean±standard deviation.
Figure 13:
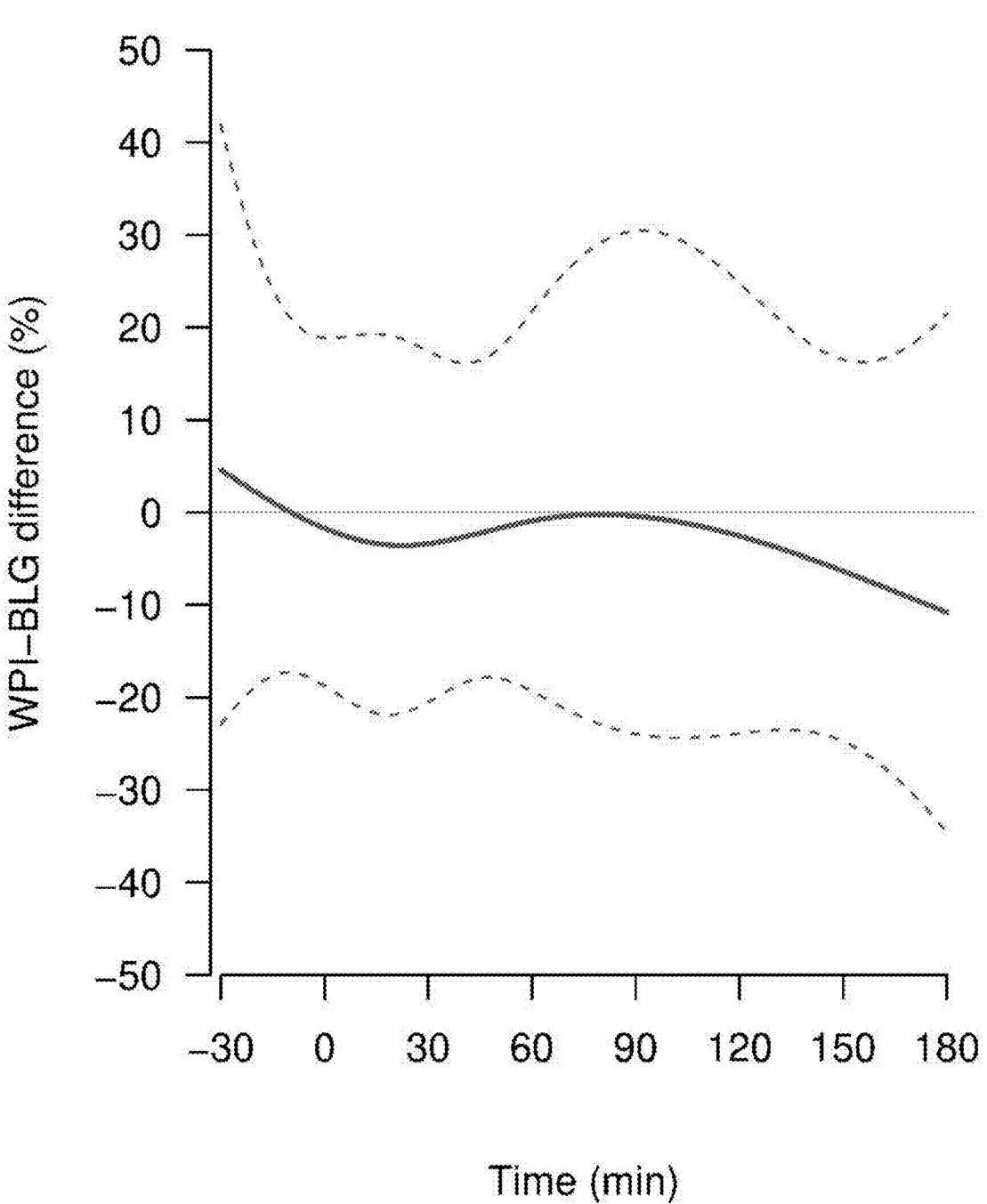
Figure 13:
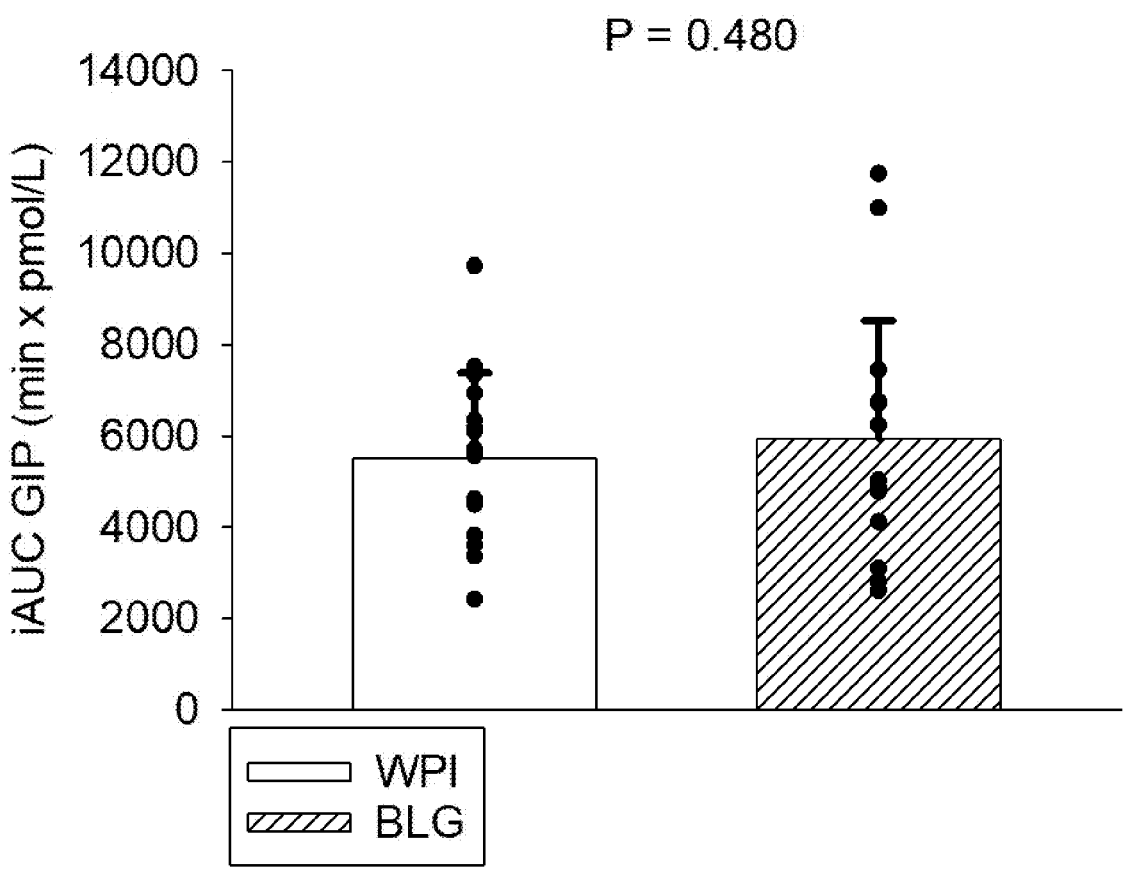
Figure 14:
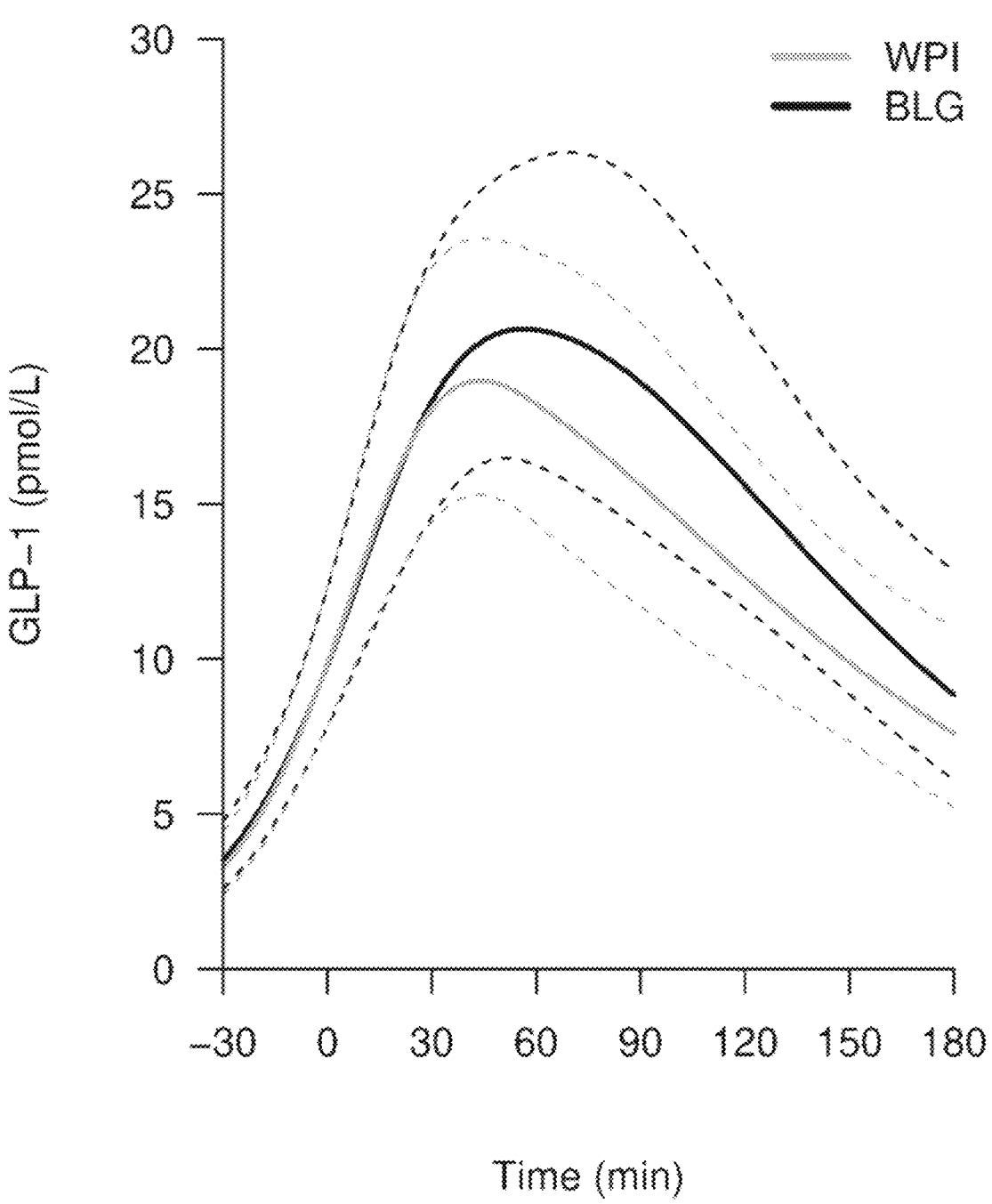
FIG. 14a+b illustrates the mean plasma GLP-1 curves by intervention (black: BLG, grey: WPI) and their difference as percentage, both with 95% CIs based on a mixed effect model.
FIG. 14c illustrates the individual incremental area under the curve (iAUC) with a bar plot that shows the mean±standard deviation.
Figure 14:
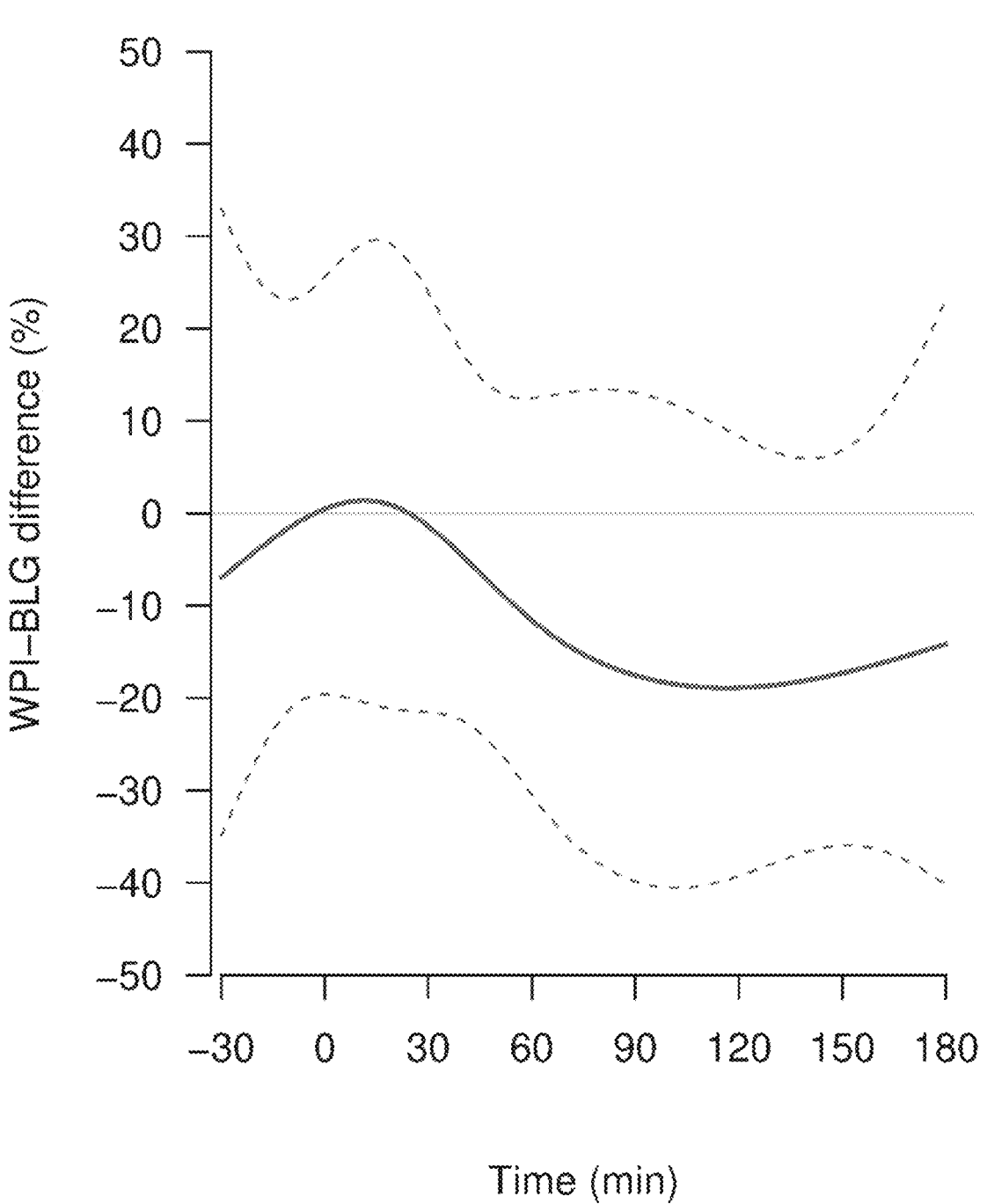
Figure 14:
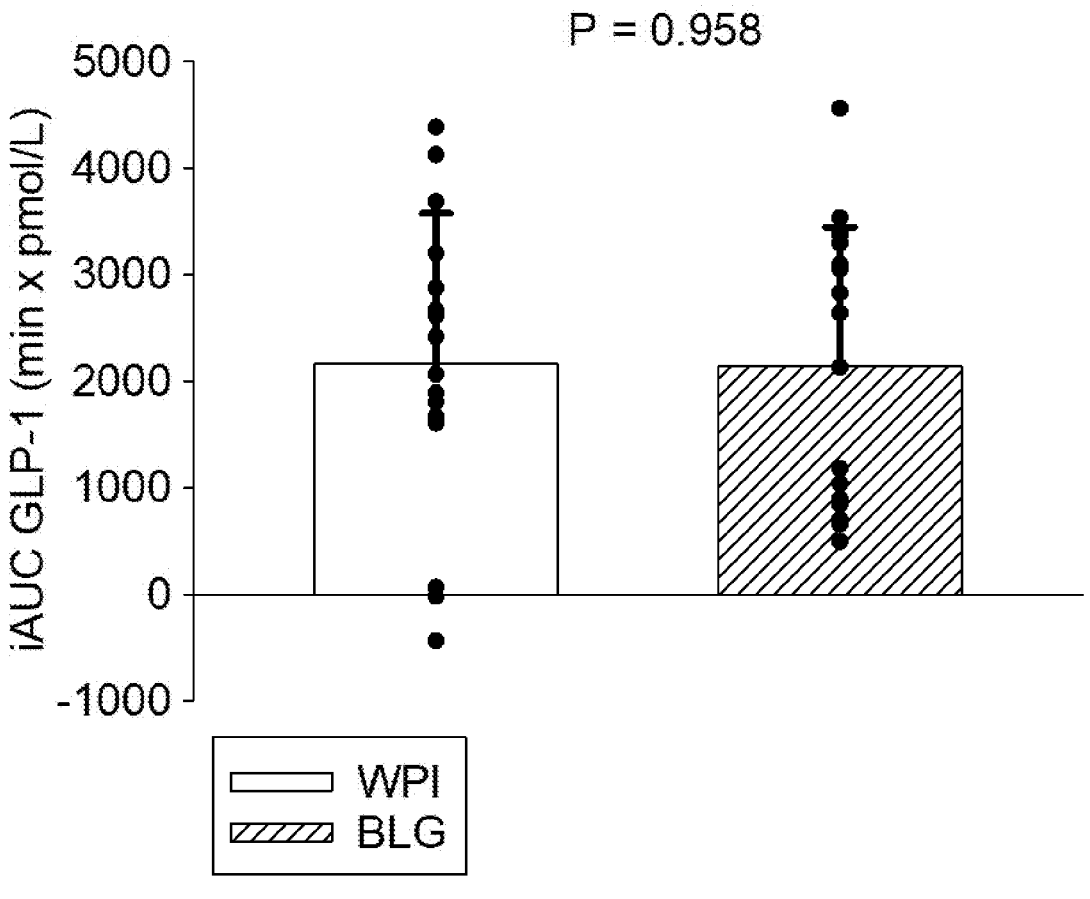
Figure 15:
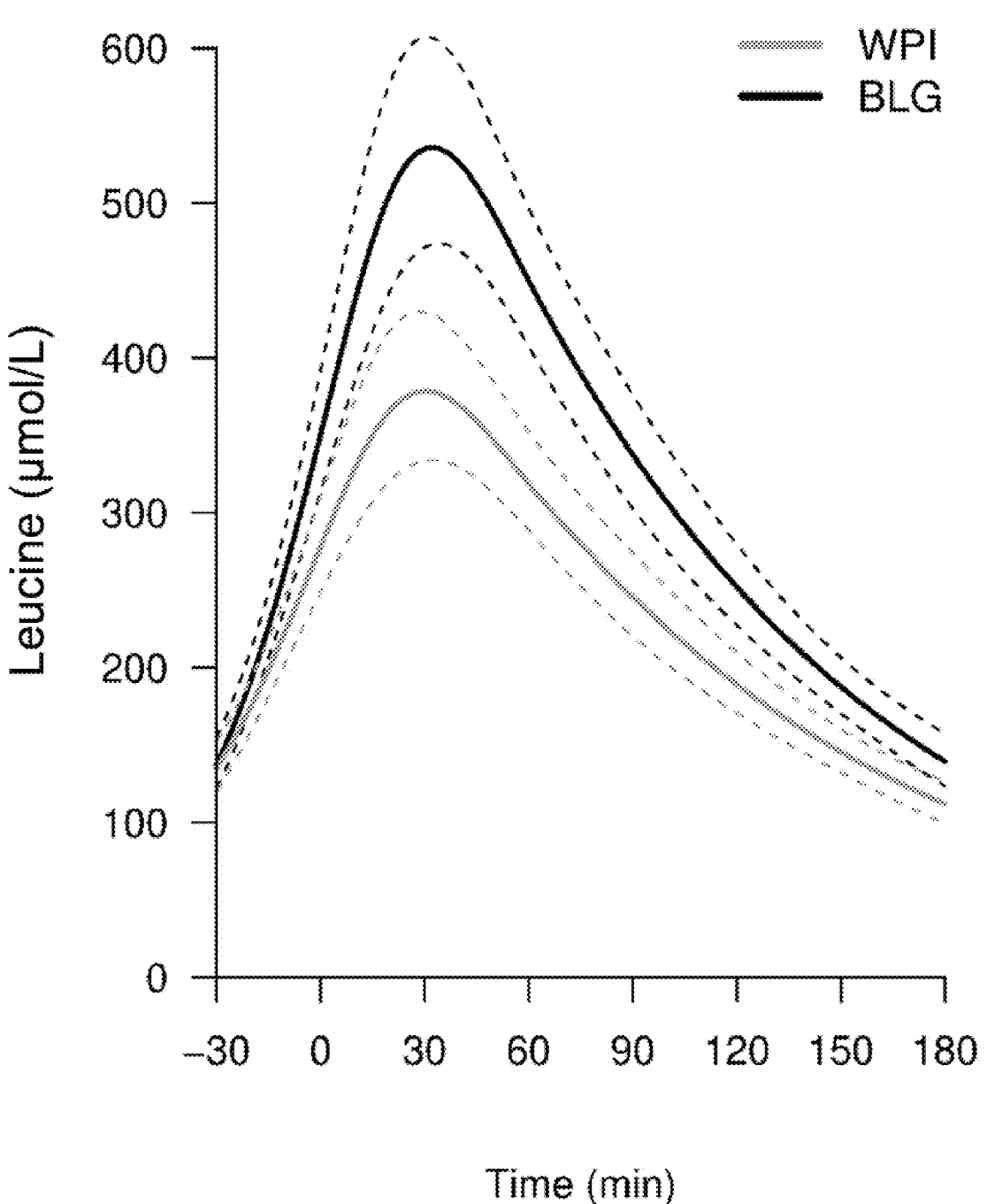
FIG. 15a+b illustrates the mean plasma leucine curves by intervention (black: BLG, grey: WPI) and their difference as percentage, both with 95% CIs based on a mixed effect model.
FIG. 15c illustrates the individual incremental area under the curve (iAUC) with a bar plot that shows the mean±standard deviation.
Figure 15:
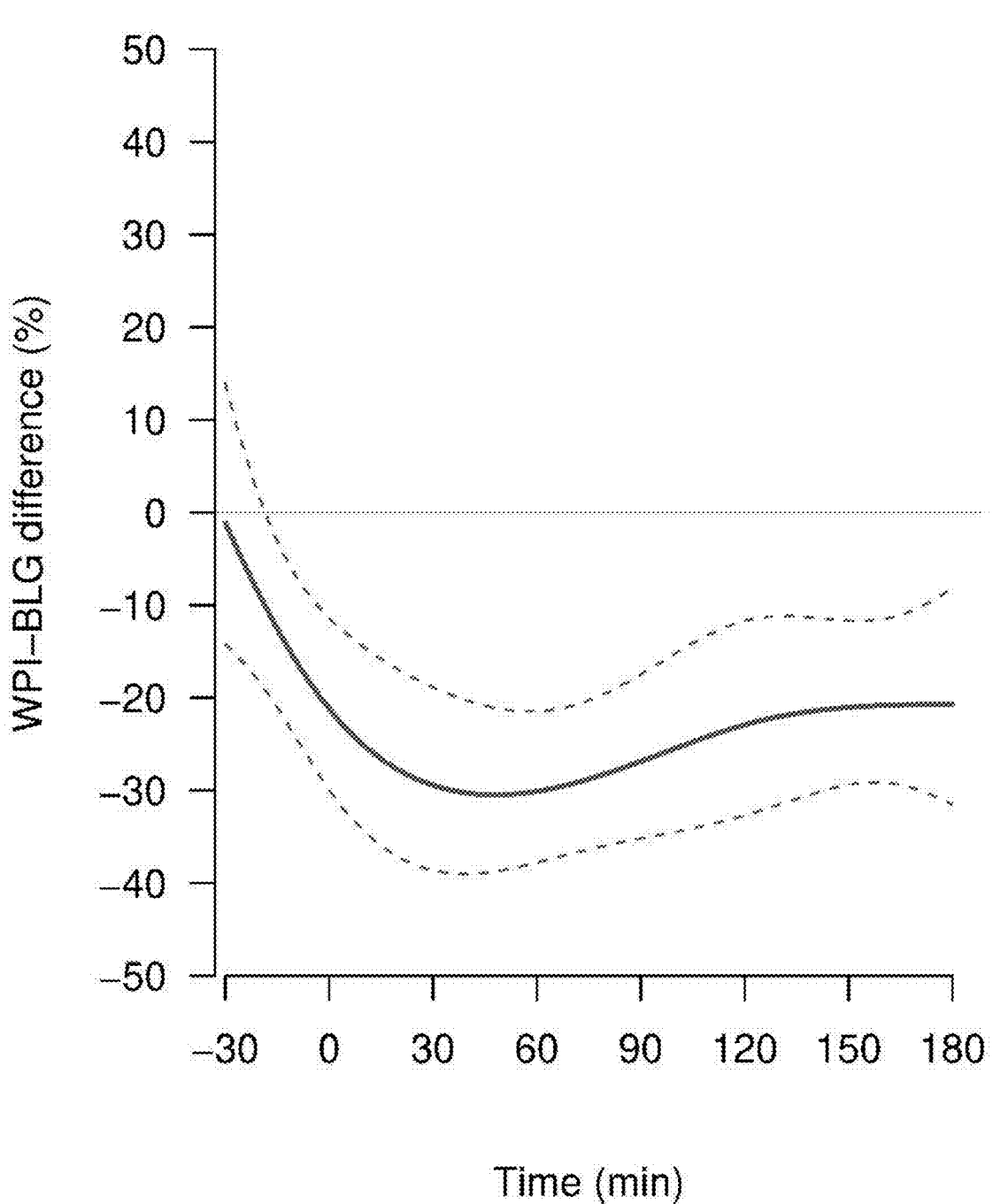
Figure 15:
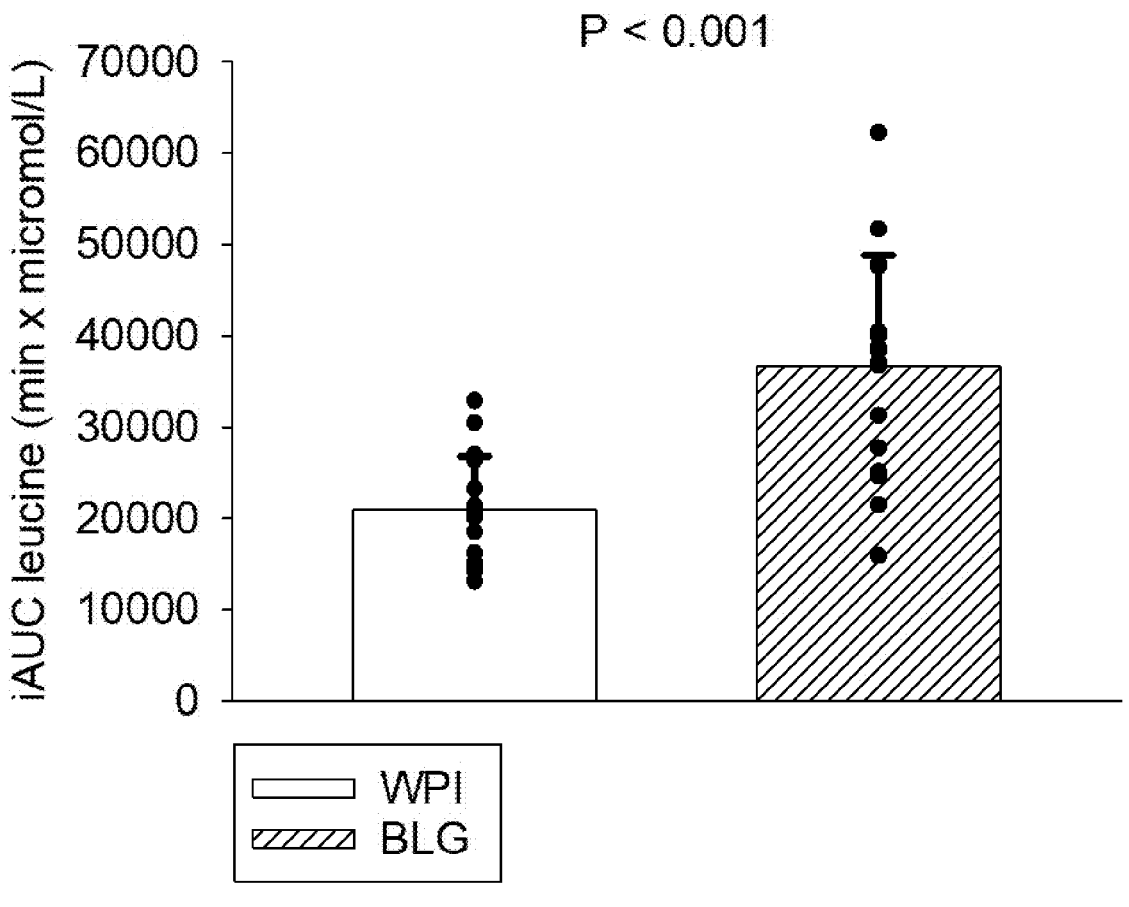
Figure 16:
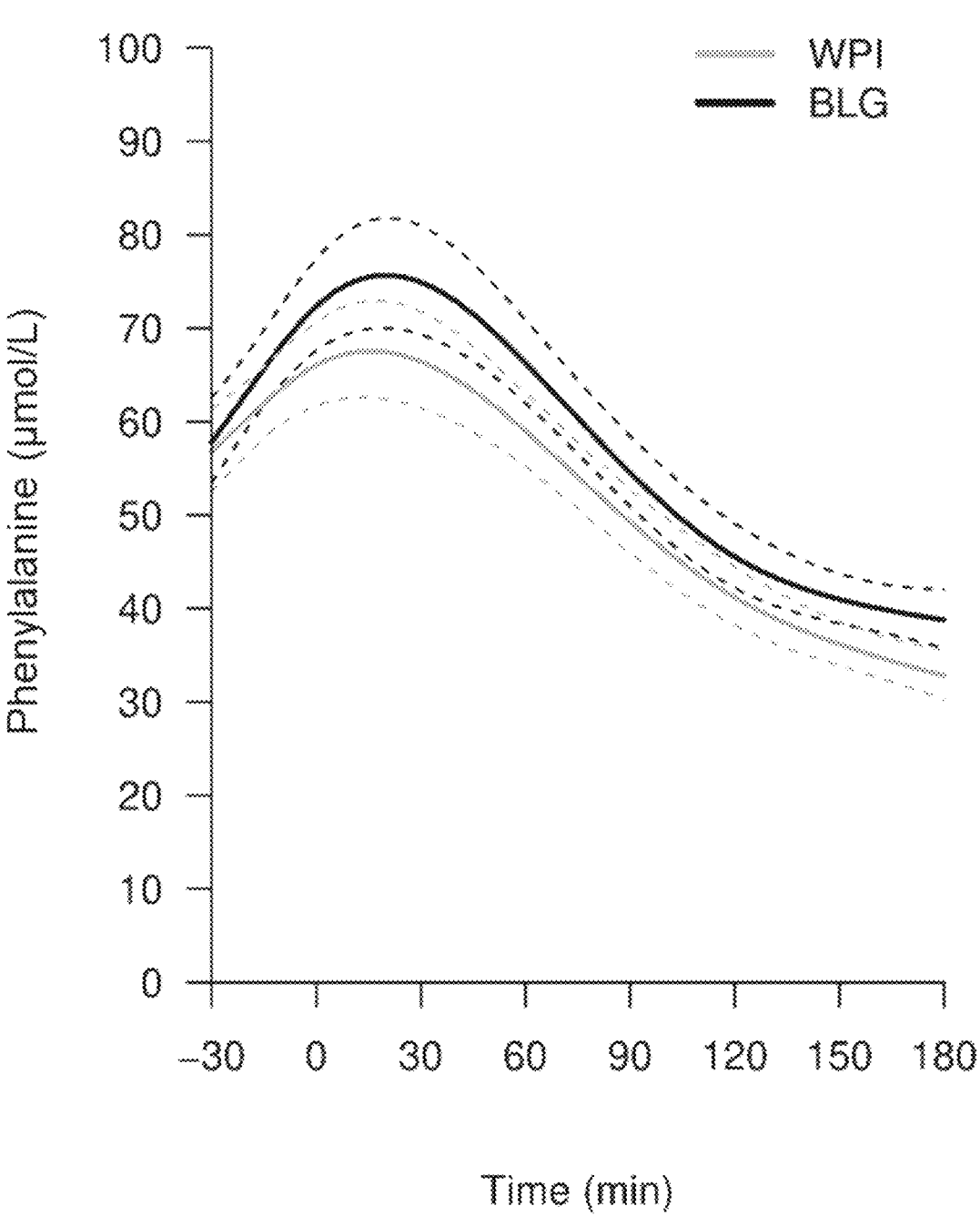
FIG. 16a+b illustrates the mean plasma phenylalanine curves by intervention (black: BLG, grey: WPI) and their difference as percentage, both with 95% CIs based on a mixed effect model.
FIG. 16c illustrates the individual incremental area under the curve (iAUC) with a bar plot that shows the mean±standard deviation.
Figure 16:
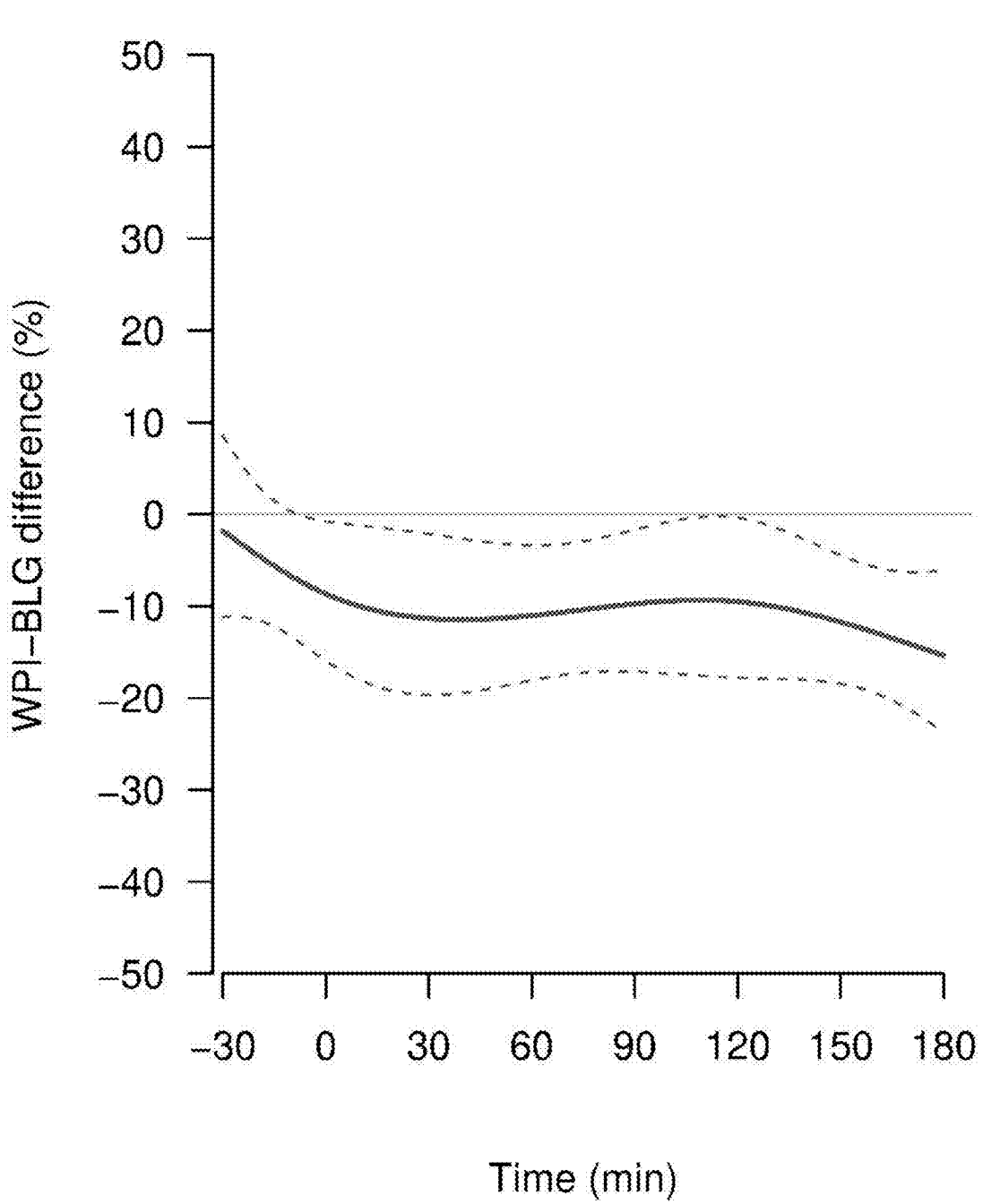
Figure 16:
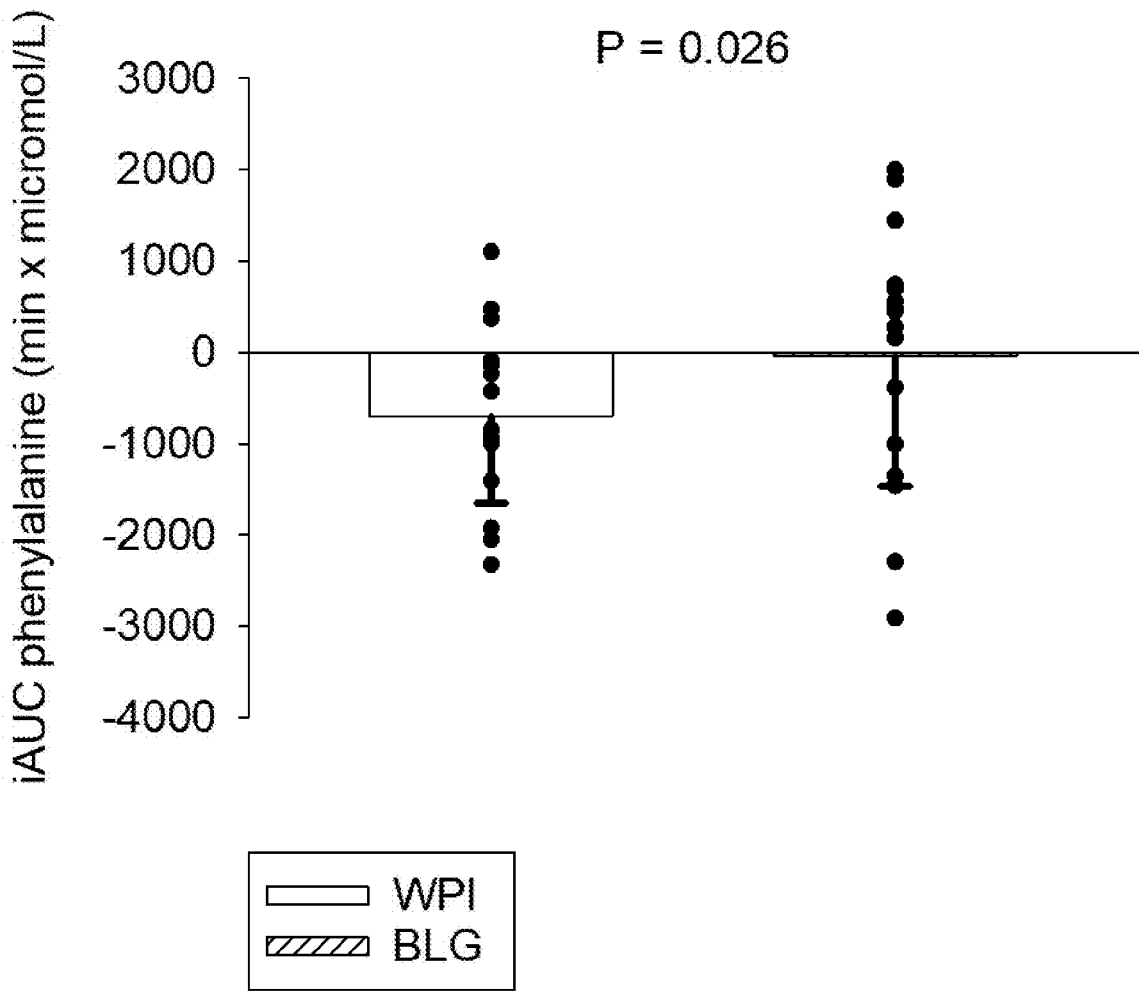
Figure 17:
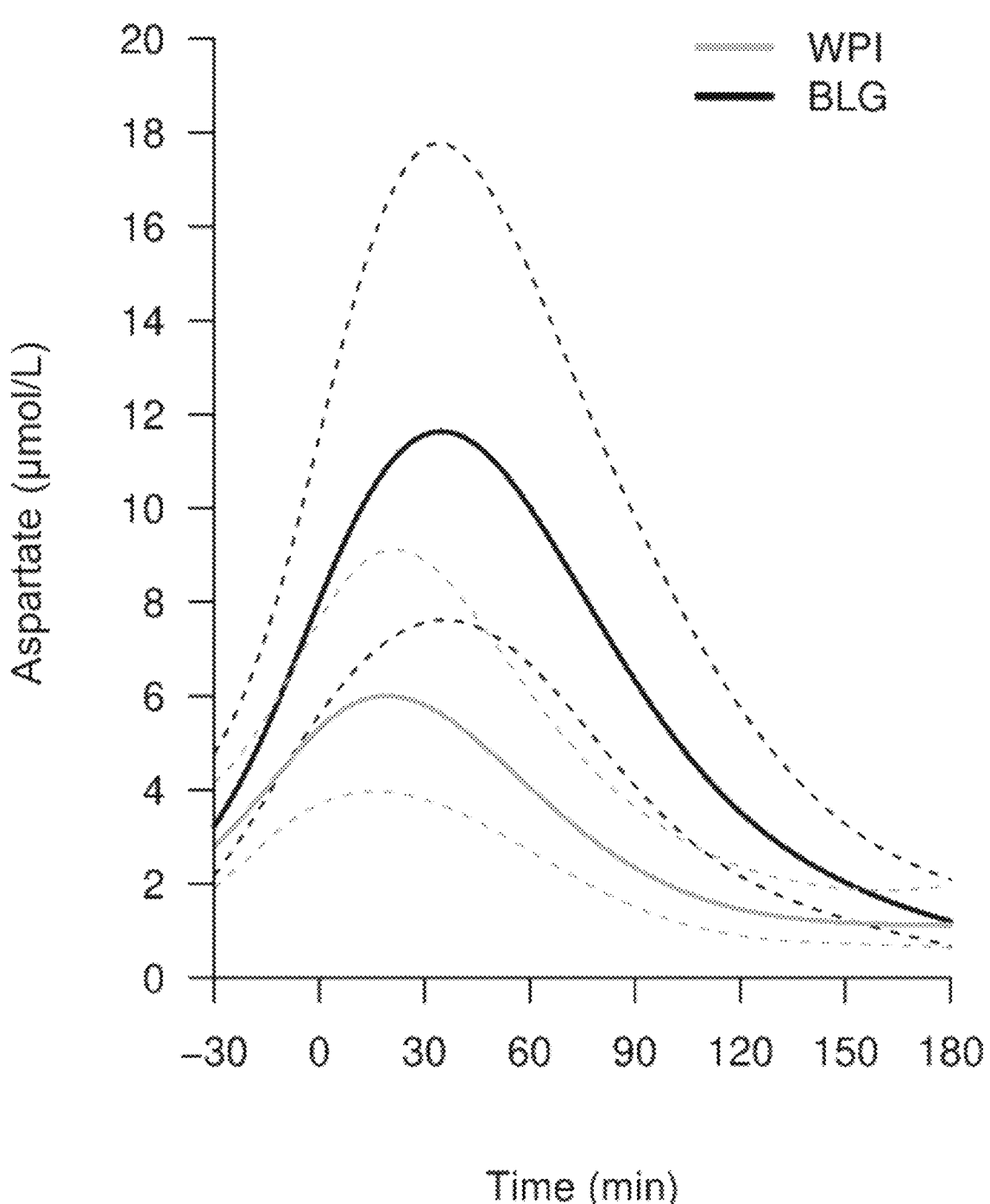
FIG. 17a+b illustrates the mean plasma aspartate curves by intervention (black: BLG, grey: WPI) and their difference as percentage, both with 95% CIs based on a mixed effect model.
FIG. 17c illustrates the individual incremental area under the curve (iAUC) with a bar plot that shows the mean±standard deviation.
Figure 17:
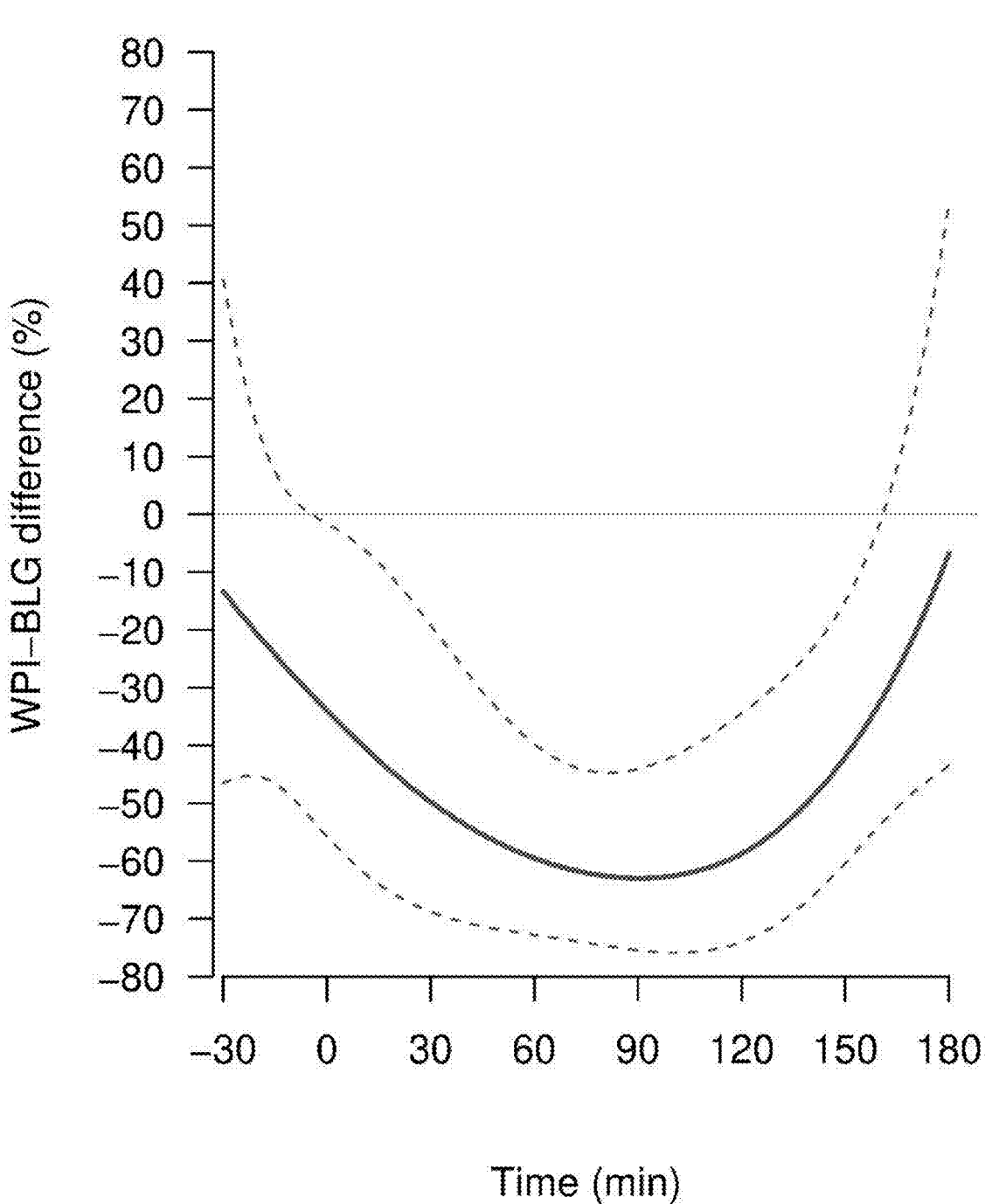
Figure 17:
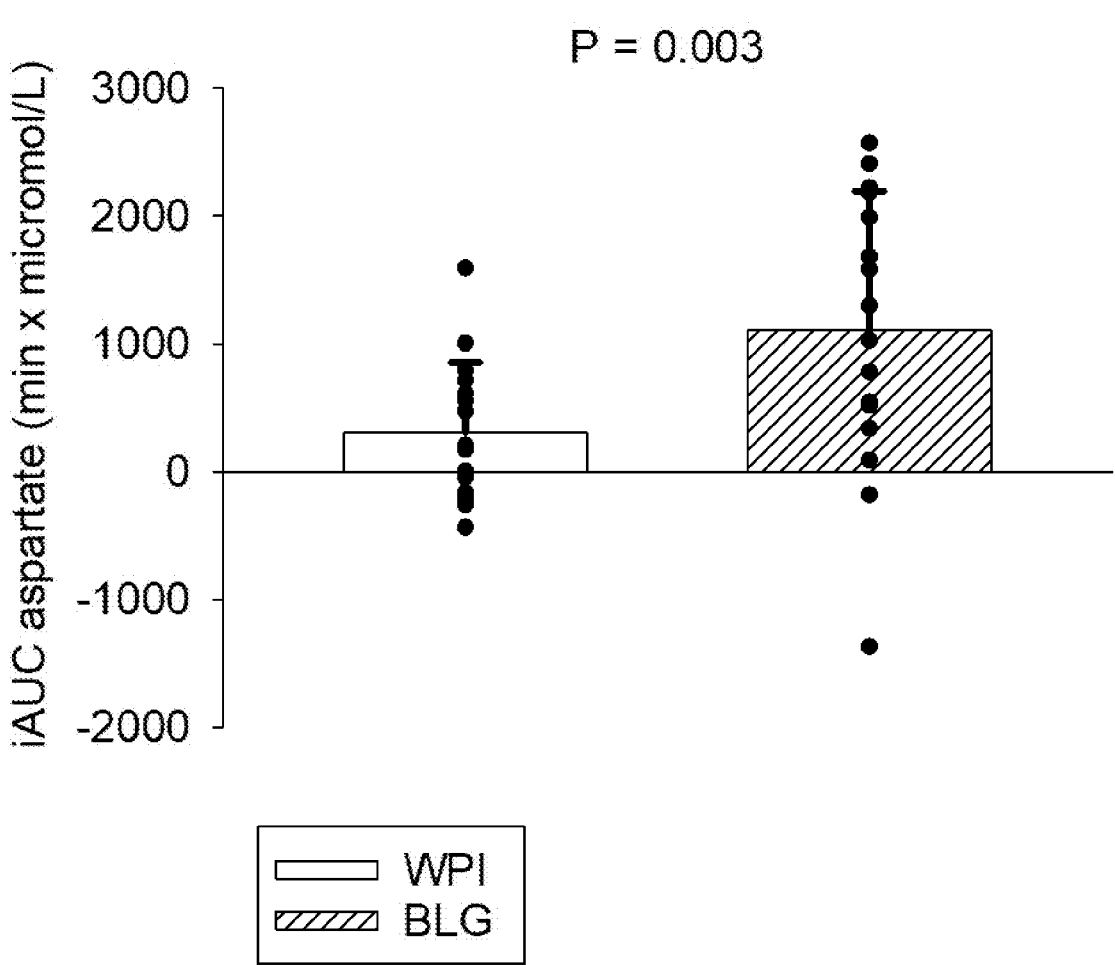

52 increased with ~10% and serum glucagon was increased with ~20% following BLG consumption compared with WPI (FIGS. 11 and 12). Both BLG and WPI increased plasma GIP and plasma GLP-1 concentrations (FIGS. 13 and 14). The plasma-concentrations of aspartate, glutamate, lysine, leucine, methionine, phenylalanine, proline and tyrosine were elevated after BLG consumption compared with WPI (FIG. 15-22).

The OGTT data show that BLG pre-meals served 30 min before an OGTT result in higher concentrations of insulin, glucagon and glucose compared with WPI in patients with T2DM. We had expected BLG to lower glucose more in T2DM individuals because of its higher insulinotropic effects. However, as BLG surprisingly also has a higher glucagonotropic effect than WPI, the glucose lowering effect of BLG compared with WPI is not as high. The difference between the proteins in insulin and glucagon increasing abilities might be found in BLG's unique composition of amino acids. BLG contains more leucine and phenylalanine which have both been shown to stimulate insulin secretion. Likewise, methionine and tyrosine have been shown to increase glucagon concentrations. Studies on dogs and rodents have shown aspartate, glutamate, lysine, and proline to stimulate glucagon secretion as well. All these aforementioned amino acids were more elevated in plasma after BLG consumption compared with WPI. There were no difference in GIP concentrations (an important stimulator of glucagon). We therefore find it likely that the difference in insulin and glucagon concentrations is attributable to the specific AA composition of BLG.

Continuous Glucose Monitoring (CGM)—Glucose Trajectories

Figure 23:
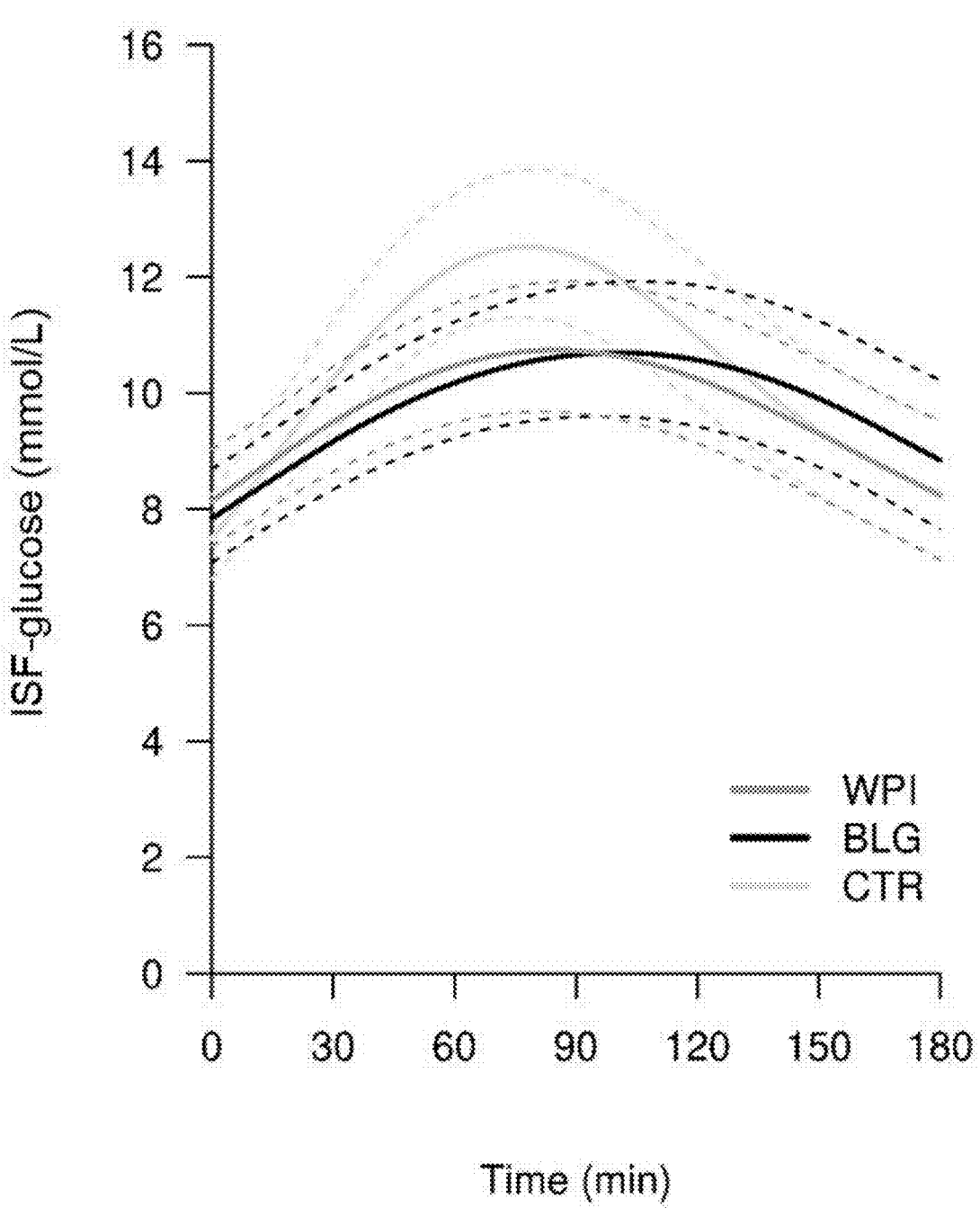
FIG. 23 c illustrates the individual incremental area under the curve (iAUC) with a bar plot that shows the mean±standard deviation. One way RM ANOVA, time×interventions, P=0.002, and post hoc (Student-Newman Keul) paired t-tests: a) $P_{WPI\ vs\ CTR}$=0.002, b) $P_{BLG\ vs\ CTR}$=0.08, c) $P_{WPI\ vs\ BLG}$=0.052.
Figure 23:
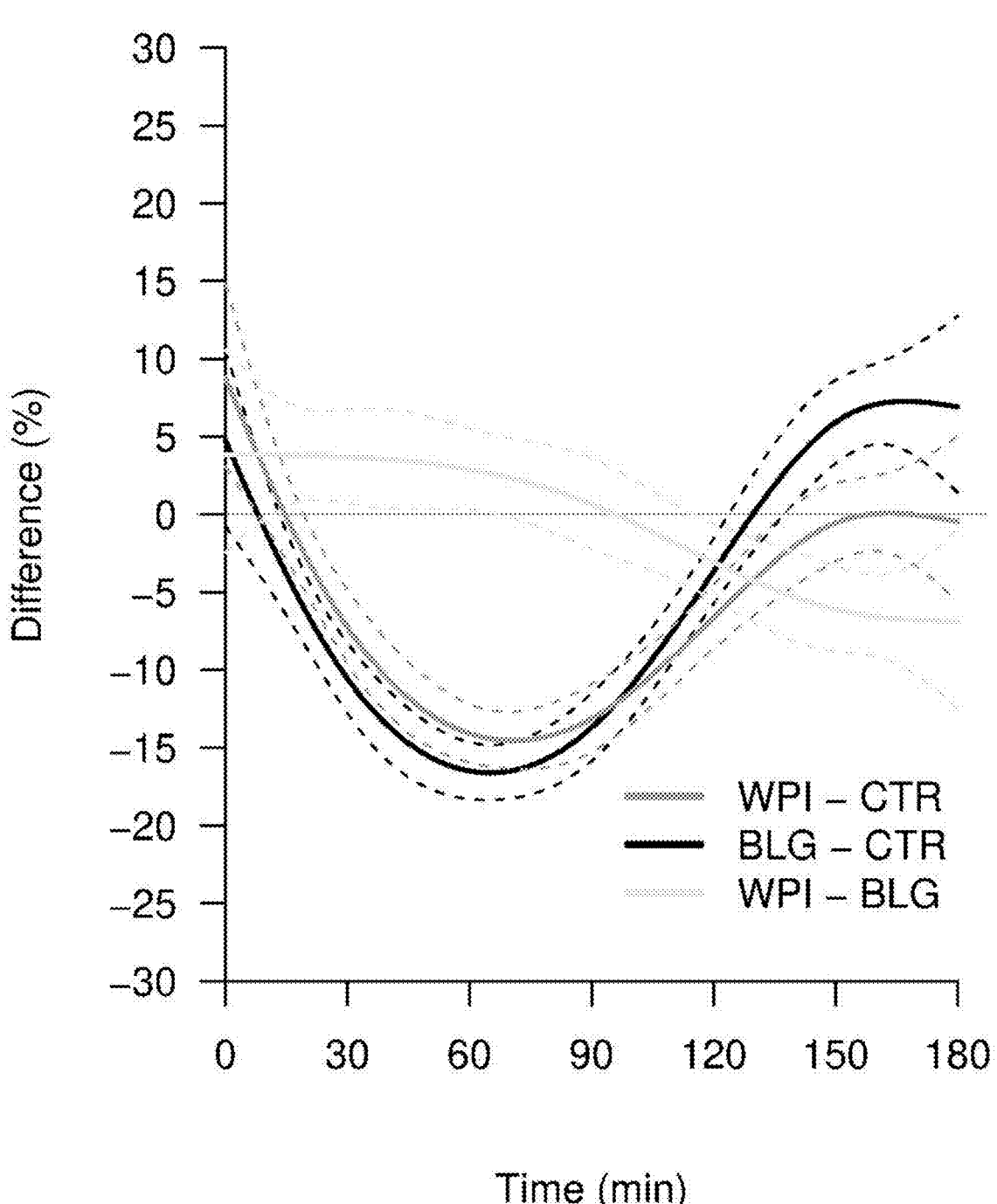
Figure 23:
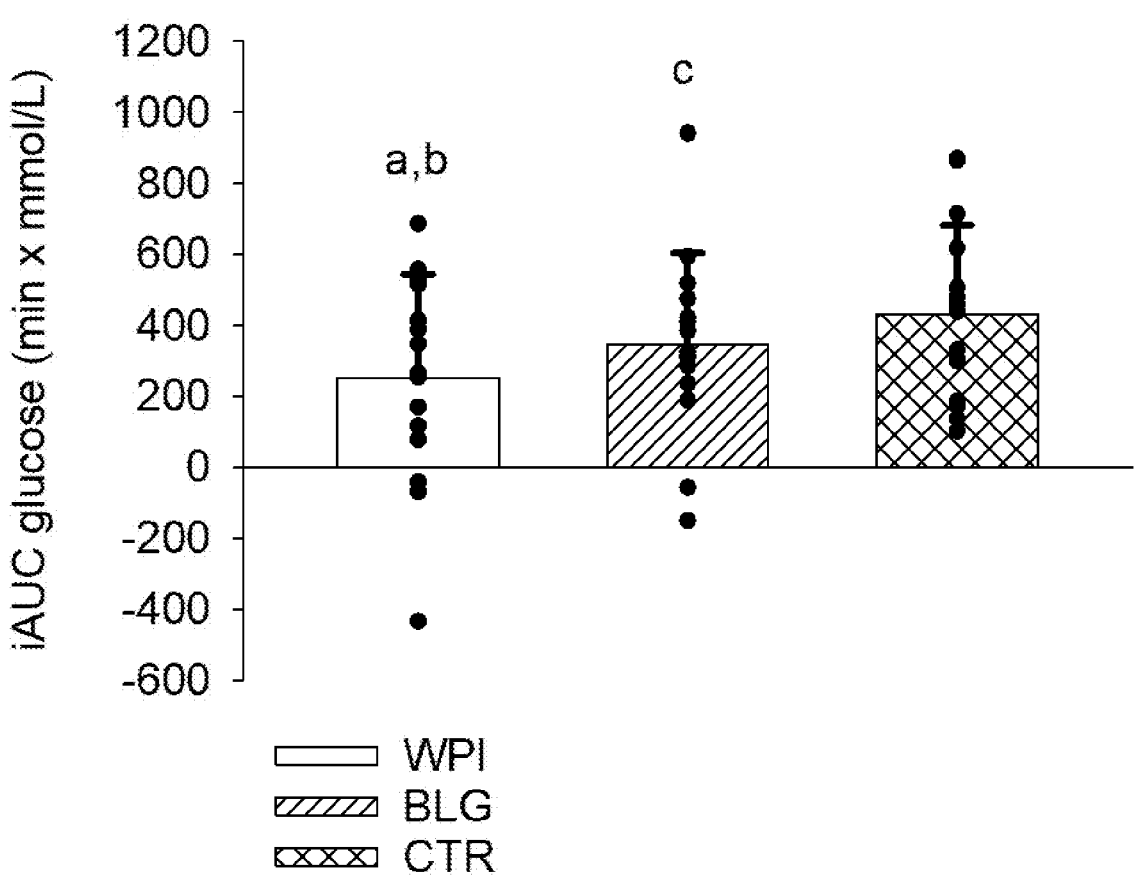

Both BLG and WPI pre-meals lowered postprandial interstitial fluid (ISF)-glucose concentration following breakfast compared to CTR/water. The largest difference was of ~15% around ~60 minutes. ISF-glucose was ~8% lower after ~150 minutes following WPI consumption compared with BLG (FIG. 23).

Continuous Glucose Monitoring CGM—Summary Statistics

Mean ISF-glucose was similar for BLG, WPI and CTR. The CV % was lowered with 9.5% after WPI consumption and with 15.4% after BLG consumption compared with CTR. The standard deviation (SD) was lowered with 9.1% after WPI consumption and with 13.1% after BLG compared with CTR. The maximum glucose levels after breakfast was 12.7% lower after WPI consumption and 11.7% lower after BLG consumption compared with CTR. The daily maximum glucose level was 6.9% lower after WPI consumption and 4.8% lower after BLG consumption compared with CTR. There was no statistically significant difference between BLG and WPI in any of the CGM summary variables (Table 2).

TABLE 2

| | CGM summary variables | | |
|---|---|---|---|
| n = 15 | Mean glucose, mmol/l | SD, mmol/l | CV, % |
| CTR | 8.69 (7.86-9.51) | 1.97 (1.75-2.18) | 22.70 (21.34-24.06) |
| WPI | 8.80 (7.96-9.65) | 1.79 (1.55-2.02) | 20.55 (18.87-22.22) |
| BLG | 8.85 (8.01-9.70) | 1.71 (1.48-1.94) | 19.20 (17.53-20.88) |
| WPI − CTR | 0.12 (−0.18-0.42) | −0.18 (−0.34-(−0.02))** | −2.15 (−3.86-(−0.45))* |
| BLG − CTR | 0.17 (−0.13-0.47) | −0.26 (−0.42-(−0.10))** | −3.49 (−5.20-(−1.79))** |
| WPI − BLG | −0.05 (−0.39-0.29) | 0.08 (−0.11-0.26) | 1.34 (−0.62-3.31) |

TABLE 2-continued

| | CGM summary variables | | | | | |
|---|---|---|---|---|---|---|
| n = 15 | Max after breakfast, mmol/l | | Daily max, mmol/l | | Max after dinner, mmol/l | |
| CTR | 14.35 | (13.06-15.63) | 14.54 | (13.20-15.87) | 10.80 | (9.76-11.84 |
| WPI | 12.52 | (11.20-13.85) | 13.53 | (12.15-14.90) | 10.88 | (9.73-12.03) |
| BLG | 12.67 | (11.35-13.99) | 13.84 | (12.47-15.22) | 10.98 | (9.82-12.14) |
| WPI − CTR | −1.82 | (−2.38-(−1.27))* | −1.01 | (−1.56-(−0.44)** | 0.08 | (−0.82-0.97) |
| BLG − CTR | −1.68 | (−2.23-(−1.12))** | −0.70 | (−1.27-(−0.12)* | 0.18 | (−0.73-1.09) |
| WPI − BLG | −0.15 | (−0.79-0.49) | −0.32 | (−0.98-0.35) | −0.12 | (−1.14-0.93) |

Data are presented as means with 95% confidence intervals. Glycemic variability parameters are the coefficient of variation (CV) and standard deviation (SD). Data on the postprandial glucose levels are the maximum (max) glucose after breakfast and dinner during three hours following the meals. CTR, control; WPI, whey protein isolate; BLG, beta-lactoglobulin.
*P < 0.05
**P < 0.01

Glycemic variability, maximum glucose levels and glucose excursions were all reduced after consumption of both pre-meal proteins compared with the control/water making both proteins effective pre-meals in lowering glucose in T2DM. In conclusion, BLG can be used as a pre-meal protein in the treatment of T2DM.

Conclusions:

BLG pre-meals elevate insulin, glucagon and glucose concentrations following an OGTT in patients with T2DM in comparison with WPI. Both protein pre-meals, WPI and BLG, lowered glucose trajectories and glycemic variability in comparison with tap-water.

Glucagon has been shown to increase energy expenditure and inhibit appetite. At the moment bi-agonist of GIP and glucagon and triagonists of GIP, GLP-1 and glucagon are under development for treating obesity. BLG increases the concentrations of all these three hormones and BLG may therefore also be relevant in the treatment and/or prevention of obesity.

We found that BLG increases insulin concentrations more compared with WPI. Insulin is known to effectively damper lipid concentrations in the blood stream, as insulin increases the uptake of lipids in the muscles. Hence, BLG might be effective in the treatment of dyslipidemia.

Metabolic syndrome is characterized by obesity, dyslipidemia and reduced glucose tolerance. The elevation of insulin concentrations after BLG consumption lowers glucose and lipid levels. As mentioned, glucagon has been shown to increase energy expenditure, and therefore we believe, that BLG may have positive effects in weight management.

Whey has been shown to promote muscle protein synthesis, improve nutritional status in cachexic patients and improve muscle mass and inhibit inflammation in patients with sarcopenia. These effects have been attributed to the high content of leucine in whey. BLG has a higher leucine content compared with WPI and in addition to this we have found that BLG surprisingly promotes a greater insulin response. We therefore believe that BLG is beneficial in patients with sarcopenia, cachexia, malnutrition and immobilization or reduced physical activity.

The invention claimed is:

1. A method of treating muscle atrophy in a subject, the method comprising: orally administering to a human subject in need thereof, a therapeutically effective amount of protein provided by: a) beta-lactoglobulin; or b) a nutritional composition comprising beta-lactoglobulin, wherein: (i) said beta-lactoglobulin is present in an amount of at least 75% w/w relative to total protein; and (ii) the oral administration of a) or b) to the subject increases the level of insulin in the blood of the subject when compared to a subject orally administered the same amount of protein provided by a whey protein isolate (WPI).

2. The method of claim 1, wherein the muscle atrophy is sarcopenia or cachexia.

3. The method of claim 1, wherein the method involves regulating the level of glucose, insulin, glucagon, glucose-dependent insulinotropic polypeptide (GIP) and/or glucagon-like peptide-1 (GLP-1) in the blood.

4. The method of claim 1, wherein the oral administration of a) or b) to the subject increases the level of glucose-dependent insulinotropic polypeptide (GIP) in the blood of the subject when compared to a subject orally administered the same amount of protein provided by a whey protein isolate (WPI).

5. The method of claim 1, wherein the oral administration of a) or b) to the subject increases the level of glucagon-like peptide-1 (GLP-1) in the blood of the subject when compared to a subject orally administered the same amount of protein provided by a whey protein isolate (WPI).

6. The method of claim 1, wherein the oral administration of a) or b) to the subject lowers the level of glucose in the blood of the subject when compared to a subject orally administered the same amount of protein provided by a whey protein isolate (WPI).

7. The method of claim 1, wherein the oral administration of a) or b) to the subject increases the amount of amino acids stimulating the concentration of glucagon and/or insulin in the blood when compared to a subject orally administered the same amount of protein provided by a whey protein isolate (WPI).

8. The method of claim 7, wherein the amino acids are tyrosine, methionine, proline, aspartate, glutamate, lysine, leucine and/or phenylalanine.

9. The method of claim 1, wherein the subject is at risk of sarcopenia or cachexia.

10. The method of claim 1, wherein the subject is suffering from sarcopenia, cachexia or sarcopenia and cachexia.

11. The method of claim 1, wherein the nutritional composition comprises beta-lactoglobulin in an amount of at least 80% w/w relative to total protein.

12. The method of claim 1, wherein the nutritional composition b) comprises a total amount of protein of at least 1.0% w/w relative to the weight of the nutritional composition.

13. The method of claim 1, wherein a) the beta-lactoglobulin or b) the nutritional composition is administered to the subject in a serving dose of at least 0.01 g protein/kg body weight.

14. The method of claim 1, wherein a) the beta-lacto-globulin or b) the nutritional composition is administered to the subject in a serving dose of 0.01 to 0.60 g protein/kg body weight.

15. The method of claim 1, wherein a) the beta-lacto-globulin or b) the nutritional composition is administered to a subject in a daily dose of at least 0.03 g protein/kg body weight.

16. The method of claim 1, wherein a) the beta-lacto-globulin or b) the nutritional composition is administered as a pre-meal.

17. The method of claim 1, wherein a) the beta-lacto-globulin or b) the nutritional composition is administered 0-60 minutes prior to a meal.

18. The method of claim 1, wherein a) the beta-lacto-globulin has a degree of protein denaturation of at most 10%.

19. The method of claim 1, wherein a) the beta-lacto-globulin or b) the nutritional composition is administered in combination with an additional medicament.

* * * * *